(12) United States Patent
Edgar et al.

(10) Patent No.: US 7,592,333 B2
(45) Date of Patent: Sep. 22, 2009

(54) LOXAPINE ANALOGS AND METHODS OF USE THEREOF

(75) Inventors: Dale M. Edgar, Wayland, MA (US); David G. Hangauer, East Amherst, NY (US); Kazumi Shiosaki, Wellesley, MA (US); Michael Solomon, Concord, MA (US); James F. White, Carlisle, MA (US)

(73) Assignee: Hypnion, Inc., Indianapolis, IN (US)

( * ) Notice: Subject to any disclaimer, the term of this patent is extended or adjusted under 35 U.S.C. 154(b) by 617 days.

(21) Appl. No.: 11/233,417

(22) Filed: Sep. 21, 2005

(65) Prior Publication Data

US 2006/0063928 A1 Mar. 23, 2006

Related U.S. Application Data

(60) Provisional application No. 60/611,849, filed on Sep. 21, 2004, provisional application No. 60/673,198, filed on Apr. 19, 2005.

(51) Int. Cl.
*A61P 25/00* (2006.01)
*A61K 31/554* (2006.01)
*C07D 267/02* (2006.01)

(52) U.S. Cl. .................... 514/211.13; 540/551

(58) Field of Classification Search ............ 514/211.13; 540/551
See application file for complete search history.

(56) References Cited

U.S. PATENT DOCUMENTS

| 3,546,226 | A | 12/1970 | Schmutz et al. ............. 260/268 |
| 3,928,356 | A | 12/1975 | Umio et al. ............ 260/268 TR |
| 4,072,756 | A | 2/1978 | Ebnother et al. ............ 424/267 |
| 5,344,828 | A | 9/1994 | Sawanishi et al. ............ 514/211 |
| 7,355,042 | B2 | 4/2008 | Edgar et al. .................. 540/542 |
| 2006/0063754 | A1 | 3/2006 | Edgar et al. ............ 514/211.13 |

FOREIGN PATENT DOCUMENTS

| EP | 0 447 857 A1 | 9/1991 |
| WO | WO 97/45422 | 12/1997 |
| WO | WO 03/039255 A1 | 5/2003 |
| WO | WO 2004/056182 A1 | 7/2004 |

OTHER PUBLICATIONS

Patent Abstracts of Japan for JP 03184963 A2, published Aug. 12, 1991.
Chemical Abstracts Service HCAplus and MARPAT file records for JP 09020755, published Jan. 21, 1997.
Muramatsu et al., *Yakugaku Zasshi*, 112(7)479-488 (1992).
Monti et al., "Histamine $H_1$ Receptor Antagonists in the Treatment of Insomnia: Is There a Rational Basis for Use?", *CNS Drugs*, 13(2):87-96 (2000).

*Primary Examiner*—Brenda L Coleman
(74) *Attorney, Agent, or Firm*—Ivor R. Elrifi; Heidi A. Erlacher; Mintz, Levin, Cohn, Ferris, Glovsky and Popeo, P.C.

(57) ABSTRACT

The invention relates to novel compounds and methods of using them for modulating sleep.

14 Claims, No Drawings

LOXAPINE ANALOGS AND METHODS OF USE THEREOF

RELATED APPLICATIONS

This non-provisional patent application claims priority under 35 U.S.C. § 119(e) to U.S. Provisional Patent Application Ser. Nos. 60/611,849, filed Sep. 21, 2004, and 60/673,198, filed Apr. 19, 2005, each of which is herein incorporated by reference in its entirety. This application is also related to copending application entitled "Loxapine Analogs and Methods of use Thereof", Ser. No. 11/232,590, filed on Sep. 21, 2005.

FIELD OF THE INVENTION

The invention relates to methods for treating sleep disorders and compositions useful in such methods.

BACKGROUND OF THE INVENTION

Difficulty falling asleep or remaining asleep is a significant medical issue that arises for a variety of reasons. Sometimes, these problems arise from endogenous conditions such as sleep apnea or insomnia. Other times, these problems arise from exogenous stresses such as the disruptive effect of shift work schedules and "jet lag." Whether caused by an endogenous or exogenous source, difficulty falling asleep or remaining asleep can result in problem sleepiness, which impairs the health, quality of life, and safety of those affected.

Existing pharmaceutical treatments for inducing sleep include sedatives or hypnotics such as benzodiazepine and barbiturate derivatives. These treatments have numerous drawbacks, including rebound insomnia, delayed onset of desired sedative effects, persistence of sedative effects after the desired sleep period, and side effects due to nonspecific activity such as psychomotor and memory deficits, myorelaxation, and disturbed sleep architecture, including REM sleep inhibition. Additionally, sedatives and hypnotics can be habit forming, can lose their effectiveness after extended use, and may be metabolized more slowly by some people.

Consequently, physicians often recommend or prescribe antihistamines as a milder treatment for sleep disorders when hypnotics are less appropriate. However, many antihistamines suffer from a number of side effects. These side effects include prolongation of the QT interval in a subject's electrocardiogram, as well as central nervous system (CNS) side effects such as decreased muscle tone and drooping eyelids. Finally, such compounds can bind to muscarinic receptors, which leads to anti-cholinergic side effects such as blurred vision, dry mouth, constipation, urinary problems, dizziness and anxiety.

As a result, there is a need for sleep-promoting treatments with reduced side effects. Additionally, while known sleep-inducing compounds are effective for treating sleep-onset insomnia, i.e., a subject's difficulty in falling asleep, there are no drugs currently indicated for treating sleep maintenance insomnia, i.e., maintaining a subject's sleep throughout a normal sleep period after falling asleep. Therefore, there is also a need for improved pharmaceutical treatments for maintaining sleep in subjects in need of such treatment.

SUMMARY OF THE INVENTION

The present invention relates to loxapine analogs and their use to modulate sleep. Loxapine (LOXAPAC™, LOXITANE™) is a tricyclic dibenzoxazepine antipsychotic agent used in the management of the manifestations of schizophrenia. Loxapine (2-chloro-11-(4-methyl-1-piperazinyl)dibenz[b,f][1,4] oxazepine) has the following structure:

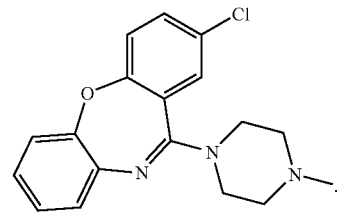

In one aspect, the invention relates to a method of modulating sleep in a subject by administering to the subject a therapeutically effective amount of a compound of Formula I:

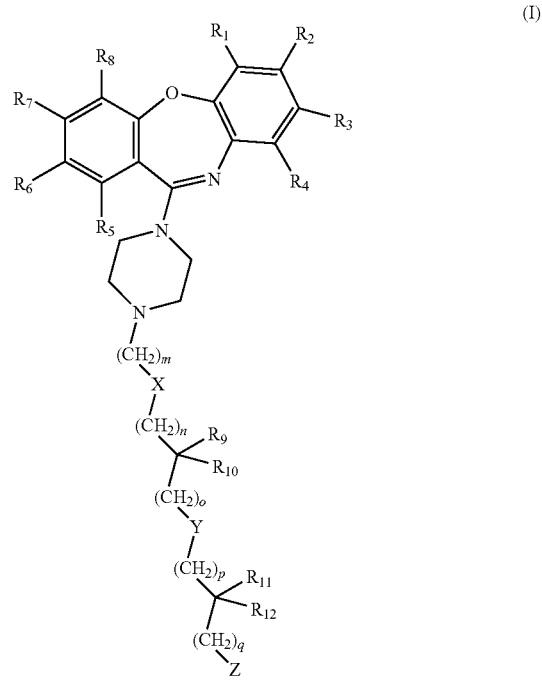

(I)

or a pharmaceutically effective salt thereof, wherein: m, n, o, p, and q are, independently, an integer 0, 1, 2, 3, 4, 5, or 6; X and Y are, independently, absent, O, S, C(O), SO, or $SO_2$; $R_1$, $R_2$, $R_3$, $R_4$, $R_5$, $R_6$, $R_7$, and $R_8$ are, independently, H, F, Cl, Br, OH, $CF_3$, $CH_3$, $C_2$-$C_6$ straight chain alkyl, $C_3$-$C_6$ branched alkyl, $C_3$-$C_7$ cycloalkyl, $C_3$-$C_7$ heterocyclyl, $OCH_3$, $OCF_3$, $CH_2OCH_3$, $CH_2CH_2OCH_3$, $CH_2OCH_2CH_3$, $C_1$-$C_6$ hydroxyalkyl, or $C_1$-$C_6$ alkoxy; any hydrogen in the $CH_2$ groups in the linker is optionally substituted with H, F, Cl, OH, Br, $CF_3$, $CH_3$, $C_2$-$C_6$ straight chain alkyl, $C_3$-$C_6$ branched alkyl, $C_3$-$C_7$ cycloalkyl, $C_3$-$C_7$ heterocyclyl, $OCH_3$, $OCF_3$, $CH_2OCH_3$, $CH_2CH_2OCH_3$, $CH_2OCH_2CH_3$, $C_1$-$C_6$ hydroxyalkyl, or $C_1$-$C_6$ alkoxy; $R_9$, $R_{10}$, $R_{11}$, and $R_{12}$ are, independently, H, $C_1$-$C_6$ straight chain alkyl, $C_2$-$C_6$ branched alkyl, or $R_9$ and $R_{10}$ together with the carbon to which they are attached are absent or are connected to form a spiro ring of size 3, 4, 5, 6, or 7 atoms, or $R_{11}$ and $R_{12}$ together with the carbon to which they are attached are connected to form a spiro ring of size 3, 4, 5, 6, or 7 atoms, or substituents on two different carbon atoms are connected to form a ring of size 3, 4, 5, 6, or 7; Z is selected from $CO_2H$, $CO_2R_{13}$ (where $R_{13}$ is $C_1$-$C_6$ alkyl) $CONR_{14}R_{15}$ (where $R_{14}$ and $R_{15}$ are, independently, hydrogen or lower alkyl) $CONHS(O)_2$-alkyl, $CONHS(O)_2$-cycloalkyl, $CONHS(O)_2$-heteroalkyl, $CONHS(O)_2$-aryl, $CONHS(O)_2$-heteroaryl, $S(O)_2NHCO$-alkyl, $S(O)_2NHCO$-cycloalkyl, $S(O)_2NHCO$-heteroalkyl, $S(O)_2NHCO$-aryl, $S(O)_2NHCO$-heteroaryl, $CONHS(O)_2NH$-alkyl, $CONHS(O)_2NH$-cycloalkyl, $CONHS(O)_2NH$-heteroalkyl, $CONHS(O)_2NH$-aryl, $CONHS(O)_2NH$-heteroaryl, $SO_3H$, $SO_2H$, $S(O)NHCO$-alkyl, $S(O)NHCO$-aryl, $S(O)NHCO$-heteroaryl, $P(O)(OH)_2$, $P(O)OH$,

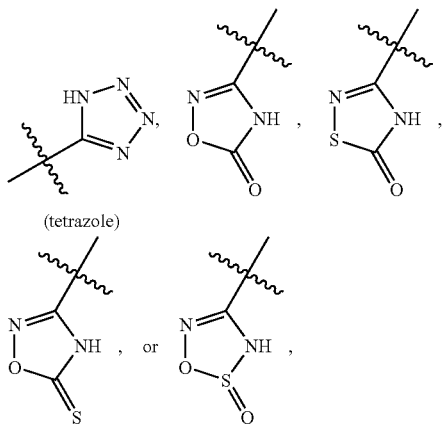

provided that when Z is COOH or $COOR_{13}$, and $R_6$ is H or halogen, $R_1$-$R_5$ and $R_7$-$R_{12}$ are not each hydrogen, further provided that when m is zero, X is absent.

In one embodiment, Z is a sulfonamide. Examples of sulfonamides include acyl sulfonamides. For example, Z can have the formula

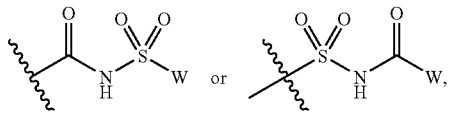

where W is a substituent chosen as needed to modulate the effects of the polar surface area of the Z moiety such that the desired level of oral absorption, CNS penetration, and rate of excretion into urine or bile is obtained. Examples of useful W substituents for this purpose include an alkyl group (optionally containing a double or triple bond or heteroatom substituted e.g., $CH_2OCH_3$ or $CH_2OCH_2CH_3$), a cycloalkyl group (optionally containing a double bond), a heterocyclyl group, an aryl group or a heteroaryl group, both optionally substituted, such as those shown below:

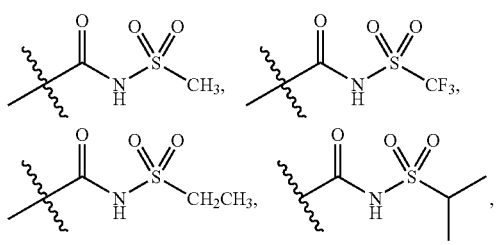

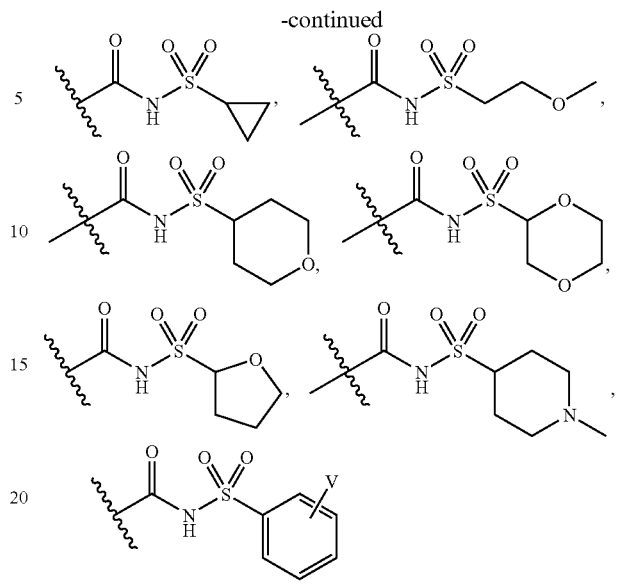

where V is one or more side chains selected to modulate the pKa of the acylsulfonamide moiety, or to affect the physical or metabolic properties of the compound. Examples of V side chains include halogens such as F, Cl, or Br; $C_1$-$C_6$ alkoxy groups such as $OCH_3$ or $OCH_2CH_3$; $C_1$-$C_6$ alkyl or $C_3$-$C_8$ cycloalkyl groups such as $CH_3$, $CF_3$, or cyclopropyl; heteroatom substituted $C_1$-$C_6$ alkyl or $C_3$-$C_8$ cycloalkyl, such as $CH_2OCH_3$, or $CH_2OCH_2CH_3$; electron withdrawing groups such as CN, a ketone, an amide, or a sulfone,

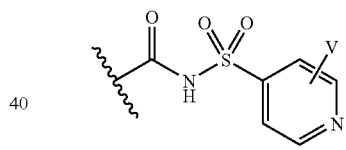

(and pyridyl isomers),

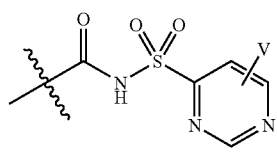

(and pyrimidine isomers), and

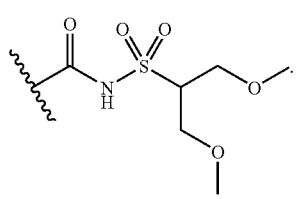

In one embodiment, Z is a sulfamide. Examples of sulfamides include acyl sulfamides. For example, Z can have the formula

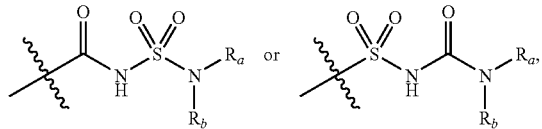

where $R_a$ and $R_b$ are, independently, for example an alkyl group, a cycloalkyl group, a heterocyclyl group, an aryl group or a heteroaryl group, optionally substituted. Examples include the following:

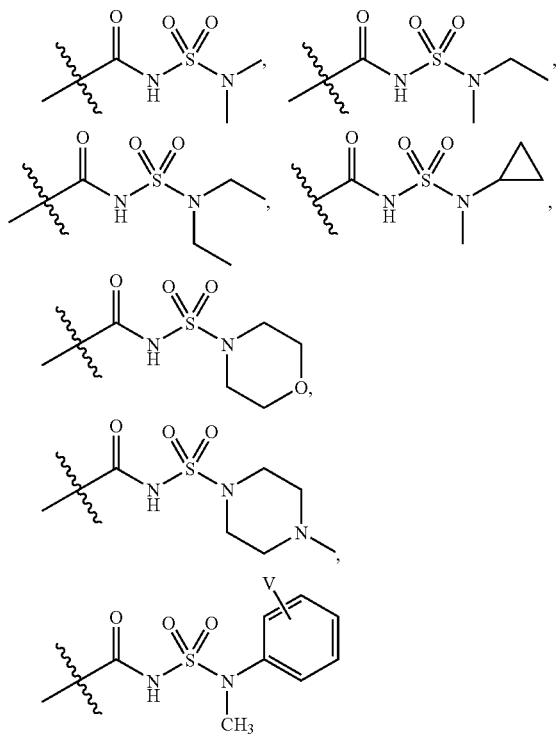

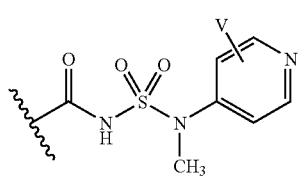

(where V is a halogen such as F, Cl, or Br; $C_1$-$C_6$ alkoxy such as $OCH_3$ or $OCH_2CH_3$; $C_1$-$C_6$ alkyl or $C_3$-$C_8$ cycloalkyl, such as $CH_3$, $CF_3$, or cyclopropyl; heteroatom substituted $C_1$-$C_6$ alkyl or $C_3$-$C_8$ cycloalkyl, such as $CH_2OCH_3$, or $CH_2OCH_2CH_3$; an electron withdrawing group such as CN, a ketone, an amide, or a sulfone), (and pyridyl isomers), or

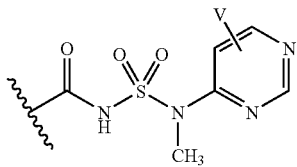

(and pyrimidine isomers).

In one embodiment, the compounds of Formula I for use in the methods of the invention have one or more of the following characteristics: an inhibition constant ($K_i$) with regard to H1 receptor binding of less than 500 nM; a $K_i$ with regard to off target binding to an off target selected from M1, M2, M3, D1, D2, α1 and α2 that is greater than 500 nM and/or more than 5 times greater than the $K_i$ with regard to the H1 receptor; a nonREM peak time value that is greater than 55% nonREM sleep per hour by the third hour after the compound is administered to a subject; a cumulative total increase in nonREM sleep of not less than 20 minutes for compound doses that produce maximum sleep consolidation; a longest sleep bout that is greater than 13 minutes in duration; net longest sleep bout post treatment is greater than or equal to 3 minutes when adjusted using a baseline value obtained at least 24 hours prior to administration of the compound to a subject; an average sleep bout that is greater than 5 minutes at absolute peak; administration of the compound to a subject does not produce appreciable amounts of rebound insomnia; administration of the compound to a subject does not appreciably inhibit REM sleep; and administration of the compound to a subject does not disproportionately inhibit locomotor activity relative to the normal effects of sleep.

In another embodiment, the compound of Formula I for use in the methods of the invention has one or more of the following characteristics: an inhibition constant ($K_i$) with regard to H1 receptor binding of less than 300 nM; a $K_i$ with regard to off target binding to an off target selected from M1, M2, M3, D1, D2, α1 and α2 that is greater than 1 μm; a nonREM peak time value that is greater than 55% nonREM sleep per hour by the third hour after the compound is administered to a subject; a cumulative total increase in nonREM sleep of not less than 20 minutes for compound doses that produce maximum sleep consolidation; a longest sleep bout that is greater than 13 minutes in duration; net longest sleep bout post treatment is greater than or equal to 3 minutes when adjusted using a baseline value obtained at least 24 hours prior to administration of the compound to a subject; an average sleep bout that is greater than 5 minutes at absolute peak; administration of the compound to a subject does not produce appreciable amounts of rebound insomnia; administration of the compound to a subject does not appreciably inhibit REM sleep; and administration of the compound to a subject does not disproportionately inhibit locomotor activity relative to the normal effects of sleep.

In another embodiment, the compound of Formula I for use in the methods of the invention has one or more of the following characteristics: an inhibition constant ($K_i$) with regard to H1 receptor binding of less than 150 nM; a $K_i$ with regard to off target binding to an off target selected from M1, M2, and M3, that is greater than 10 μM; a nonREM peak time value that is greater than 55% nonREM sleep per hour by the third hour after the compound is administered to a subject; a cumulative total increase in nonREM sleep not less than 20 minutes for compound doses that produce maximum sleep consolidation; a longest sleep bout that is greater than 17 minutes in duration; net longest sleep bout post treatment is greater than or equal to 5 minutes when adjusted using a baseline value obtained at least 24 hours prior to administration of the compound to a subject; an average sleep bout that is greater than 6 minutes at absolute peak; administration of the compound to a subject does not produce appreciable amounts of rebound insomnia; administration of the compound to a subject does not appreciably inhibit REM sleep; and administration of the compound to a subject does not disproportionately inhibit locomotor activity or motor tone relative to the normal effects of sleep.

In one embodiment, in the compound of Formula I used in the method of the invention, $R_6$ is not hydrogen or halogen. In another embodiment, in the compound used in the method of the invention, $R_6$ is methyl, methoxy, methoxymethylene ($CH_2OCH_3$), or hydroxy. In another embodiment, in the compound used in the method of the invention, $R_6$ is methyl, methoxy, methoxymethylene, fluoro, chloro, bromo or hydroxy.

In another embodiment, in the compound of Formula I used in the method of the invention, $R_1$-$R_5$ and $R_7$-$R_8$ are each hydrogen.

In another embodiment, in the compound of Formula I used in the method of the invention, at least one of $R_1$-$R_8$ is a non-hydrogen substituent and the remaining $R_1$-$R_8$ are hydrogen. In another embodiment, in the compound used in the method of the invention, at least one non-hydrogen $R_1$-$R_8$ is independently methyl, methoxy, methoxymethylene, fluoro, chloro, bromo, or hydroxy.

In another embodiment, in the compound of Formula I used in the method of the invention, at least two of $R_1$-$R_8$ are non-hydrogen substituents, and the remaining $R_1$-$R_8$ are hydrogen. In another embodiment, in the compound used in the method of the invention, at least 2 non-hydrogen $R_1$-$R_8$ are independently methyl, methoxy, methoxymethylene, fluoro, chloro, bromo, or hydroxy.

In another embodiment, in the compound of Formula I used in the method of the invention, at least three of $R_1$-$R_8$ are non-hydrogen substituents, and the remaining $R_1$-$R_8$ are hydrogen. In another embodiment, in the compound used in the method of the invention, at least 3 non-hydrogen $R_1$-$R_8$ are independently methyl, methoxy, methoxymethylene, fluoro, chloro, bromo, or hydroxy.

In another embodiment, in the compound of Formula I used in the method of the invention, $R_2$ is a non-hydrogen substituent. For example, $R_2$ is, e.g., methyl, methoxy, methoxymethylene, fluoro, chloro, bromo, or hydroxy.

In another embodiment, in the compound of Formula I used in the method of the invention, $R_3$ is a non-hydrogen substituent. For example, $R_3$ is, e.g., methoxy, methyl, methoxymethylene, fluoro, chloro, bromo, or hydroxy.

In another embodiment, in the compound of Formula I used in the method of the invention, $R_7$ is a non-hydrogen substituent. For example, $R_7$ is, e.g., methyl, methoxy, methoxymethylene, fluoro, chloro, bromo, or hydroxy.

In another embodiment, in the compound of Formula I used in the method of the invention, $R_2$ and $R_3$ are non-hydrogen substituents. For example, $R_2$ and $R_3$ are, e.g., independently, methyl, methoxy, methoxymethylene, fluoro, chloro, bromo, or hydroxy.

In another embodiment, in the compound of Formula I used in the method of the invention, $R_2$ and $R_6$ are non-hydrogen substituents. For example, $R_2$ and $R_6$ are, e.g., independently, methyl, methoxy, methoxymethylene, fluoro, chloro, bromo or hydroxy.

In another embodiment, in the compound of Formula I used in the method of the invention, $R_2$ and $R_7$ are non-hydrogen substituents. For example, $R_2$ and $R_7$ are, e.g., independently, methyl, methoxy, methoxymethylene, fluoro, chloro, bromo or hydroxy.

In another embodiment, in the compound of Formula I used in the method of the invention, $R_3$ and $R_6$ are non-hydrogen substituents. For example, $R_3$ and $R_6$ are, e.g., independently, methyl, methoxy, methoxymethylene, fluoro, chloro, bromo or hydroxy.

In another embodiment, in the compound of Formula I used in the method of the invention, $R_3$ and $R_7$ are non-hydrogen substituents. For example, $R_3$ and $R_7$ are, e.g., independently, methyl, methoxy, methoxymethylene, fluoro, chloro, bromo or hydroxy.

In another embodiment, in the compound of Formula I used in the method of the invention, $R_6$ and $R_7$ are non-hydrogen substituents. For example, $R_6$ and $R_7$ are, e.g., independently, methyl, methoxy, methoxymethylene, fluoro, chloro, bromo or hydroxy.

In another embodiment, in the compound of Formula I used in the method of the invention, $R_6$ is methoxy, and $R_1$-$R_5$ and $R_7$-$R_8$ are hydrogen.

In another embodiment, in the compound of Formula I used in the method of the invention, $R_2$ is methyl or methoxy, and $R_1$ and $R_3$-$R_8$ are hydrogen.

In another embodiment, in the compound of Formula I used in the method of the invention, $R_3$ is methyl and $R_1$-$R_2$ and $R_4$-$R_8$ are hydrogen.

In another embodiment, in the compound of Formula I used in the method of the invention, $R_7$ is methoxy and $R_1$-$R_6$ and $R_8$ are hydrogen.

In one embodiment, in the compound of Formula I used in the method of the invention, at least one of $R_2$, $R_6$, and $R_7$ is not hydrogen. In another embodiment, in the compound of Formula I used in the method of the invention, at least one of $R_2$, $R_6$, and $R_7$ is fluoro, methyl, or methoxy.

In one embodiment $R_9$ and $R_{10}$ together with the carbon to which they are attached are absent. In another embodiment, in the compound of Formula I used in the method of the invention, $R_{11}$ and $R_{12}$ are each methyl. In another embodiment, in the compound used in the method of the invention, $R_{11}$ and $R_{12}$ are each ethyl. In another embodiment, in the compound used in the method of the invention, $R_{11}$ and $R_{12}$, together with the carbon to which they are attached, are connected to form a spiro ring of size 3 to 7. The spiro ring is, e.g., a cyclopropyl ring.

In one embodiment, in the compound of Formula I used in the method of the invention, q is zero. In another embodiment, q is zero, and $R_9$ and $R_{10}$ together with the carbon to which they are attached are absent. In another embodiment, q is zero, $R_9$ and $R_{10}$ together with the carbon to which they are attached are absent, X and Y are absent. In another embodiment, q is zero, $R_9$ and $R_{10}$ together with the carbon to which they are attached are absent, X and Y are absent, and the sum of m, n, o, and p is 1 or 2.

In another embodiment, the compound of Formula I used in the method of the invention, is selected from Compounds 1-88. For example, the compound used in the methods of the invention is Compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, or 88.

In another embodiment, the compound used in the method of the invention, is Compound 1, 12, 13, 40, 61, 62, 63, 70, 71, 74, 75, 76, 77, 78, 79, 80, 81, 82, 83, or 84.

In one embodiment, the method of the invention is used to modulate sleep by administering a compound of Formula I, for example the method is used to decrease the time to sleep onset, increase the average sleep bout length, and/or increase the maximum sleep bout length. In another embodiment, the method of the invention is used to treat a sleep disorder by administering a compound of Formula I. The sleep disorder is, for example, circadian rhythm abnormality, insomnia, parasomnia (such as, e.g., somnambulism, pavor nocturnus, REM sleep behavior disorder, sleep bruxism and sleep enuresis), a sleep apnea disorder, such as, for example, central sleep apnea, obstructive sleep apnea and mixed sleep apnea, sleep apnea syndrome, narcolepsy or hypersomnia.

In one embodiment, the method of the invention is used to treat circadian rhythm abnormality. In another embodiment, the method of the invention is used to treat insomnia including, for example, extrinsic insomnia, psychophysiologic insomnia, altitude insomnia, restless leg syndrome, periodic limb movement disorder, medication-dependent insomnia, drug-dependent insomnia, alcohol-dependent insomnia, and insomnia associated with mental disorders. In another embodiment, the method of the invention is used to treat sleep apnea. In another embodiment, the method of the invention is used to treat narcolepsy. In another embodiment, the method of the invention is used to treat hypersomnia.

In one embodiment, in the method of the invention, the compound of Formula I, or pharmaceutically acceptable salt thereof, is administered as a pharmaceutical composition that includes a pharmaceutically acceptable excipient.

In another embodiment, in the method of the invention, the compound of Formula I or pharmaceutically acceptable salt thereof, is co-administered with one or more additional therapies.

In another embodiment, the subject treated by the method of the invention is selected from humans, companion animals, farm animals, laboratory animals, and wild animals. In one embodiment, the subject is a human.

In another aspect, the invention relates to a method of modulating sleep in a subject by administering to the subject a therapeutically effective amount of a compound of Formula II:

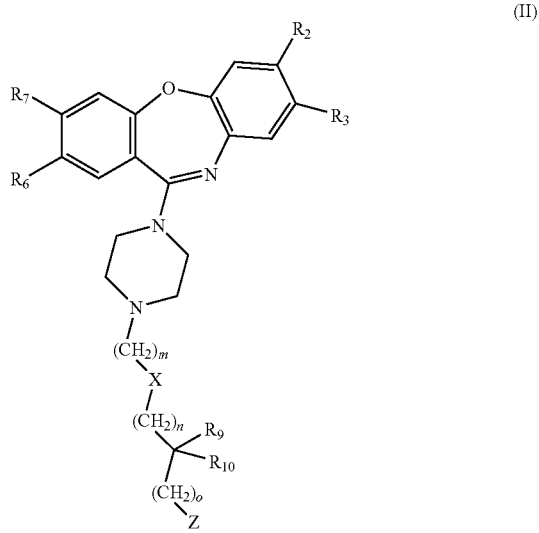

(II)

or a pharmaceutically effective salt thereof, wherein: m, n, and o are, independently, 0, 1, 2, 3, 4, 5, or 6, X is absent, O, S, C(O), SO, or $SO_2$; $R_2$, $R_3$, $R_6$, and $R_7$ are, independently, selected from H, F, Cl, Br, OH, $CF_3$, $CH_3$, $CH_2CH_3$, CH$(CH_3)_2$, cyclopropyl, $OCH_3$, $OCF_3$, $CH_2OCH_3$, and $CH_2OCH_2CH_3$; $R_9$ and $R_{10}$ are, independently, H, $C_1$-$C_6$ straight chain alkyl, $C_2$-$C_6$ branched alkyl, or $R_9$ and $R_{10}$ together with the carbon to which they are attached, are connected to form a spiro ring of size 3, 4, 5, 6, or 7 atoms; Z is COOH, $COOR_{13}$ (where $R_{13}$ is $C_1$-$C_6$ alkyl), $CONHS(O)_2$-alkyl, $CONHS(O)_2$-heteroalkyl, $CONHS(O)_2$-aryl, $CONHS(O)_2$-heteroaryl, $S(O)_2NHCO$-alkyl, $S(O)_2NHCO$-heteroalkyl, $S(O)_2NHCO$-aryl, $S(O)_2NHCO$-heteroaryl, $CONHS(O)_2NH$-alkyl; $CONHS(O)_2NH$-heteroalkyl; $CONHS(O)_2NH$-aryl; $CONHS(O)_2NH$-heteroaryl; or tetrazole, provided that when Z is COOH or $COOR_{13}$, and $R_6$ is H or halogen, $R_1$-$R_5$, and $R_7$-$R_{12}$ are not each hydrogen, further provided that when m is zero, X is absent.

In one embodiment, the compounds of Formula II for use in the methods of the invention have one or more of the following characteristics: an inhibition constant ($K_i$) with regard to H1 receptor binding of less than 500 nM; a $K_i$ with regard to off target binding to an off target selected from M1, M2, M3, D1, D2, α1 and α2 that is greater than 500 nM and/or more than 5 times greater than the $K_i$ with regard to the H1 receptor; a nonREM peak time value that is greater than 55% nonREM sleep per hour by the third hour after the compound is administered to a subject; a cumulative total increase in nonREM sleep of not less than 20 minutes for compound doses that produce maximum sleep consolidation; a longest sleep bout that is greater than 13 minutes in duration; net longest sleep bout post treatment is greater than or equal to 3 minutes when adjusted using a baseline value obtained at least 24 hours prior to administration of the compound to a subject; an average sleep bout that is greater than 5 minutes at absolute peak; administration of the compound to a subject does not produce appreciable amounts of rebound insomnia; administration of the compound to a subject does not appreciably inhibit REM sleep; and administration of the compound to a subject does not disproportionately inhibit locomotor activity relative to the normal effects of sleep.

In another embodiment, the compound of Formula II for use in the methods of the invention has one or more of the following characteristics: an inhibition constant ($K_i$) with regard to H1 receptor binding of less than 300 nM; a $K_i$ with regard to off target binding to an off target selected from M1, M2, M3, D1, D2, α1 and α2 that is greater than 1 μm; a nonREM peak time value that is greater than 55% nonREM sleep per hour by the third hour after the compound is administered to a subject; a cumulative total increase in nonREM sleep of not less than 20 minutes for compound doses that produce maximum sleep consolidation; a longest sleep bout that is greater than 13 minutes in duration; net longest sleep bout post treatment is greater than or equal to 3 minutes when adjusted using a baseline value obtained at least 24 hours prior to administration of the compound to a subject; an average sleep bout that is greater than 5 minutes at absolute peak; administration of the compound to a subject does not produce appreciable amounts of rebound insomnia; administration of the compound to a subject does not appreciably inhibit REM sleep; and administration of the compound to a subject does not disproportionately inhibit locomotor activity relative to the normal effects of sleep.

In another embodiment, the compound of Formula II for use in the methods of the invention has one or more of the following characteristics: an inhibition constant ($K_i$) with regard to H1 receptor binding of less than 150 nM; a $K_i$ with regard to off target binding to an off target selected from M1, M2, and M3, that is greater than 10 μM; a nonREM peak time value that is greater than 55% nonREM sleep per hour by the third hour after the compound is administered to a subject; a cumulative total increase in nonREM sleep not less than 20 minutes for compound doses that produce maximum sleep consolidation; a longest sleep bout that is greater than 17 minutes in duration; net longest sleep bout post treatment is greater than or equal to 5 minutes when adjusted using a baseline value obtained at least 24 hours prior to administration of the compound to a subject; an average sleep bout that is greater than 6 minutes at absolute peak; administration of the compound to a subject does not produce appreciable amounts of rebound insomnia; administration of the compound to a subject does not appreciably inhibit REM sleep; and administration of the compound to a subject does not disproportionately inhibit locomotor activity or motor tone relative to the normal effects of sleep.

In one embodiment, in the compound of Formula II used in the method of the invention, $R_6$ is not H, F, Cl, or Br. In another embodiment, in the compound of Formula II used in the method of the invention, $R_6$ is methyl, methoxy methoxymethylene, or hydroxy.

In another embodiment, in the compound of Formula II used in the method of the invention, $R_2$-$R_3$ and $R_7$ are each hydrogen. In another embodiment, in the compound of Formula II used in the method of the invention, $R_2$-$R_3$ and $R_6$-$R_7$ are independently hydrogen, methyl, methoxy, methoxymethylene, fluoro, chloro, bromo or hydroxy. In another embodiment, in the compound of Formula II used in the method of the invention, $R_2$ is a non-hydrogen substituent. In another embodiment, in the compound of Formula II used in the method of the invention, $R_3$ is a non-hydrogen substituent. In another embodiment, in the compound of Formula II used in the method of the invention, $R_6$ is a non-hydrogen substituent. In another embodiment, in the compound of Formula II used in the method of the invention, $R_7$ is a non-hydrogen substituent. In another embodiment, in the compound of Formula II used in the method of the invention, $R_2$ and $R_3$ are non-hydrogen substituents. In another embodiment, in the compound of Formula II used in the method of the invention, $R_2$ and $R_6$ are non-hydrogen substituents. In another embodiment, in the compound of Formula II used in the method of the invention, $R_2$ and $R_7$ are non-hydrogen substituents. In another embodiment, in the compound of Formula II used in the method of the invention, $R_3$ and $R_6$ are non-hydrogen substituents. In another embodiment, in the compound of Formula II used in the method of the invention, $R_3$ and $R_7$ are non-hydrogen substituents. In another embodiment, in the compound of Formula II used in the method of the invention, $R_6$ and $R_7$ are non-hydrogen substituents.

In another embodiment, in the compound of Formula II used in the method of the invention, $R_6$ is methoxy, and $R_2$, $R_3$, and $R_7$ are hydrogen.

In another embodiment, in the compound of Formula II used in the method of the invention, $R_2$ is methyl or methoxy, and $R_3$, $R_6$, and $R_7$ are hydrogen.

In another embodiment, in the compound of Formula II used in the method of the invention, $R_3$ is methyl and $R_2$, $R_6$, and $R_7$ are hydrogen.

In another embodiment, in the compound of Formula II used in the method of the invention, wherein $R_7$ is methoxy and $R_2$, $R_3$, and $R_6$ are hydrogen.

In another embodiment, in the compound of Formula II used in the method of the invention, $R_9$ and $R_{10}$ are each methyl. In another embodiment, in the compound of Formula II used in the method of the invention, $R_9$ and $R_{10}$ are each ethyl. In another embodiment, in the compound of Formula II used in the method of the invention, $R_9$ and $R_{10}$, together with the carbon to which they are attached, are connected to form a spiro ring of size 3 to 7. For example, the spiro ring is, e.g., a cyclopropyl ring.

In one embodiment, in the compound of Formula II used in the method of the invention, o is zero. In another embodiment, o is zero, and X is absent. In another embodiment, o is zero, X is absent, and the sum of m and n is 1 or 2.

In one embodiment, the method of the invention is used to modulate sleep by administering a compound of Formula II, for example the method is used to decrease the time to sleep onset, increase the average sleep bout length, and/or increase the maximum sleep bout length. In another embodiment, the method of the invention is used to treat a sleep disorder by administering a compound of Formula II. The sleep disorder is, for example, circadian rhythm abnormality, insomnia, parasomnia, sleep apnea syndrome, narcolepsy or hypersomnia.

In another aspect, the invention relates to a method of modulating sleep in a subject by administering to the subject a therapeutically effective amount of a compound of Formula III:

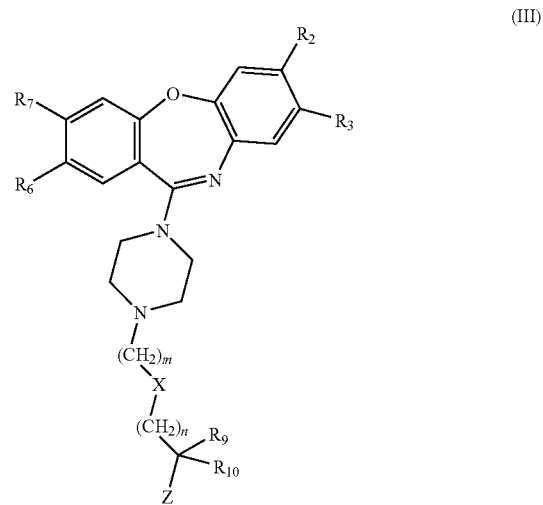

(III)

or a pharmaceutically effective salt thereof, wherein: m and n are, independently, 0, 1, 2, 3, or 4, X is absent, O, S, C(O), SO, or $SO_2$; $R_2$, $R_3$, $R_6$, and $R_7$ are, independently, select from H, F, Cl, Br, OH, $CF_3$, $CH_3$, $CH_2CH_3$, $CH(CH_3)_2$, $OCH_3$, $CH_2OCH_3$, and $CH_2OCH_2CH_3$; $R_9$ and $R_{10}$, are, independently, H, $C_1$-$C_6$ straight chain alkyl; $C_2$-$C_6$ branched alkyl, or $R_9$ and $R_{10}$, together with the carbon to which they are attached, are connected to form a spiro ring of size 3, 4, 5, 6, or 7 atoms; Z is selected from $CO_2H$, $CONHS(O)_2$-alkyl, $CONHS(O)_2$-cycloalkyl, $CONHS(O)_2$-heteroalkyl, CONHS$(O)_2$-aryl, $CONHS(O)_2$-heteroaryl, and tetrazole; provided that when Z is COOH and $R_6$ is H, F, Cl, or Br, $R_2$, $R_3$, $R_7$, and $R_9$-$R_{10}$ are not each hydrogen, further provided that when m is zero, X is absent.

In one embodiment, the compounds of Formula III for use in the methods of the invention have one or more of the following characteristics: an inhibition constant ($K_i$) with regard to H1 receptor binding of less than 500 nM; a $K_i$ with regard to off target binding to an off target selected from M1, M2, M3, D1, D2, α1 and α2 that is greater than 500 nM and/or more than 5 times greater than the $K_i$ with regard to the H1 receptor; a nonREM peak time value that is greater than 55% nonREM sleep per hour by the third hour after the compound is administered to a subject; a cumulative total increase in nonREM sleep of not less than 20 minutes for compound doses that produce maximum sleep consolidation; a longest sleep bout that is greater than 13 minutes in duration; net longest sleep bout post treatment is greater than or equal to 3 minutes when adjusted using a baseline value obtained at least 24 hours prior to administration of the compound to a subject; an average sleep bout that is greater than 5 minutes at absolute peak; administration of the compound to a subject does not produce appreciable amounts of rebound insomnia; administration of the compound to a subject does not appreciably inhibit REM sleep; and administration of the compound to a subject does not disproportionately inhibit locomotor activity relative to the normal effects of sleep.

In another embodiment, the compound of Formula III for use in the methods of the invention has one or more of the following characteristics: an inhibition constant ($K_i$) with regard to H1 receptor binding of less than 300 nM; a $K_i$ with regard to off target binding to an off target selected from M1, M2, M3, D1, D2, $\alpha 1$ and $\alpha 2$ that is greater than 1 μm; a nonREM peak time value that is greater than 55% nonREM sleep per hour by the third hour after the compound is administered to a subject; a cumulative total increase in nonREM sleep of not less than 20 minutes for compound doses that produce maximum sleep consolidation; a longest sleep bout that is greater than 13 minutes in duration; net longest sleep bout post treatment is greater than or equal to 3 minutes when adjusted using a baseline value obtained at least 24 hours prior to administration of the compound to a subject; an average sleep bout that is greater than 5 minutes at absolute peak; administration of the compound to a subject does not produce appreciable amounts of rebound insomnia; administration of the compound to a subject does not appreciably inhibit REM sleep; and administration of the compound to a subject does not disproportionately inhibit locomotor activity relative to the normal effects of sleep.

In another embodiment, the compound of Formula III for use in the methods of the invention has one or more of the following characteristics: an inhibition constant ($K_i$) with regard to H1 receptor binding of less than 150 nM; a $K_i$ with regard to off target binding to an off target selected from M1, M2, and M3, that is greater than 10 μM; a nonREM peak time value that is greater than 55% nonREM sleep per hour by the third hour after the compound is administered to a subject; a cumulative total increase in nonREM sleep not less than 20 minutes for compound doses that produce maximum sleep consolidation; a longest sleep bout that is greater than 17 minutes in duration; net longest sleep bout post treatment is greater than or equal to 5 minutes when adjusted using a baseline value obtained at least 24 hours prior to administration of the compound to a subject; an average sleep bout that is greater than 6 minutes at absolute peak; administration of the compound to a subject does not produce appreciable amounts of rebound insomnia; administration of the compound to a subject does not appreciably inhibit REM sleep; and administration of the compound to a subject does not disproportionately inhibit locomotor activity or motor tone relative to the normal effects of sleep.

In one embodiment, in the compound of Formula III used in the method of the invention, $R_6$ is not H, F, Cl, or Br. In another embodiment, in the compound of Formula III used in the method of the invention, $R_2$, $R_3$, and $R_7$ are hydrogen. In another embodiment, in the compound of Formula III used in the method of the invention, $R_2$, $R_3$, and $R_6$-$R_7$ are independently H, F, Cl, Br, methyl, methoxy, methoxymethylene or hydroxy. In another embodiment, in the compound of Formula III used in the method of the invention, $R_6$ is methoxy.

In another embodiment, in the compound of Formula III used in the method of the invention, $R_6$ is methoxy, and $R_2$, $R_3$, and $R_7$ are hydrogen.

In another embodiment, in the compound of Formula III used in the method of the invention, $R_2$ is methyl or methoxy, and $R_3$, $R_6$, and $R_7$ are hydrogen.

In another embodiment, in the compound of Formula III used in the method of the invention, $R_3$ is methyl and $R_2$, $R_6$, and $R_7$ are hydrogen.

In another embodiment, in the compound of Formula III used in the method of the invention, wherein $R_7$ is methoxy and $R_2$, $R_3$, and $R_6$ are hydrogen.

In another embodiment, in the compound of Formula III used in the method of the invention, $R_9$ and $R_{10}$ are each methyl. In another embodiment, in the compound of Formula III used in the method of the invention, $R_9$ and $R_{10}$, together with the carbon to which they are attached, are connected to form a spiro ring of size 3.

In one embodiment, in the compound of Formula III used in the method of the invention, X is absent. In another embodiment, X is absent, and the sum of m and n is 1 or 2.

In one embodiment, the method of the invention is used to modulate sleep by administering a compound of Formula III, for example the method is used to decrease the time to sleep onset, increase the average sleep bout length, and/or increase the maximum sleep bout length. In another embodiment, the method of the invention is used to treat a sleep disorder by administering a compound of Formula III. The sleep disorder is, for example, circadian rhythm abnormality, insomnia, parasomnia, sleep apnea syndrome, narcolepsy or hypersomnia.

In another aspect, the invention relates to a method of modulating sleep in a subject by administering to the subject a therapeutically effective amount of a compound of Formula IV:

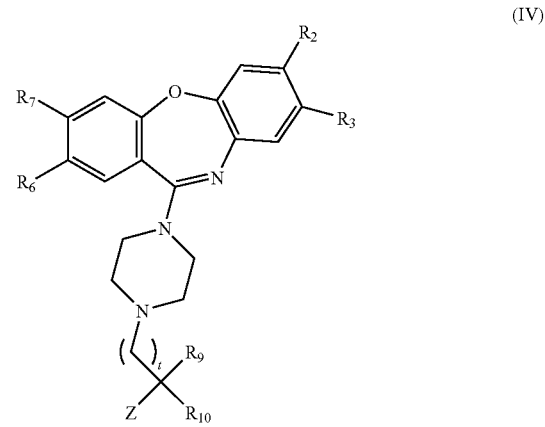

(IV)

or a pharmaceutically effective salt thereof, wherein: t is 1, 2, 3, or 4; $R_2$, $R_3$, $R_6$, and $R_7$ are, independently, H, F, Cl, Br, $CF_3$, $CH_3$, OH, $OCH_3$, $CH_2OCH_3$, or $CH_2OCH_2CH_3$; $R_9$-$R_{10}$ are H, $CH_3$, $CH_2CH_3$, or $R_9$ and $R_{10}$, together with the carbon to which they are attached are connected to form a spiro ring of size 3, 4, 5, 6, or 7 atoms; and Z is selected from $CO_2H$, $CONHS(O)_2$-alkyl, $CONHS(O)_2$-cycloalkyl, $CONHS(O)_2$-heteroalkyl, $CONHS(O)_2$-aryl, $CONHS(O)_2$-heteroaryl, or tetrazole; provided that when Z is COOH and $R_6$ is H, F, Cl, or Br, $R_2$, $R_3$, $R_7$, and $R_9$-$R_{10}$ are not each hydrogen.

In one embodiment, the compounds of Formula IV for use in the methods of the invention have one or more of the following characteristics: an inhibition constant ($K_i$) with regard to H1 receptor binding of less than 500 nM; a $K_i$ with regard to off target binding to an off target selected from M1, M2, M3, D1, D2, α1 and α2 that is greater than 500 nM and/or more than 5 times greater than the $K_i$ with regard to the H1 receptor; a nonREM peak time value that is greater than 55% nonREM sleep per hour by the third hour after the compound is administered to a subject; a cumulative total increase in nonREM sleep of not less than 20 minutes for compound doses that produce maximum sleep consolidation; a longest sleep bout that is greater than 13 minutes in duration; net longest sleep bout post treatment is greater than or equal to 3 minutes when adjusted using a baseline value obtained at least 24 hours prior to administration of the compound to a subject; an average sleep bout that is greater than 5 minutes at absolute peak; administration of the compound to a subject does not produce appreciable amounts of rebound insomnia; administration of the compound to a subject does not appreciably inhibit REM sleep; and administration of the compound to a subject does not disproportionately inhibit locomotor activity relative to the normal effects of sleep.

In another embodiment, the compound of Formula IV for use in the methods of the invention has one or more of the following characteristics: an inhibition constant ($K_i$) with regard to H1 receptor binding of less than 300 nM; a $K_i$ with regard to off target binding to an off target selected from M1, M2, M3, D1, D2, α1 and α2 that is greater than 1 μm; a nonREM peak time value that is greater than 55% nonREM sleep per hour by the third hour after the compound is administered to a subject; a cumulative total increase in nonREM sleep of not less than 20 minutes for compound doses that produce maximum sleep consolidation; a longest sleep bout that is greater than 13 minutes in duration; net longest sleep bout post treatment is greater than or equal to 3 minutes when adjusted using a baseline value obtained at least 24 hours prior to administration of the compound to a subject; an average sleep bout that is greater than 5 minutes at absolute peak; administration of the compound to a subject does not produce appreciable amounts of rebound insomnia; administration of the compound to a subject does not appreciably inhibit REM sleep; and administration of the compound to a subject does not disproportionately inhibit locomotor activity relative to the normal effects of sleep.

In another embodiment, the compound of Formula IV for use in the methods of the invention has one or more of the following characteristics: an inhibition constant ($K_i$) with regard to H1 receptor binding of less than 150 nM; a $K_i$ with regard to off target binding to an off target selected from M1, M2, and M3, that is greater than 10 μM; a nonREM peak time value that is greater than 55% nonREM sleep per hour by the third hour after the compound is administered to a subject; a cumulative total increase in nonREM sleep not less than 20 minutes for compound doses that produce maximum sleep consolidation; a longest sleep bout that is greater than 17 minutes in duration; net longest sleep bout post treatment is greater than or equal to 5 minutes when adjusted using a baseline value obtained at least 24 hours prior to administration of the compound to a subject; an average sleep bout that is greater than 6 minutes at absolute peak; administration of the compound to a subject does not produce appreciable amounts of rebound insomnia; administration of the compound to a subject does not appreciably inhibit REM sleep; and administration of the compound to a subject does not disproportionately inhibit locomotor activity or motor tone relative to the normal effects of sleep.

In one embodiment, in the compound of Formula IV used in the method of the invention, t is 1 or 2.

In one embodiment, the compound of Formula IV used in the method of the invention is selected from a compound of Formula IVa, IVb, IVc, IVd, and IVe.

In one embodiment, the method of the invention is used to modulate sleep by administering a compound of Formula IV, for example the method is used to decrease the time to sleep onset, increase the average sleep bout length, and/or increase the maximum sleep bout length. In another embodiment, the method of the invention is used to treat a sleep disorder by administering a compound of Formula IV. The sleep disorder is, for example, circadian rhythm abnormality, insomnia, parasomnia, sleep apnea syndrome, narcolepsy or hypersomnia.

In another aspect, the invention relates to a method of modulating sleep in a subject by administering to the subject a therapeutically effective amount of a compound of selected from Compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, or 88.

In another aspect, the invention relates to a compound of Formula I:

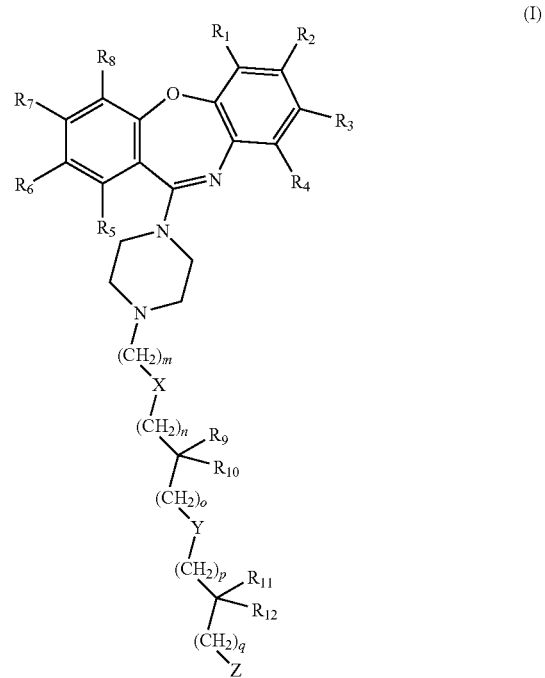

(I)

or a pharmaceutically effective salt thereof, wherein m, n, o, p, and q are, independently, an integer 0, 1, 2, 3, 4, 5, or 6; X and Y are, independently, absent, O, S, C(O), SO, or $SO_2$; $R_1$, $R_2$, $R_3$, $R_4$, $R_5$, $R_6$, $R_7$, and $R_8$ are independently selected from H, F, Cl, Br, OH, $CF_3$, $CH_3$, $C_2$-$C_6$ straight chain alkyl, $C_3$-$C_6$ branched alkyl, $C_3$-$C_7$ cycloalkyl, $C_3$-$C_7$ heterocyclyl, $OCH_3$, $OCF_3$, $CH_2OCH_3$, $CH_2CH_2OCH_3$, $CH_2OCH_2CH_3$, $C_1$-$C_6$ hydroxyalkyl, and $C_1$-$C_6$ alkoxy; any hydrogen in the $CH_2$ groups in the linker is optionally substituted with H, F, Cl, Br, OH, $CF_3$, $CH_3$, $C_2$-$C_6$ straight chain alkyl, $C_3$-$C_6$ branched alkyl, $C_3$-$C_7$ cycloalkyl, $C_3$-$C_7$ heterocyclyl, $OCH_3$, $OCF_3$, $CH_2OCH_3$, $CH_2CH_2OCH_3$, $CH_2OCH_2CH_3$, $C_1$-$C_6$ hydroxyalkyl, or $C_1$-$C_6$ alkoxy; $R_9$, $R_{10}$, $R_{11}$, and $R_{12}$ are, independently, H, $C_1$-$C_6$ straight chain alkyl, $C_2$-$C_6$ branched alkyl, or $R_9$ and $R_{10}$ together with the carbon to which they are attached are absent or are connected to form a spiro ring of size 3, 4, 5, 6, or 7 atoms, or $R_{11}$ and $R_{12}$ together with the carbon to which they are attached, are connected to form a spiro ring of size 3, 4, 5, 6, or 7 atoms, or substituents on two different carbon atoms are connected to form a ring of size 3, 4, 5, 6, or 7; Z is selected from $CO_2H$, $CO_2R_{13}$ (where $R_{13}$ is $C_1$-$C_6$ alkyl), $CONR_{14}R_{15}$ (where $R_{14}$ and $R_{15}$ are independently, hydrogen or lower alkyl), $CONHS(O)_2$-alkyl, $CONHS(O)_2$-cycloalkyl, $CONHS(O)_2$-heteroalkyl, $CONHS(O)_2$-aryl, $CONHS(O)_2$-heteroaryl, $S(O)_2NHCO$-alkyl, $S(O)_2NHCO$-cycloalkyl, $S(O)_2NHCO$-heteroalkyl, $S(O)_2NHCO$-aryl, $S(O)_2NHCO$-heteroaryl, $CONHS(O)_2NH$-alkyl, $CONHS(O)_2NH$-cycloalkyl, $CONHS(O)_2NH$-heteroalkyl, $CONHS(O)_2N$-aryl, $CONHS(O)_2NH$-heteroaryl, $SO_3H$, $SO_2H$, $S(O)NHCO$-alkyl, $S(O)NHCO$-aryl, $S(O)NHCO$-heteroaryl, $P(O)(OH)_2$, $P(O)OH$,

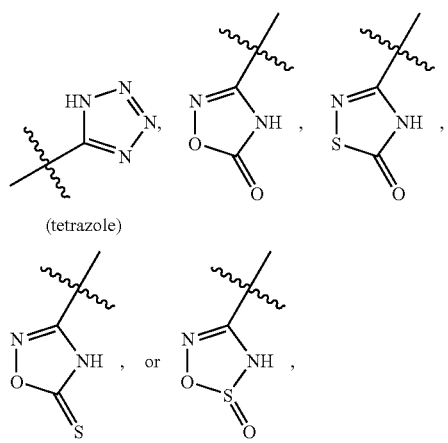

(tetrazole)

provided that when Z is COOH or $COOR_{13}$ and $R_6$ is H or halogen, $R_1$-$R_5$ and $R_7$-$R_{12}$ are not each hydrogen, further provided that when m is zero, X is absent.

In one embodiment, Z is a sulfonamide. Examples of sulfonamides include acyl sulfonamides. For example, Z can have the formula

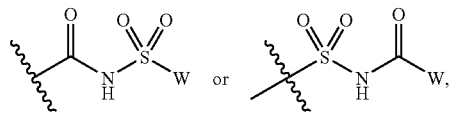

where W is a substituent chosen as needed to modulate the effects of the polar surface area of the Z moiety such that the desired level of oral absorption, CNS penetration, and rate of excretion into urine or bile is obtained. Examples of useful W substituents for this purpose include an alkyl group (optionally containing a double or triple bond or heteroatom substituted e.g., $CH_2CH_3$ or $CH_2OCH_2CH_3$), a cycloalkyl group (optionally containing a double bond), a heterocyclyl group, an aryl group, or a heteroaryl group, optionally substituted, such as those shown below:

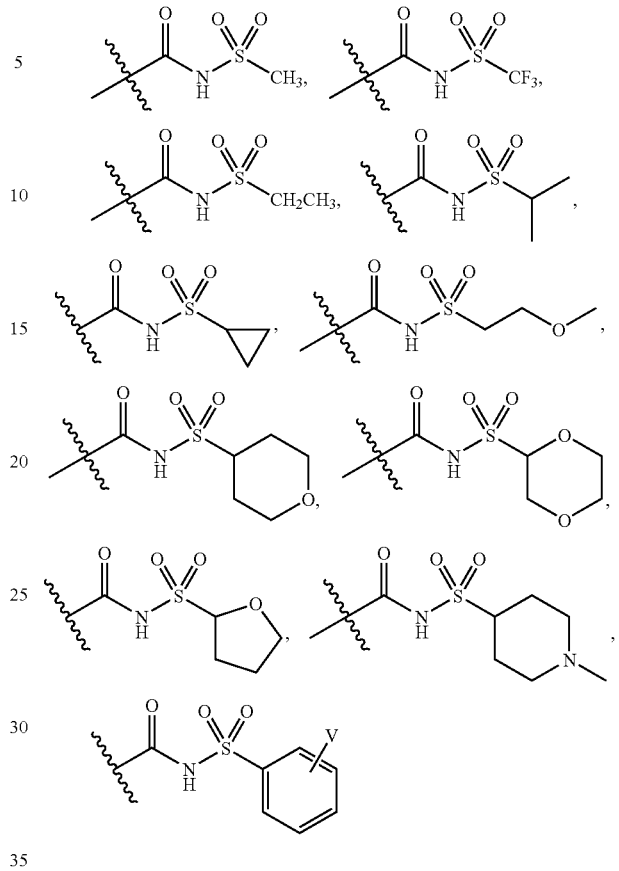

where V is one or more side chains selected to modulate the pKa of the acylsulfonamide moiety, or to affect the physical or metabolic properties of the compound. Examples of V side chains include halogens such as F, Cl, or Br; $C_1$-$C_6$ alkoxy groups such as $OCH_3$ or $OCH_2CH_3$; $C_1$-$C_6$ alkyl or $C_3$-$C_8$ cycloalkyl groups such as $CH_3$, $CF_3$, or cyclopropyl; heteroatom substituted $C_1$-$C_6$ alkyl or $C_3$-$C_8$ cycloalkyl, such as $CH_2OCH_3$, or $CH_2OCH_2CH_3$; electron withdrawing groups such as CN, a ketone, an amide, or a sulfone.

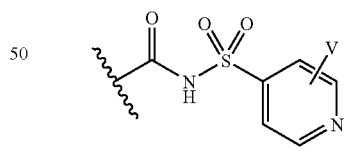

(and pyridyl isomers),

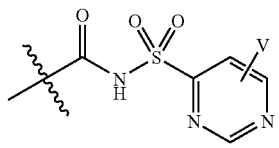

(and pyrimidine isomers), and

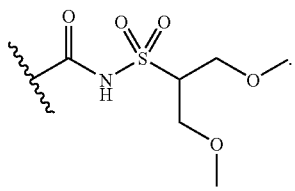

In one embodiment, Z is a sulfamide. Example sulfamides include acyl sulfamides. For example, Z can have the formula

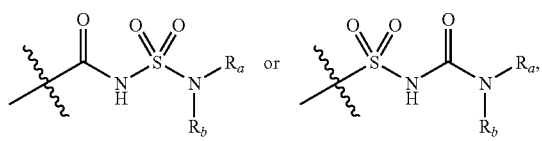

where $R_a$ and $R_b$ are, independently, for example an alkyl group, a cycloalkyl group, a heterocyclyl group, an aryl group, or a heteroaryl group, optionally substituted. Examples include the following:

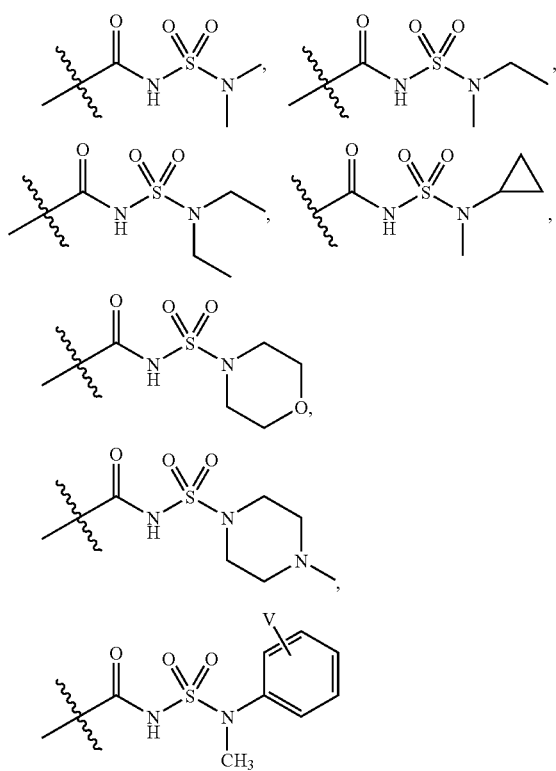

(where V is a halogen such as F, Cl, or Br; $C_1$-$C_6$ alkoxy such as $OCH_3$ or $OCH_2CH_3$; $C_1$-$C_6$ alkyl or $C_3$-$C_8$ cycloalkyl such as $CH_3$, $CF_3$, cyclopropyl; heteroatom substituted $C_1$-$C_6$ alkyl or $C_3$-$C_8$ cycloalkyl, such as $CH_2OCH_3$, or $CH_2OCH_2CH_3$; an electron withdrawing group such as CN, a ketone, an amide, or a sulfone),

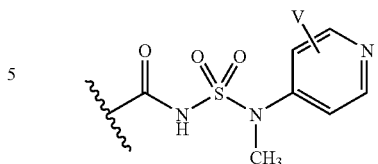

(and pyridyl isomers), or

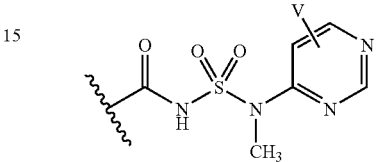

(and pyrimidine isomers).

In one embodiment, in the compound of Formula I, $R_6$ is not hydrogen or halogen. In another embodiment, in the compound of Formula I, $R_6$ is methyl, methoxy, methoxymethylene or hydroxy.

In another embodiment, in the compound of Formula I, $R_1$-$R_5$ and $R_7$-$R_8$ are each hydrogen.

In another embodiment, in the compound of Formula I, at least one of $R_1$-$R_8$ is a non-hydrogen substituent and the remaining $R_1$-$R_8$ are hydrogen. In another embodiment, at least one non-hydrogen $R_1$-$R_8$ is independently methyl, methoxy, methoxymethylene, fluoro, chloro, bromo, or hydroxy.

In another embodiment, in the compound of Formula I, at least two of $R_1$-$R_8$ are non-hydrogen substituents, and the remaining $R_1$-$R_8$ are hydrogen. In another embodiment, at least two non-hydrogen $R_1$-$R_8$ are independently methyl, methoxy, methoxymethylene, fluoro, chloro, bromo, or hydroxy.

In another embodiment, in the compound of Formula I, at least three of $R_1$-$R_8$ are non-hydrogen substituents, and the remaining $R_1$-$R_8$ are hydrogen. In another embodiment, at least three non-hydrogen $R_1$-$R_8$ are independently methyl, methoxy, methoxymethylene, fluoro, chloro, bromo, or hydroxy.

In another embodiment, in the compound of Formula I, $R_2$ is a non-hydrogen substituent. For example, $R_2$ is, e.g., methyl, methoxy, methoxymethylene, fluoro, chloro, bromo, or hydroxy. In another embodiment, in the compound of Formula I, $R_3$ is a non-hydrogen substituent. For example, $R_3$ is, e.g., methyl, methoxy, methoxymethylene, fluoro, chloro, bromo, or hydroxy. In another embodiment, in the compound of Formula I, $R_7$ is a non-hydrogen substituent. For example, $R_7$ is, e.g., methyl, methoxy, methoxymethylene, fluoro, chloro, bromo, or hydroxy. In another embodiment, in the compound of Formula I, $R_2$ and $R_3$ are non-hydrogen substituents. For example, $R_2$ and $R_3$ are, e.g., independently, methyl, methoxy, methoxymethylene, fluoro, chloro, bromo, or hydroxy. In another embodiment, in the compound of Formula I, $R_2$ and $R_6$ are non-hydrogen substituents. For example, $R_2$ and $R_6$ are, e.g., independently, methyl, methoxy, methoxymethylene, fluoro, chloro, bromo, or hydroxy. In another embodiment, in the compound of Formula I, $R_2$ and $R_7$ are non-hydrogen substituents. For example, $R_2$ and $R_7$ are, e.g., independently, methyl, methoxy, methoxymethylene, fluoro, chloro, bromo, or hydroxy. In another embodiment, in the compound of Formula I, $R_3$ and $R_6$ are non-hydrogen substituents. For example, $R_3$ and $R_6$ are, e.g., independently, methyl, methoxy, methoxymethylene, fluoro, chloro, bromo or hydroxy. In another embodiment, in the compound of Formula I, $R_3$ and $R_7$ are non-hydrogen substituents. For example, $R_3$ and $R_7$ are, e.g., independently, methyl, methoxy, methoxymethylene, fluoro, chloro, bromo or hydroxy. In another embodiment, in the compound of Formula I, $R_6$ and $R_7$ are non-hydrogen substituents. For example, $R_6$ and $R_7$ are, e.g., independently, methyl, methoxy, methoxymethylene, fluoro, chloro, bromo, or hydroxy. In another embodiment, in the compound of Formula I, $R_6$ is methoxy, and $R_1$-$R_5$ and $R_7$-$R_8$ are hydrogen. In another embodiment, in the compound of Formula I, $R_2$ is methyl or methoxy, and $R_1$ and $R_3$-$R_8$ are hydrogen. In another embodiment, in the compound of Formula I, $R_3$ is methyl and $R_1$-$R_2$ and $R_4$-$R_8$ are hydrogen. In another embodiment, in the compound of Formula I, $R_7$ is methoxy and $R_1$-$R_6$ and $R_8$ are hydrogen.

In one embodiment, at least one of $R_2$, $R_6$, and $R_7$ is not hydrogen. In another embodiment, at least one of $R_2$, $R_6$, and $R_7$ is fluoro, methyl, or methoxy.

In one embodiment, $R_9$ and $R_{10}$ together with the carbon to which they are attached are absent. In another embodiment, in the compound of Formula I, $R_{11}$ and $R_{12}$ are each methyl. In another embodiment, $R_{11}$ and $R_{12}$ are each ethyl. In another embodiment, $R_{11}$ and $R_{12}$, together with the carbon to which they are attached, are connected to form a spiro ring of size 3 to 7. The spiro ring is, e.g., a cyclopropyl ring.

In one embodiment, q is zero. In another embodiment, q is zero, and $R_9$ and $R_{10}$ together with the carbon to which they are attached are absent. In another embodiment, q is zero, $R_9$ and $R_{10}$ together with the carbon to which they are attached are absent, X and Y are absent. In another embodiment, q is zero, $R_9$ and $R_{10}$ together with the carbon to which they are attached are absent, X and Y are absent, and the sum of m, n, o, and p is 1 or 2.

In another embodiment, the compound of Formula I is selected from Compounds 1-88.

In another embodiment, the compound of Formula I is selected from Compounds 1, 12, 13, 40, 61, 62, 63, 70, 71, 74, 75, 76, 77, 78, 79, 80, 81, 82, 83, and 84.

In another aspect, the invention relates to a compound of Formula II:

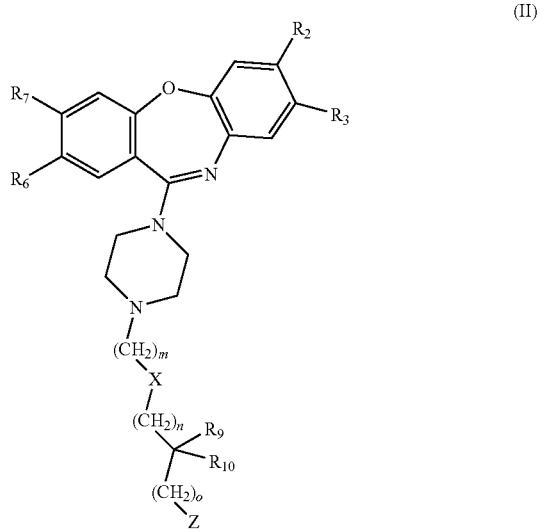

(II)

or a pharmaceutically effective salt thereof, wherein: m, n, and o are, independently, 0, 1, 2, 3, 4, 5, or 6, X is absent, O, S, C(O), SO, or $SO_2$; $R_2$, $R_3$, $R_6$, and $R_7$ are, independently H, F, Cl, Br, OH, $CF_3$, $CH_3$, $CH_2CH_3$, $CH(CH_3)_2$, cyclopropyl, $OCH_3$, $OCF_3$, $CH_2OCH_3$, or $CH_2OCH_2CH_3$; $R_9$, and $R_{10}$, are, independently, H, $C_1$-$C_6$ straight chain alkyl; $C_2$-$C_6$ branched alkyl, or $R_9$ and $R_{10}$ together with the carbon to which they are attached, are connected to form a spiro ring of size 3, 4, 5, 6, or 7 atoms; Z is COOH, $COOR_{13}$ (where $R_{13}$ is $C_1$-$C_6$ alkyl) $CONHS(O)_2$-alkyl, $CONHS(O)_2$-heteroalkyl, $CONHS(O)_2$-aryl, $CONHS(O)_2$-heteroaryl, $S(O)_2NHCO$-alkyl, $S(O)_2NHCO$-heteroalkyl, $S(O)_2NHCO$-aryl, $S(O)_2NHCO$-heteroaryl, $CONHS(O)_2NH$-alkyl; $CONHS(O)_2NH$-heteroalkyl; $CONHS(O)_2NH$-aryl; $CONHS(O)_2NH$-heteroaryl; or tetrazole, provided that when Z is COOH or $COOR_{13}$, and $R_6$ is H or halogen, $R_1$-$R_5$ and $R_7$-$R_{12}$ are not each hydrogen, further provided that when m is zero, X is absent.

In one embodiment, in the compound of Formula II, $R_6$ is not hydrogen or halogen. In another embodiment, in the compound of Formula II, $R_6$ is methyl, methoxy, methoxymethylene or hydroxy.

In another embodiment, in the compound of Formula II, $R_2$-$R_3$ and $R_7$ are each hydrogen.

In another embodiment, in the compound of Formula II, $R_2$-$R_3$ and $R_6$-$R_7$ are independently hydrogen, methyl, methoxy, methoxymethylene, fluoro, chloro, bromo, or hydroxy.

In another embodiment, in the compound of Formula II, $R_2$ is a non-hydrogen substituent. For example, $R_2$ is, e.g., methyl, methoxy, methoxymethylene, fluoro, chloro, bromo, or hydroxy. In another embodiment, in the compound of Formula II, $R_3$ is a non-hydrogen substituent. For example, $R_3$ is, e.g., methyl, methoxy, methoxymethylene, fluoro, chloro, bromo, or hydroxy. In another embodiment, in the compound of Formula II, $R_7$ is a non-hydrogen substituent. For example, $R_7$ is, e.g., methyl, methoxy, methoxymethylene, fluoro, chloro, bromo, or hydroxy. In another embodiment, in the compound of Formula II, $R_2$ and $R_3$ are non-hydrogen substituents. For example, $R_2$ and $R_3$ are, e.g., independently, methyl, methoxy, methoxymethylene, fluoro, chloro, bromo, or hydroxy. In another embodiment, in the compound of Formula II, $R_2$ and $R_6$ are non-hydrogen substituents. For example, $R_2$ and $R_6$ are, e.g., independently, methyl, methoxy, methoxymethylene, fluoro, chloro, bromo, or hydroxy. In another embodiment, in the compound of Formula II, $R_2$ and $R_7$ are non-hydrogen substituents. For example, $R_2$ and $R_7$ are, e.g., independently, methyl, methoxy, methoxymethylene, fluoro, chloro, bromo, or hydroxy. In another embodiment, in the compound of Formula II, $R_3$ and $R_6$ are non-hydrogen substituents. For example, $R_3$ and $R_6$ are, e.g., independently, methyl, methoxy, methoxymethylene, fluoro, chloro, bromo, or hydroxy. In another embodiment, in the compound of Formula II, $R_3$ and $R_7$ are non-hydrogen substituents. For example, $R_3$ and $R_7$ are, e.g., independently, methyl, methoxy, methoxymethylene, fluoro, chloro, bromo, or hydroxy. In another embodiment, in the compound of Formula II, $R_6$ and $R_7$ are non-hydrogen substituents. For example, $R_6$ and $R_7$ are, e.g., independently, methyl, methoxy, methoxymethylene, fluoro, chloro, bromo, or hydroxy. In another embodiment, in the compound of Formula II, $R_6$ is methoxy, and $R_2$, $R_3$, and $R_7$ are hydrogen. In another embodiment, in the compound of Formula II, $R_2$ is methyl or methoxy, and $R_3$, $R_6$, and $R_7$ are hydrogen. In another embodiment, in the compound of Formula II, $R_3$ is methyl and $R_2$, $R_6$, and $R_7$ are hydrogen. In another embodiment, in the compound of Formula II, $R_7$ is methoxy and $R_2$, $R_3$, and $R_6$ are hydrogen.

In another embodiment, in the compound of Formula II, $R_9$ and $R_{10}$ are each methyl. In another embodiment, $R_9$ and $R_{10}$ are each ethyl. In another embodiment, $R_9$ and $R_{10}$, together with the carbon to which they are attached, are connected to form a spiro ring of size 3 to 7. The spiro ring is, e.g., a cyclopropyl ring.

In one embodiment, in the compound of Formula II, o is zero. In another embodiment, o is zero, and X is absent. In another embodiment, o is zero, X is absent, and the sum of m and n is 1 or 2.

In another aspect, the invention relates to a compound of Formula III:

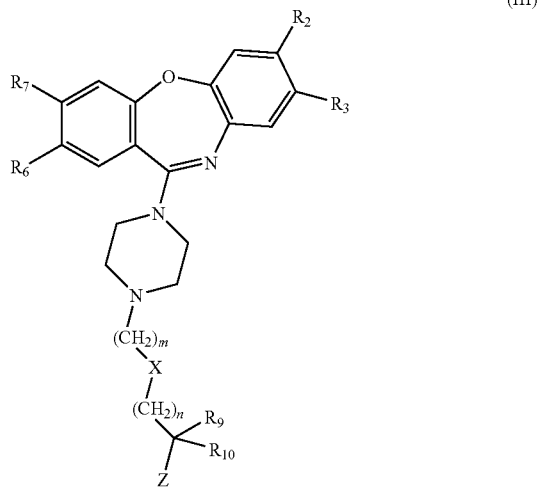

(III)

or a pharmaceutically effective salt thereof, wherein: m and n are, independently, 0, 1, 2, 3, or 4, X is absent, O, S, C(O), SO, or $SO_2$; $R_2$, $R_3$, $R_6$, and $R_7$ are, independently, selected from H, F, Cl, Br, OH, $CF_3$, $CH_3$, $CH_2CH_3$, $CH(CH_2)_2$, $OCH_3$, $CH_2OCH_3$, and $CH_2OCH_2CH_3$; $R_9$ and $R_{10}$, are, independently, H, $C_1$-$C_6$ straight chain alkyl; $C_2$-$C_6$ branched alkyl, or $R_9$ and $R_{10}$, together with the carbon to which they are attached, are connected to form a spiro ring of size 3, 4, 5, 6, or 7 atoms; Z is selected from $CO_2H$, $CONHS(O)_2$-alkyl, $CONHS(O)_2$-cycloalkyl, $CONHS(O)_2$-heteroalkyl, CONHS$(O)_2$-aryl, $CONHS(O)_2$-heteroaryl, and tetrazole; provided that when Z is COOH and $R_6$ is H, F, Cl, or Br, then $R_2$, $R_3$, $R_7$, and $R_9$-$R_{10}$ are not each hydrogen, further provided that when m is zero, X is absent.

In one embodiment, in the compound of Formula III, $R_6$ is not hydrogen or F, Cl, or Br.

In one embodiment, in the compound of Formula III, $R_6$ is not hydrogen or F, Cl, or Br and $R_2$, $R_3$, and $R_7$ are hydrogen.

In one embodiment, in the compound of Formula III, $R_2$, $R_3$, $R_6$, and $R_7$ are, independently, hydrogen, halogen, methyl, methoxymethylene, methoxy, or hydroxy.

In one embodiment, in the compound of Formula III, $R_6$ is methoxy. In another embodiment, in the compound of Formula III, $R_6$ is methoxy, and $R_2$, $R_3$, and $R_7$ are hydrogen. In another embodiment, in the compound of Formula III, $R_2$ is methyl or methoxy, and $R_3$, $R_6$ and $R_7$ are hydrogen. In another embodiment, in the compound of Formula III, $R_3$ is methyl and $R_2$, $R_6$ and $R_7$ are hydrogen. In another embodiment, in the compound of Formula III, $R_7$ is methoxy and $R_2$, $R_3$ and $R_6$ are hydrogen.

In another embodiment, in the compound of Formula III, $R_9$ and $R_{10}$ are each methyl. In another embodiment, $R_9$ and $R_{10}$, together with the carbon to which they are attached, are connected to form a spiro ring of size 3, e.g., a cyclopropyl ring.

In one embodiment, in the compound of Formula III, X is absent. In another embodiment, X is absent, and the sum of m and n is 1 or 2.

In another aspect, the invention relates to a compound of Formula IV:

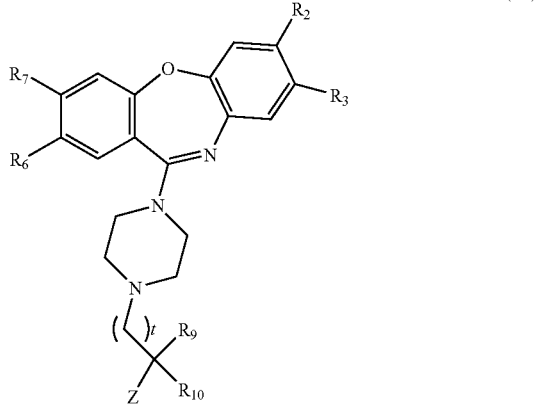

(IV)

or a pharmaceutically effective salt thereof, wherein: t is 1, 2, 3, or 4; $R_2$, $R_3$, $R_6$, and $R_7$ are, independently, H, F, Cl, Br, $CF_3$, $CH_3$, OH, $OCH_3$, $CH_2OCH_3$, or $CH_2OCH_2CH_3$; $R_9$-$R_{10}$ are H, $CH_3$, $CH_2CH_3$, or $R_9$ and $R_{10}$, together with the carbon to which they are attached, are connected to form a spiro ring of size 3, 4, 5, 6, or 7 atoms; and Z is selected from $CO_2H$, $CONHS(O)_2$-alkyl, $CONHS(O)_2$-cycloalkyl, $CONHS(O)_2$-heteroalkyl, and tetrazole; provided that when Z is COOH and $R_6$ is H, F, Cl, or Br, then $R_2$, $R_3$, $R_7$, and $R_9$-$R_{10}$ are not each hydrogen, further provided that when m is zero, X is absent.

In one embodiment, in the compound of Formula IV, t is 1 or 2.

In one embodiment, the compound of Formula IV is selected from a compound of formula IVa, IVb, IVc, IVd, or IVe.

In another aspect the invention relates to a compound selected from Compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, or 88.

In another aspect the invention relates to a compound selected from Compounds 1, 12, 13, 40, 61, 62, 63, 70, 71, 74, 75, 76, 77, 78, 79, 80, 81, 82, 83, and 84.

In one embodiment, the invention relates to a compound having the formula of Compound 1:

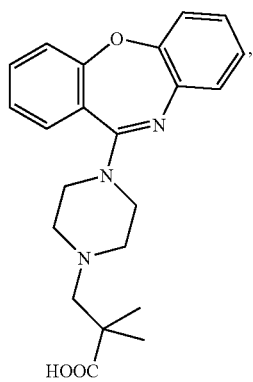

or a salt, solvate, hydrate, or prodrug thereof. For example, the invention relates to a solvate of Compound 1. In one embodiment, the invention relates to a hydrate of Compound 1. In another embodiment, the invention relates to a prodrug of Compound 1.

In another embodiment, the invention relates to a pharmaceutically acceptable salt of Compound 1. For example, the salt can be an acid addition salt, such as a hydrochloride salt.

In one aspect, the invention relates to the compound:

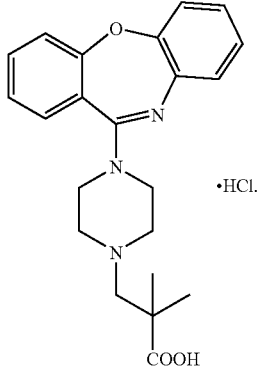

·HCl.

In another aspect, the invention relates to the compound:

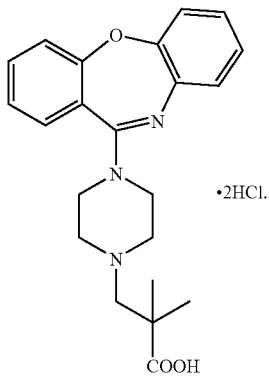

·2HCl.

In another aspect, the invention relates to a composition comprising Compound 1:

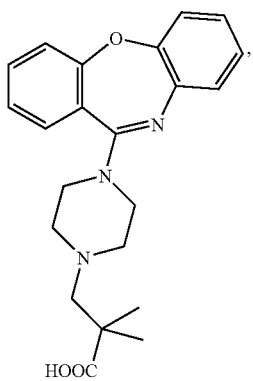

or a salt, solvate, hydrate, or prodrug thereof, and at least one pharmaceutically acceptable excipient. In one embodiment, the composition includes a solvate of Compound 1. In another embodiment, the composition includes a hydrate of Compound 1. In one embodiment, the composition includes a prodrug of Compound 1. In another embodiment, the composition includes a pharmaceutically acceptable salt of Compound 1. For example, the salt can be an acid addition salt. One embodiment of an acid addition salt is a hydrochloride salt.

In one embodiment, the invention relates to a composition of

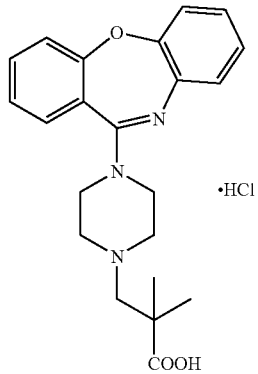

·HCl and at least one pharmaceutically acceptable excipient.

In another embodiment, the invention relates to a composition of

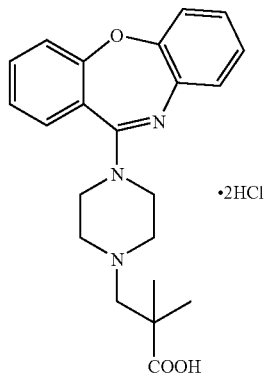

·2HCl and at least one pharmaceutically acceptable excipient.

In another aspect, the invention relates to a method of modulating sleep in a subject, by administering to a subject in need thereof a therapeutically effective amount of Compound 1:

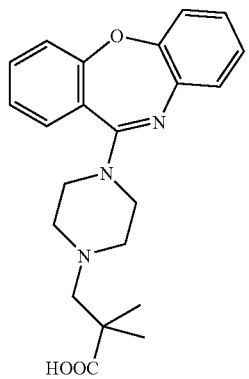

or a pharmaceutically acceptable salt, solvate, hydrate, or prodrug thereof. For example, the subject is a human. In one embodiment, the sleep modulation is selected from, for example, decreasing the time to sleep onset, increasing the average sleep bout length, and increasing the maximum sleep bout length. In one embodiment, the sleep modulation treats a sleep disorder. Examples of sleep disorders include circadian rhythm abnormality, insomnia, parasomnia, sleep apnea syndrome, narcolepsy and hypersomnia.

In another aspect, the invention relates to a method of modulating sleep in a subject, by administering to a subject in need thereof a therapeutically effective amount of Compound 1:

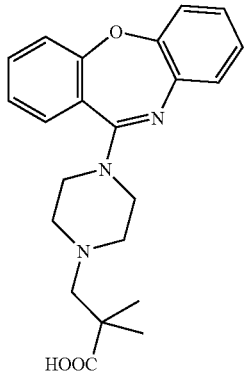

or a pharmaceutically acceptable salt, solvate, hydrate, or prodrug thereof as a pharmaceutical composition which includes at least one pharmaceutically acceptable excipient. For example, the subject is a human.

In one embodiment, Compound 1, or a pharmaceutically acceptable salt, solvate, hydrate, or prodrug thereof is co-administered with one or more additional therapies for modulating sleep in a subject. For example, the subject is a human.

The above description sets forth rather broadly the more important features of the present invention in order that the detailed description thereof that follows may be understood, and in order that the present contributions to the art may be better appreciated. Other objects and features of the present invention will become apparent from the following detailed description considered in conjunction with the examples.

DETAILED DESCRIPTION

The details of one or more embodiments of the invention are set forth in the accompanying description below. Although any methods and materials similar or equivalent to those described herein can be used in the practice or testing of the present invention, the methods and materials are now described. Other features, objects, and advantages of the invention will be apparent from the description. In the specification, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present specification will control.

Definitions

For convenience, certain terms used in the specification, examples and appended claims are collected here.

"Treating", includes any effect, e.g., lessening, reducing, modulating, or eliminating, that results in the improvement of the condition, disease, disorder, etc. "Treating", includes any effect, e.g., lessening, reducing, modulating, or eliminating, that results in the improvement of the condition, disease, disorder, etc. "Treating" or "treatment" of a disease state includes: (1) preventing the disease state, i.e., causing the clinical symptoms of the disease state not to develop in a subject that may be exposed to or predisposed to the disease state, but does not yet experience or display symptoms of the disease state; (2) inhibiting the disease state, i.e., arresting the development of the disease state or its clinical symptoms; or (3) relieving the disease state, i.e., causing temporary or permanent regression of the disease state or its clinical symptoms. "Disease state" means any disease, condition, symptom, or indication.

"Alkyl" includes saturated aliphatic groups, including straight-chain alkyl groups (e.g., methyl, ethyl, propyl, butyl, pentyl, hexyl, heptyl, octyl, nonyl, decyl), branched-chain alkyl groups (e.g., isopropyl, tert-butyl, isobutyl), cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. "Alkyl" further includes alkyl groups that have oxygen, nitrogen, sulfur or phosphorous atoms replacing one or more hydrocarbon backbone carbon atoms e.g., heteroatom substituted $CH_2OCH_3$ or $CH_2OCH_2CH_3$. In certain embodiments, a straight chain or branched chain alkyl has six or fewer carbon atoms in its backbone (e.g., $C_1$-$C_6$ for straight chain, $C_3$-$C_6$ for branched chain), and in other embodiments four or fewer carbon atoms. Likewise, cycloalkyls have from three to eight carbon atoms in their ring structure, and in other embodiments have five or six carbons in the ring structure. "$C_1$-$C_6$" includes alkyl groups containing 1, 2, 3, 4, 5, or 6 carbon atoms. "$C_2$-$C_6$" includes alkyl groups containing 2, 3, 4, 5, or 6 carbon atoms.

The term "alkyl" also includes both "unsubstituted alkyls" and "substituted alkyls", the latter of which refers to alkyl moieties having substituents replacing a hydrogen atom on one or more carbon atoms of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including —$NH_2$, alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)). "Alkyl" also includes the side chains of natural and unnatural amino acids.

"Aryl" includes groups with aromaticity, including 5- and 6-membered "unconjugated", or single-ring, aromatic groups that may include 0, 1, 2, 3, or 4 heteroatoms, as well as "conjugated" or multicyclic systems with at least one aromatic ring. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, alkyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl, and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl).

"Alkenyl" includes unsaturated aliphatic groups analogous in length and possible substitution to the alkyls described above, but that contain at least one double bond. For example, the term "alkenyl" includes straight-chain alkenyl groups (e.g., ethenyl, propenyl, butenyl, pentenyl, hexenyl, heptenyl, octenyl, nonenyl, and decenyl), branched-chain alkenyl groups, cycloalkenyl (e.g., alicyclic) groups (e.g., cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term "alkenyl" further includes alkenyl groups, which include oxygen, nitrogen, sulfur or phosphorous atoms replacing one or more hydrocarbon backbone carbons. In certain embodiments, a straight chain or branched chain alkenyl group has 1, 2, 3, 4, 5, or 6 carbon atoms in its backbone (e.g., $C_2$-$C_6$ for straight chain, $C_3$-$C_6$ for branched chain.) Likewise, cycloalkenyl groups may have 3, 4, 5, 6, 7, or 8 carbon atoms in their ring structure, and in another embodiment, have five or six carbons in the ring structure. The term "$C_2$-$C_6$" includes alkenyl groups containing 2, 3, 4, 5, or 6 carbon atoms.

The term "alkenyl" also includes both "unsubstituted alkenyls" and "substituted alkenyls", the latter of which refers to alkenyl moieties having substituents replacing a hydrogen on one or more hydrocarbon backbone carbon atoms. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including —$NH_2$, alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight-chain alkynyl groups (e.g., ethynyl, propynyl, butynyl, pentynyl, hexynyl, heptynyl, octynyl, nonynyl, decynyl), branched-chain alkynyl groups, and cycloalkyl or cycloalkenyl substituted alkynyl groups. The term "alkynyl" further includes alkynyl groups having oxygen, nitrogen, sulfur, or phosphorous atoms replacing one or more hydrocarbon backbone carbons. In certain embodiments, a straight chain or branched chain alkynyl group has 2, 3, 4, 5, or 6 carbon atoms in its backbone (e.g., $C_2$-$C_6$ for straight chain, $C_3$-$C_6$ for branched chain). The term "$C_2$-$C_6$" includes alkynyl groups containing 2, 3, 4, 5, or 6 carbon atoms.

The term "alkynyl" also includes both "unsubstituted alkynyls" and "substituted alkynyls", the latter of which refers to alkynyl moieties having substituents replacing a hydrogen on one or more hydrocarbon backbone carbon atoms. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including —$NH_2$, alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" includes an alkyl group, as defined above, but having 1, 2, 3, 4, 5, 6, 7, 8, 9, or 10 carbon atoms, in another embodiment, an alkyl group has 1, 2, 3, 4, 5, or 6 carbon atoms in its backbone structure. "Lower alkenyl" and "lower alkynyl" have chain lengths of, for example, 2, 3, 4, 5, or 6 carbon atoms.

"Acyl" includes compounds and moieties that contain the acyl radical ($CH_3CO$—) or a carbonyl group. "Substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including —$NH_2$, alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Acylamino" includes moieties wherein an acyl moiety is bonded to an amino group (—C(O)N— or —NC(O)—). For example, the term includes alkylcarbonylamino, arylcarbonylamino, carbamoyl and ureido groups.

"Aroyl" includes compounds and moieties with an aryl or heteroaromatic moiety bound to a carbonyl group. Examples of aroyl groups include phenylcarboxy, naphthyl carboxy, etc.

"Alkoxyalkyl", "alkylaminoalkyl" and "thioalkoxyalkyl" include alkyl groups, as described above, which further include oxygen, nitrogen or sulfur atoms replacing one or more hydrocarbon backbone carbon atoms e.g., $CH_3OCH_2$—, $CH_3NHCH_2$—, or $CH_3SCH_2$—.

The term "alkoxy" or "alkoxyl" includes substituted and unsubstituted alkyl, alkenyl, and alkynyl groups covalently linked to an oxygen atom. Examples of alkoxy groups (or alkoxyl radicals) include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including —NH$_2$, alkylamino, dialkylamino, arylamino, diarylamino, and alkylarylamino), acylamino (including alkylcarbonylamino, arylcarbonylamino, carbamoyl, and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, and trichloromethoxy.

The terms "heterocyclyl" or "heterocyclic" group include closed ring structures, e.g., 3, 4, 5, 6, 7, 8, 9, or 10-, or 4, 5, 6, or 7-membered rings, which include one or more heteroatoms. In one embodiment, the ring structure is a 5 or 6-membered ring. "Heteroatom" includes atoms of any element other than carbon or hydrogen. Examples of heteroatoms include nitrogen, oxygen, sulfur and phosphorus.

Heterocyclyl groups can be saturated or unsaturated and include for example, pyrrolidine, oxolane, thiolane, piperidine, piperazine, morpholine, lactones, lactams such as azetidinones and pyrrolidinones, sultams, and sultones. Heterocyclic groups e.g., pyrrole and furan can have aromatic character. Heterocyclic groups include fused ring structures such as quinoline and isoquinoline. Other examples of heterocyclic groups include pyridine and purine. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including —NH$_2$, alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. Heterocyclic groups can also be substituted at one or more constituent atoms with, for example, a lower alkyl, a lower alkenyl, a lower alkoxy, a lower alkylthio, a lower alkylamino, a lower alkylcarboxyl, a nitro, a hydroxyl, —CF$_3$, or —CN, or the like.

The term "thiocarbonyl" or "thiocarboxy" includes compounds and moieties which contain a carbon atom connected with a double bond to a sulfur atom

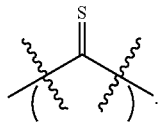

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or heteroatoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —O$^-$.

The term "halogen" includes fluorine, bromine, chlorine, iodine, etc. The term "perhalogenated" generally refers to a moiety wherein all hydrogens are replaced by halogen atoms.

The term "non-hydrogen substituent" refers to substituents other than hydrogen. Non-limiting examples include alkyl groups, alkoxy groups, halogen groups, hydroxyl groups, aryl groups, etc.

"Polycyclyl" or "polycyclic radical" refers to two or more cyclic rings (e.g., cycloalkyls, cycloalkenyls, cycloalkynyls, aryls and/or heterocyclyls) in which two or more carbons are common to adjoining rings. Rings that are joined through non-adjacent atoms are termed "bridged" rings. Each of the rings of the polycycle can be substituted with such substituents as described above, as for example, halogen, hydroxyl, alkyl, alkylcarbonyloxy, arylcarbonyloxy, alkoxycarbonyloxy, aryloxycarbonyloxy, carboxylate, alkylcarbonyl, alkoxycarbonyl, alkylaminocarbonyl, aralkylaminocarbonyl, alkenylaminocarbonyl, alkylcarbonyl, arylcarbonyl, aralkylcarbonyl, alkenylcarbonyl, aminocarbonyl, alkylthiocarbonyl, alkoxyl, phosphate, phosphonato, phosphinato, cyano, amino (including —NH$_2$, alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

An "anionic group," as used herein, refers to a group that is negatively charged at physiological pH. Anionic groups include carboxylate, sulfate, sulfonate, sulfinate, sulfamate, tetrazolyl, phosphate, phosphonate, phosphinate, or phosphorothioate or functional equivalents thereof. "Functional equivalents" of anionic groups are intended to include bioisosteres, e.g., bioisosteres of a carboxylate group. Bioisosteres encompass both classical bioisosteric equivalents and non-classical bioisosteric equivalents. Classical and non-classical bioisosteres are known in the art (see, e.g., Silverman, R. B. The Organic Chemistry of Drug Design and Drug Action, Academic Press, Inc.: San Diego, Calif., 1992, pp. 19-23). One example of an anionic group is a carboxylate.

"Protecting group" refers to a grouping of atoms that when attached to a reactive group in a molecule masks, reduces or prevents that reactivity. Examples of protecting groups can be found in Green and Wuts, *Protective Groups in Organic Chemistry*, (Wiley, 2$^{nd}$ ed. 1991); Harrison and Harrison et al., *Compendium of Synthetic Organic Methods*, Vols. 1-8 (John Wiley and Sons, 1971-1996); and Kocienski, *Protecting Groups*, (Verlag, 3$^{rd}$ ed. 2003).

The term "amine protecting group" is intended to mean a functional group that converts an amine, amide, or other nitrogen-containing moiety into a different chemical group that is substantially inert to the conditions of a particular chemical reaction. Amine protecting groups are preferably removed easily and selectively in good yield under conditions that do not affect other functional groups of the molecule. Examples of amine protecting groups include, but are not limited to, formyl, acetyl, benzyl, t-butyldimethylsilyl, t-butyldiphenylsilyl, t-butyloxycarbonyl (Boc), p-methoxybenzyl, methoxymethyl, tosyl, trifluoroacetyl, trimethylsilyl (TMS), fluorenyl-methyloxycarbonyl, 2-trimethylsilyl-ethyoxycarbonyl, 1-methyl-1-(4-biphenylyl)ethoxycarbonyl, allyloxycarbonyl, benzyloxycarbonyl (CBZ), 2-trimethylsilyl-ethanesulfonyl (SES), trityl and substituted trityl groups, 9-fluorenylmethyloxycarbonyl (FMOC), nitro-veratryloxycarbonyl (NVOC), and the like. Other suitable amine protecting groups are straightforwardly identified by those of skill in the art.

Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

"Stable compound" and "stable structure" are meant to indicate a compound that is sufficiently robust to survive isolation to a useful degree of purity from a reaction mixture, and formulation into an efficacious therapeutic agent.

In the present specification, the structural formula of the compound represents a certain isomer for convenience in some cases, but the present invention includes all isomers such as geometrical isomer, optical isomer based on an asymmetrical carbon, stereoisomer, tautomer and the like which occur structurally and an isomer mixture and is not limited to the description of the formula for convenience, and may be any one of isomer or a mixture. Therefore, an asymmetrical carbon atom may be present in the molecule and an optically active compound and a racemic compound may be present in the present compound, but the present invention is not limited to them and includes any one. In addition, a crystal polymorphism may be present but is not limiting, but any crystal form may be single or a crystal form mixture, or an anhydride or hydrate. Further, so-called metabolite which is produced by degradation of the present compound in vivo is included in the scope of the present invention.

It will be noted that the structure of some of the compounds of the invention include asymmetric (chiral) carbon atoms. It is to be understood accordingly that the isomers arising from such asymmetry are included within the scope of the invention, unless indicated otherwise. Such isomers can be obtained in substantially pure form by classical separation techniques and by stereochemically controlled synthesis. The compounds of this invention may exist in stereoisomeric form, therefore can be produced as individual stereoisomers or as mixtures.

"Isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

"Chiral isomer" means a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al, Angew. Chem. Inter. Edit. 1966, 5, 385; errata 511; Cahn et al., Angew. Chem. 1966, 78, 413; Cahn and Ingold, J. Chem. Soc. 1951 (London), 612; Cahn et al., Experientia 1956, 12, 81; Cahn, J., Chem. Educ. 1964, 41, 116).

"Geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Further, the structures and other compounds discussed in this application include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions. For example, using different solvents or different solvent mixtures for recrystallization; crystallization at different temperatures; various modes of cooling, ranging from very fast to very slow cooling during crystallization, and the like. Polymorphs are also obtained by heating or melting the disclosed compounds followed by gradual or fast cooling. The presence of polymorphs is determined by solid probe nuclear magnetic resonance spectroscopy, infrared spectroscopy, differential scanning calorimetry, powder X-ray diffraction, and other techniques known to one skilled in the art.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Tautomers" refers to compounds whose structures differ markedly in arrangement of atoms, but which exist in easy and rapid equilibrium. It is to be understood that compounds of Formulae I-IVe may be depicted as different tautomers. It should also be understood that when compounds have tautomeric forms, all tautomeric forms are intended to be within the scope of the invention, and the naming of the compounds does not exclude any tautomer form.

Some compounds of the present invention can exist in a tautomeric form which are also intended to be encompassed within the scope of the present invention.

The compounds, salts and prodrugs of the present invention can exist in several tautomeric forms, including the enol and imine form, and the keto and enamine form and geometric isomers and mixtures thereof. All such tautomeric forms are included within the scope of the present invention. Tautomers exist as mixtures of a tautomeric set in solution. In solid form, usually one tautomer predominates. Even though one tautomer may be described, the present invention includes all tautomers of the present compounds A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism, is exhibited by glucose. It arises as a result of the aldehyde group (—CHO) in a sugar chain molecule reacting with one of the hydroxy groups (—OH) in the same molecule to give it a cyclic (ring-shaped) form.

Tautomerizations are catalyzed by: Base: 1. deprotonation; 2. formation of a delocalized anion (e.g., an enolate); 3. protonation at a different position of the anion; Acid: 1. protonation; 2. formation of a delocalized cation; 3. deprotonation at a different position adjacent to the cation.

Common tautomeric pairs are: ketone-enol, amide-nitrile, lactam-lactim, amide-imidic acid tautomerism in heterocyclic rings (e.g., in the nucleobases guanine, thymine, and cytosine), amine-enamine and enamine-enamine. Examples include:

1)

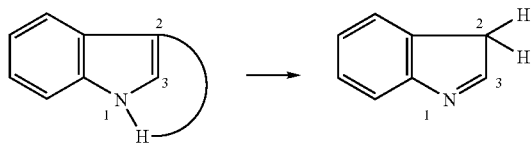

2)

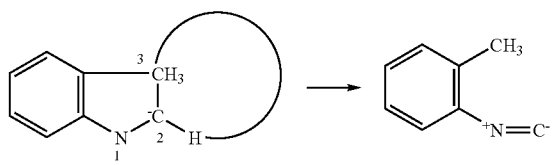

3)

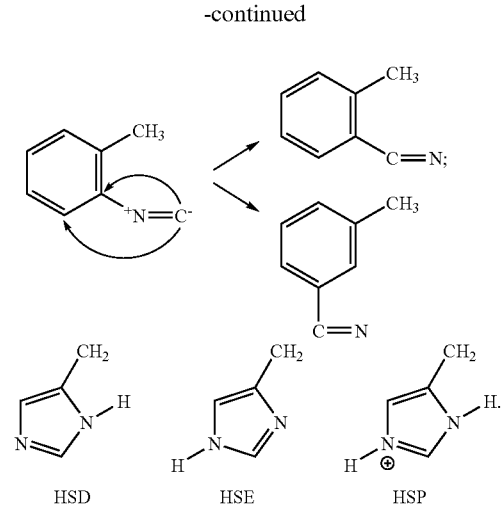

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As defined herein, the term "derivative", refers to compounds that have a common core structure, and are substituted with various groups as described herein. For example, all of the compounds represented by Formula I are loxapine derivatives, and have Formula I as a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include acyl sulfonimides, tetrazoles, sulfonates, and phosphonates. See, e.g., Patani and LaVoie, Chem. Rev. 96, 3147-3176 (1996). In some embodiments, Z is a carboxylic acid or a carboxylic acid bioisostere.

The language "loxapine-like compounds" or "loxapine-analog compounds" "loxapine-like compounds" or "loxapine derivative compounds" is intended to include analogs of loxapine or antihistamines that include two aryl groups linked to the same atom that are linked through a tricyclic ring system, e.g., a seven membered oxygen- and nitrogen-containing ring (i.e., similar to that of loxapine) bonded to position a piperazine ring.

The term "antihistamine" refers to a compound that binds to an H1 receptor and blocks the activity of histamine, and/or reduces the constitutive activity of the receptor.

As used herein, the term "sleep disorder" includes conditions recognized by one skilled in the art as sleep disorders, for example, conditions known in the art or conditions that are proposed to be sleep disorders or discovered to be sleep disorders. A sleep disorder also arises in a subject that has other medical disorders, diseases, or injuries, or in a subject being treated with other medications or medical treatments, where the subject, as a result, has difficulty falling asleep and/or remaining asleep, or experiences unrefreshing sleep or non-restorative sleep, e.g., the subject experiences sleep deprivation.

The term "treating a sleep disorder" also includes treating a sleep disorder component of other disorders, such as CNS disorders (e.g., mental or neurological disorders such as anxiety). Additionally, the term "treating a sleep disorder" includes the beneficial effect of ameliorating other symptoms associated with the disorder.

The term "nonREM peak sleep time" is defined as an absolute peak amount of nonREM sleep per hour post treatment, with drug administration occurring at Circadian Time (CT) 18, which is 6 hours after lights off in a nocturnal laboratory rat when housed in a LD 12:12 (12-hours light and 12 hours dark) light-dark cycle. The nominal criteria of 55% nonREM sleep per hour is equivalent to 33 minutes of nonREM sleep per hour.

As used herein, the term "cumulative nonREM sleep" is defined as the net total aggregate increase in the number of minutes of nonREM sleep, measured throughout the entire duration of a drug's soporific effect, which typically, but not always occurs in the first 6 hours post-treatment, adjusted for the net total aggregate number of minutes of nonREM sleep that occurred during the corresponding non-treatment baseline times of day recorded 24 hours earlier, relative to like vehicle control treatment.

As defined herein, the term "sleep bout" refers to a discrete episode of continuous or near continuous sleep, comprised of nonREM sleep, REM sleep, or both nonREM and REM sleep stages, delimited prior and after the episode by greater than two contiguous 10 second epochs of wakefulness.

As used herein, the term "longest sleep bout length" is defined as the total number of minutes an animal remains asleep (nonREM and/or REM sleep stages) during the single longest sleep episode or "bout" that occurred beginning in a given hour post-treatment. The "sleep bout length" measurement criteria assumes sleep is measured continuously in 10 second epochs, and is scored based upon the predominant state, computed or otherwise determined as a discrete sleep stage (where sleep stages are defined as nonREM sleep, REM sleep, or wakefulness) during the 10 second interval that defines the epoch.

The term "average sleep bout length" is defined as the average duration (in minutes) of every sleep bout that began in a given hour, independent of the individual duration of each episode or bout.

"Rebound insomnia" is defined as period of rebound, paradoxical, or compensatory wakefulness that occurs after the sleep promoting effects of a hypnotic or soporific agent.

"REM sleep inhibition" is defined as the reduction of REM sleep time post-treatment at CT-18 (6 hours after lights-off; LD 12:12) or at CT-5 (5 hours after lights-on; LD 12:12). Compounds that reduce REM sleep time by greater than 15 minutes (relative to baseline and adjusted for vehicle treatment) when administered at either CT-18 or CT-5 are considered unacceptable.

Compared with NREM sleep or wakefulness, REM sleep causes ventilatory depression and episodic cardiovascular changes. During rebound insomnia, the physiological effects of REM sleep are magnified and interrupt the normal sleep cycles.

As defined herein, "disproportionate locomotor activity inhibition" is a reduction of locomotor activity that exceeds the normal and expected reduction in behavioral activity attributable to sleep.

"Combination therapy" (or "co-therapy") includes the administration of a compound of the invention and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Combinations of the compounds of the present invention and the other active agents may be administered together in a single combination or separately. Where separate administration is employed, the administration of one element may be prior to, concurrent with, or subsequent to the administration of other agents. Administration of these therapeutic agents in combination typically is carried out over a defined time period (usually minutes, hours, days or weeks depending upon the combination selected). In one embodiment, "combination therapy" encompasses the administration of two or more of these therapeutic agents as part of separate monotherapy regimens that incidentally and arbitrarily result in the combinations of the present invention. In another embodiment, "combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues.

The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. "Combination therapy" also embraces the administration of the therapeutic agents as described above in further combination with other biologically active ingredients and non-drug therapies (e.g., surgery, radiation treatment, or a medical device). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The terms "parenteral administration" and "administered parenterally" as used herein refer to modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The term "pulmonary" as used herein refers to any part, tissue or organ whose primary function is gas exchange with the external environment, e.g., $O_2/CO_2$ exchange, within a patient. "Pulmonary" typically refers to the tissues of the respiratory tract. Thus, the phrase "pulmonary administration" refers to administering the formulations described herein to any part, tissue or organ whose primary function is gas exchange with the external environment (e.g., mouth, nose, pharynx, oropharynx, laryngopharynx, larynx, trachea, carina, bronchi, bronchioles, alveoli). For purposes of the present invention, "pulmonary" also includes a tissue or cavity that is contingent to the respiratory tract, in particular, the sinuses.

viaA "pharmaceutical composition" is a formulation containing the disclosed compounds in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" is defined as a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

A "subject" includes mammals, e.g., humans, companion animals (e.g., dogs, cats, birds, and the like), farm animals (e.g., cows, sheep, pigs, horses, fowl, and the like) and laboratory animals (e.g., rats, mice, guinea pigs, birds, and the like). Most preferably, the subject is human.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

The compounds of the invention are capable of further forming salts. All of these forms are also contemplated within the scope of the claimed invention.

"Pharmaceutically acceptable salt" of a compound means a salt that is pharmaceutically acceptable and that possesses the desired pharmacological activity of the parent compound.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabanic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates) or crystal forms (polymorphs) as defined herein, of the same salt.

The pharmaceutically acceptable salts of the present invention can be formed from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are used. For example, the scheme below shows the formation of a pharmaceutically acceptable hydrochloric salt of the parent compound, Compound 1, upon treatment with hydrochloric acid.

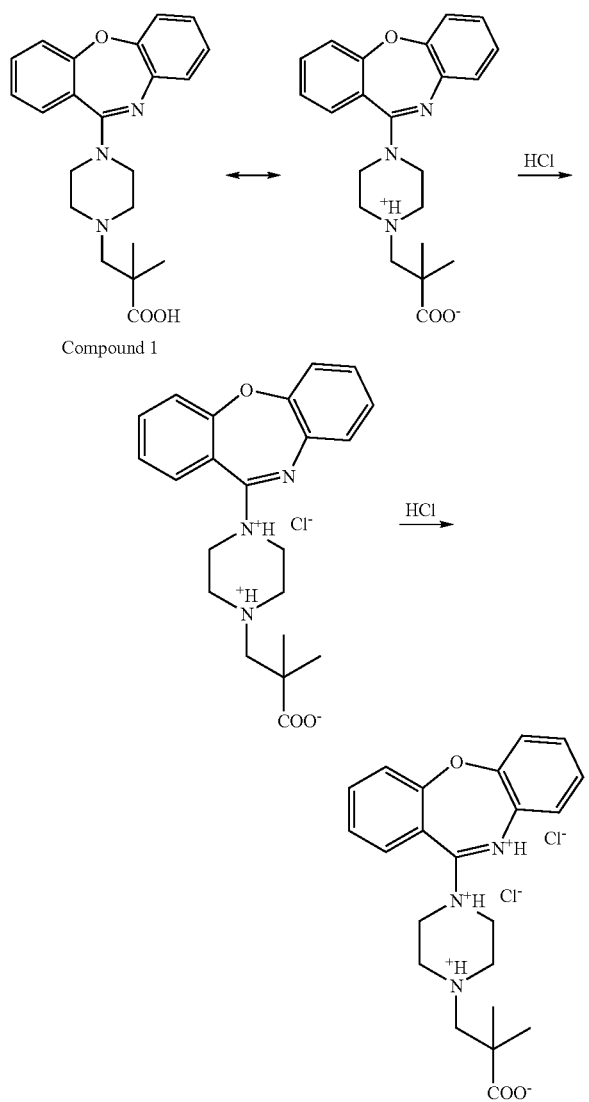

Compound 1

The number of atoms protonated and counterions associated with the salt can be controlled and depends on the number of acidic/basic atoms in the parent compound and amount of acid which is used to treat the parent compound. In one embodiment of the invention, the monohydrochloride salt of the parent compound is formed upon treatment with hydrochloric acid. In another embodiment, the dihydrochloride salt of the parent compound is formed upon treatment with hydrochloric acid.

Lists of suitable salts are found in *Remington's Pharmaceutical Sciences,* 18th ed. (Mack Publishing Company, 1990). For example, salts can include, but are not limited to, the hydrochloride and acetate salts of the aliphatic amine-containing, hydroxyl amine-containing, and imine-containing compounds of the present invention.

The compounds of the present invention can also be prepared as esters, for example pharmaceutically acceptable esters. For example a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds of the present invention can also be prepared as prodrugs, for example pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.) the compounds of the present invention can be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, sulfhydryl, carboxy, or carbonyl group is bonded to any group that, may be cleaved in vivo to form a free hydroxyl, free amino, free sulthydryl, free carboxy or free carbonyl group, respectively.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, esters groups (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of Formulae I-IVe, and the like, See Bundegaard, H. "Design of Prodrugs" p1-92, Elesevier, New York-Oxford (1985).

In the specification, the singular forms also include the plural, unless the context clearly dictates otherwise. Unless defined otherwise, all technical and scientific terms used herein have the same meaning as commonly understood by one of ordinary skill in the art to which this invention belongs. In the case of conflict, the present specification will control.

All percentages and ratios used herein, unless otherwise indicated, are by weight.

An "effective amount" of a compound of the disclosed invention is the quantity which, when administered to a subject having a disease or disorder, results in regression of the disease or disorder in the subject. The amount of the disclosed compound to be administered to a subject will depend on the particular disorder, the mode of administration, co-administered compounds, if any, and the characteristics of the subject, such as general health, other diseases, age, sex, genotype, body weight and tolerance to drugs. The skilled artisan will be able to determine appropriate dosages depending on these and other factors.

As used herein, the term "effective amount" refers to an amount of a compound, or a combination of compounds, of the present invention effective when administered alone or in combination as a sleep promoting agent. For example, an effective amount refers to an amount of the compound present in a formulation or on a medical device given to a recipient patient or subject sufficient to elicit biological activity. The combination of compounds optionally is a synergistic combination. Synergy, as described, for example, by Chou and Talalay, *Adv. Enzyme Regul.* vol. 22, pp. 27-55 (1984), occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, or increased sleep-promoting effect, lesser hangover effect, or some other beneficial effect of the combination compared with the individual components "A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

"Pharmacological effect" as used herein encompasses effects produced in the subject that achieve the intended purpose of a therapy. In one embodiment, a pharmacological effect means that primary indications of the subject being treated are prevented, alleviated, or reduced. For example, a pharmacological effect would be one that results in the prevention, alleviation or reduction of primary indications in a treated subject. In another embodiment, a pharmacological effect means that disorders or symptoms of the primary indications of the subject being treated are prevented, alleviated, or reduced. For example, a pharmacological effect would be one that results in the prevention or reduction of primary indications in a treated subject.

The invention provides a method of modulating sleep by administering an effective amount of a loxapine analog of the invention, which is a moiety that antagonizes a histamine receptor or a collection of histamine receptors. The invention also relates to novel loxapine analogs.

Effective sleep modulators have certain characteristics that correspond with increased efficacy and decreased side effects. These characteristics include a desired half-life in a subject, controlled onset of desired sedative effects, and minimal to no detectable effect on psychomotor or other central nervous system (CNS) side effects (e.g., memory deficits, decreased muscle tone, drooping eyelids or drowsiness). For example, effective sleep modulators have a half life in humans of less than 7 hours, less than 6 hours, less than 5 hours, less than 4 hours, approximately 3 hours, or in the range of 3 to 7 hours.

One approach to developing an effective sleep modulator is strategically derivitizing a known compound or family of compounds with sleep modulating activity. Derivitization of a known compound may enhance one or more biological properties to allow the resulting compound to perform in an improved manner. Examples of favorable biological properties include, but are not limited, to induction of a discrete sleep or hypnotic state, activity of the therapeutic compound for a discrete period of time, penetration through the blood brain barrier into the CNS, e.g., resulting from lipophilicity of substituents or conformational lipophilicity (i.e., lipophilicity as a result of a particular conformation, such as internal salt formation between a carboxylate anion and a protonated amine), modulation of the half-life of the therapeutic compound, an alteration of charge, an alteration of pharmacokinetics, an alteration of log P by a value of one or more, increased receptor selectivity, reduced peripheral half-life, the ability to increase dosage, increased peripheral elimination, decreased anti-muscarinic activity, decreased anti-cholinergic, and any combination thereof.

Derivitization of a compound results in a variety of effects and can alter the mechanism of action. For example, in some circumstances, a compound containing a particular functional group, such as, e.g., an ester, carboxylic acid, or alcohol group, possesses an improved selectivity for a desired receptor versus undesired receptors when compared with a compound without this group. In other circumstances, the compound containing the particular functional group is more active as a therapeutic agent for treating sleep disorders than the corresponding compound without this group. The effect of the derivitized compound depends on the identity of the addition.

By derivitizing a compound in order to enhance favorable biological properties and decrease undesirable side effects, it is possible to implement a strategy based on potential mechanistic effects or interactions. For example, in some compounds, the presence of a carboxylic acid results in the ability to form an intramolecular ionic bond that includes the corresponding carboxylate ion, e.g., zwitterion species formation with a nitrogen atom within the compound or salt bridge formation. These interactions result in favorable biological effects such as conformational lipophilicity, i.e., increased lipophilicity as a result of a particular conformation, such as internal salt formation between a carboxylate anion and a protonated amine. Such conformational lipophilicity allows penetration through the blood brain barrier into the CNS, despite that the presence of two polar ions is generally thought to inhibit crossing of the non-polar blood-brain barrier. Another benefit of the presence of the carboxylic acid is an improved ability of the compound to bind selectively to the desired receptor.

Compounds of the invention can also be derivitized to produce prodrugs. "Prodrug" includes a precursor form of the drug which is metabolically converted in vivo to produce the active drug. The invention further contemplates the use of prodrugs which are converted in vivo to the sleep modulating compounds used in the methods of the invention (see, e.g., R. B. Silverman, 1992, "The Organic Chemistry of Drug Design and Drug Action", Academic Press, Chp. 8). Such prodrugs can be used to alter the biodistribution (e.g., to allow compounds which would not typically cross the blood-brain barrier to cross the blood-brain barrier) or the pharmacokinetics of the sleep modulating compound. For example, an anionic group, e.g., a carboxylate, sulfate or sulfonate, can be esterified, e.g., with an alkyl group (e.g., a methyl group) or a phenyl group to yield an ester. When the ester is administered to a subject, the ester is cleaved, enzymatically or non-enzymatically, reductively or hydrolytically, to reveal the anionic group. Such an ester can be cyclic, e.g., a cyclic sulfate or sulfone, or two or more anionic moieties may be esterified through a linking group. An anionic group can be esterified with moieties (e.g., acyloxymethyl esters) which are cleaved to reveal an intermediate sleep modulating compound which subsequently decomposes to yield the active sleep modulating compound. In one embodiment, the prodrug is a reduced form of a carboxylate, sulfate or sulfonate, e.g., an alcohol or thiol, which is oxidized in vivo to the sleep modulating compound. Furthermore, an anionic moiety can be esterified to a group which is actively transported in vivo, or which is selectively taken up by target organs.

This strategy is applied to sleep modulating compounds to improve their effectiveness and safety in clinical use. One group of compounds useful in modulating sleep is related to loxapine, which is a psychotherapeutic agent belonging to the family of compounds commonly known as tricyclic antidepressants ("TCAs"). Loxapine is a dibenzoxazepine antipsychotic agent, which produces pharmacological responses in various animal species which are characteristic of those seen with the majority of antipsychotic drugs. Although the precise mechanism of action is not known, loxapine succinate administration results in strong inhibition of spontaneous motor activity. Loxapine is recommended for treating schizophrenia.

In one aspect, the invention provides a method of modulating sleep in a subject by administering a therapeutically effective amount of a compound having the Formula I:

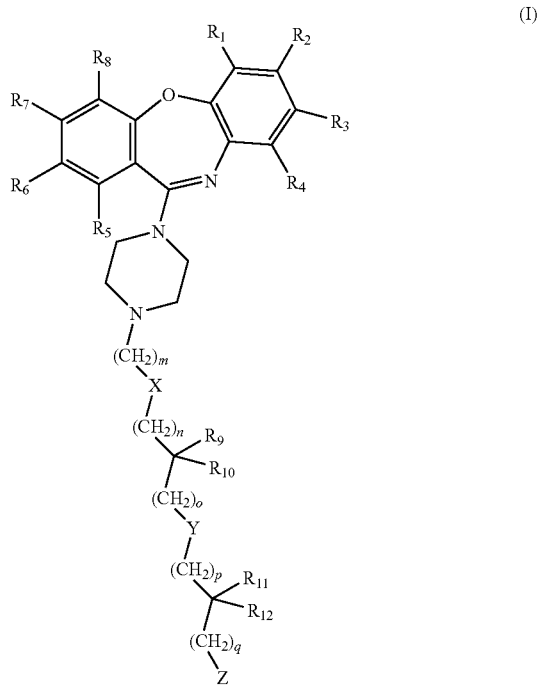

(I)

Z is selected from $CO_2H$, $CO_2R_{13}$, where $R_{13}$ is $C_1$-$C_6$ alkyl, $CONR_{14}R_{15}$, where $R_{14}$ and $R_{15}$ are, independently, hydrogen or lower alkyl, $CONHS(O)_2$-alkyl, $CONHS(O)_2$-cycloalkyl, $CONHS(O)_2$-heteroalkyl, $CONHS(O)_2$-aryl, $CONHS(O)_2$-heteroaryl, $S(O)_2NHCO$-alkyl, $S(O)_2NHCO$-cycloalkyl, $S(O)_2NHCO$-heteroalkyl, $S(O)_2NHCO$-aryl, $S(O)_2NHCO$-heteroaryl, $CONHS(O)_2NH$-alkyl, $CONHS(O)_2NH$-cycloalkyl, $CONHS(O)_2NH$-heteroalkyl, $CONHS(O)_2NH$-aryl, $CONHS(O)_2NH$-heteroaryl, $SO_3H$, $SO_2H$, $S(O)NHCO$-alkyl, $S(O)NHCO$-aryl, $S(O)NHCO$-heteroaryl, $P(O)(OH)_2$, $P(O)OH$,

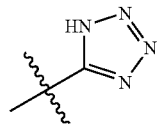

(tetrazole), or

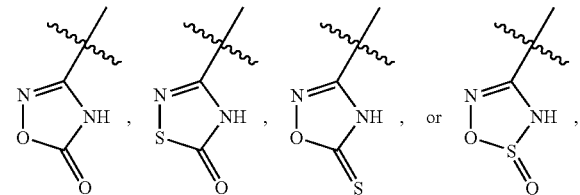

provided that when Z is COOH or $COOR_{13}$, and $R_6$ is H or halogen, $R_1$-$R_5$ and $R_7$-$R_{12}$ are not each hydrogen, further provided that when m is zero, X is absent.

In one embodiment, the compounds of Formula I for use in the methods of the invention have one or more of the following characteristics: an inhibition constant ($K_i$) with regard to H1 receptor binding of less than 500 nM; a $K_t$ with regard to off target binding to an off target selected from M1, M2, M3, D1, D2, $\alpha 1$ and $\alpha 2$ that is greater than 500 nM and/or more than 5 times greater than the $K_i$ with regard to the H1 receptor; a nonREM peak time value that is greater than 55% nonREM sleep per hour by the third hour after the compound is administered to a subject; a cumulative total increase in nonREM sleep of not less than 20 minutes for compound doses that produce maximum sleep consolidation; a longest sleep bout that is greater than 13 minutes in duration; net longest sleep bout post treatment is greater than or equal to 3 minutes when adjusted using a baseline value obtained at least 24 hours prior to administration of the compound to a subject; an average sleep bout that is greater than 5 minutes at absolute peak; administration of the compound to a subject does not produce appreciable amounts of rebound insomnia; administration of the compound to a subject does not appreciably inhibit REM sleep; and administration of the compound to a subject does not disproportionately inhibit locomotor activity relative to the normal effects of sleep.

In another embodiment, the compound of Formula I for use in the methods of the invention has one or more of the following characteristics: an inhibition constant ($K_i$) with regard to H1 receptor binding of less than 300 nM; a $K_t$ with regard to off target binding to an off target selected from M1, M2, M3, D1, D2, $\alpha 1$ and $\alpha 2$ that is greater than 1 µm; a nonREM peak time value that is greater than 55% nonREM sleep per hour by the third hour after the compound is administered to a subject; a cumulative total increase in nonREM sleep of not less than 20 minutes for compound doses that produce maximum sleep consolidation; a longest sleep bout that is greater than 13 minutes in duration; net longest sleep bout post treatment is greater than or equal to 3 minutes when adjusted using a baseline value obtained at least 24 hours prior to administration of the compound to a subject; an average sleep bout that is greater than 5 minutes at absolute peak; administration of the compound to a subject does not produce appreciable amounts of rebound insomnia; administration of the compound to a subject does not appreciably inhibit REM sleep; and administration of the compound to a subject does not disproportionately inhibit locomotor activity relative to the normal effects of sleep.

In another embodiment, the compound of Formula I for use in the methods of the invention has one or more of the following characteristics: an inhibition constant ($K_i$) with regard to H1 receptor binding of less than 150 nM; a $K_t$ with regard to off target binding to an off target selected from M1, M2, and M3, that is greater than 10 µM; a nonREM peak time value that is greater than 55% nonREM sleep per hour by the third hour after the compound is administered to a subject; a cumulative total increase in nonREM sleep not less than 20 minutes for compound doses that produce maximum sleep consolidation; a longest sleep bout that is greater than 17 minutes in duration; net longest sleep bout post treatment is greater than or equal to 5 minutes when adjusted using a baseline value obtained at least 24 hours prior to administration of the compound to a subject; an average sleep bout that is greater than 6 minutes at absolute peak; administration of the compound to a subject does not produce appreciable amounts of rebound insomnia; administration of the compound to a subject does not appreciably inhibit REM sleep; and administration of the compound to a subject does not disproportionately inhibit locomotor activity or motor tone relative to the normal effects of sleep.

As used herein, the "linker" is the chain of atoms connecting the piperazine nitrogen to the Z group.

The methods of the invention are used to treat a variety of subjects, including, for example, humans, companion animals, farm animals, laboratory animals and wild animals.

In one embodiment, the compound used in the method of modulating sleep is Compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, or 88.

In one embodiment, $R_9$ and $R_{10}$ and the carbon they are attached to are absent. In one embodiment, $R_9$ and $R_{10}$, together with the carbon to which they are attached, are connected to form a spiro ring of size 3 to 7. In one embodiment, $R_{11}$ and $R_{12}$, together with the carbon to which they are attached, are connected to form a spiro ring of size 3 to 7. For example, $R_9$ and $R_{10}$, together with the carbon to which they are attached, or $R_{11}$ and $R_{12}$, together with the carbon to which they are attached, are connected to form a spiro 3-membered cyclopropyl ring.

In one embodiment, Z is $CO_2H$, tetrazole, or sulfonamide. Examples of sulfonamides include acyl sulfonamides. For example, Z can have the formula

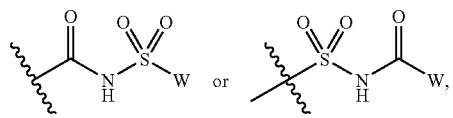

where W is a substituent chosen as needed to modulate the effects of the polar surface area of the Z moiety such that the desired level of oral absorption, CNS penetration, and rate of excretion into urine or bile is obtained. Examples of useful W substituents for this purpose include an alkyl group (optionally containing a double or triple bond or heteroatom substituted e.g., $CH_2OCH_3$ or $CH_2OCH_2CH_3$), a cycloalkyl group (optionally containing a double bond), a heterocyclyl group, an aryl group, or a heteroaryl group, optionally substituted, such as those shown below:

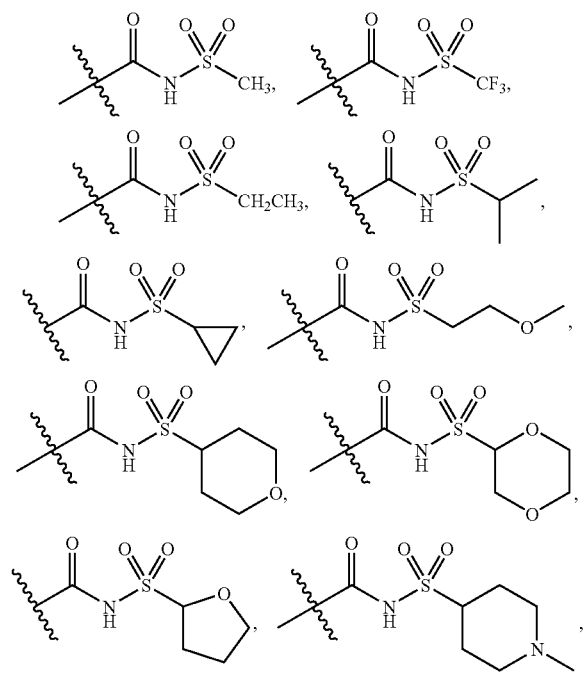

-continued

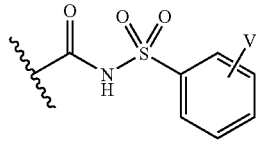

where V is one or more side chains selected to modulate the pKa of the acylsulfonamide moiety, or to affect the physical or metabolic properties of the compound. Examples of V side chains include halogens such as F, Cl, or Br; $C_1$-$C_6$ alkoxy groups such as $OCH_3$ or $OCH_2CH_3$; $C_1$-$C_6$ alkyl or $C_3$-$C_8$ cycloalkyl groups such as $CH_3$, $CF_3$, or cyclopropyl; heteroatom substituted $C_1$-$C_6$ alkyl or $C_3$-$C_8$ cycloalkyl, such as $CH_2OCH_3$, or $CH_2OCH_2CH_3$; electron withdrawing groups such as CN, a ketone, an amide, or a sulfone,

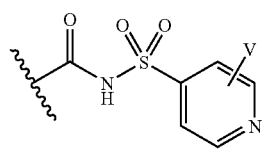

(and pyridyl isomers),

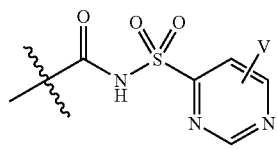

(and pyrimidine isomers), and

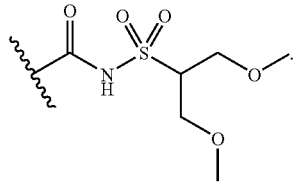

In another embodiment, Z is a sulfamide, for example, an acyl sulfamide. For example, Z can have the formula

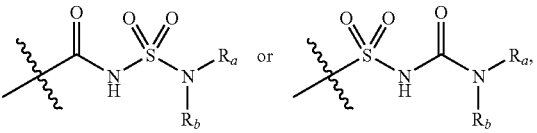

where $R_a$ and $R_b$ are, independently, for example an alkyl group, a cycloalkyl group, a heterocyclyl group, an aryl group, or a heteroaryl group, optionally substituted. Examples include the following:

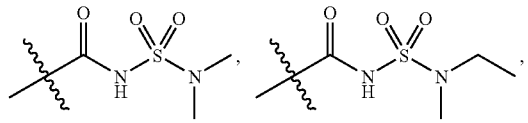

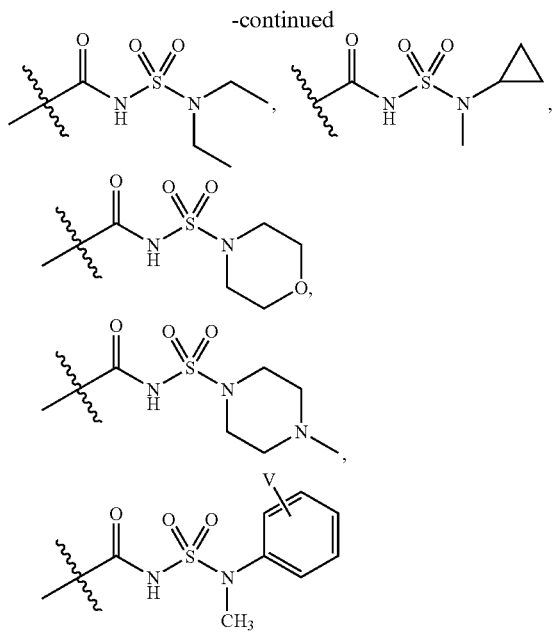

(where V is a halogen such as F, Cl, or Br; $C_1$-$C_6$ alkoxy such as $OCH_3$ or $OCH_2CH_3$; $C_1$-$C_6$ alkyl or $C_3$-$C_8$ cycloalkyl such as $CH_3$ or $CF_3$, cyclopropyl; heteroatom substituted $C_1$-$C_6$ alkyl or $C_3$-$C_8$ cycloalkyl, such as $CH_2OCH_3$, or $CH_2OCH_2CH_3$; an electron withdrawing group such as CN, a ketone, an amide, or a sulfone),

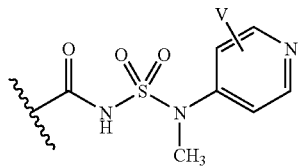

(and pyridyl isomers),

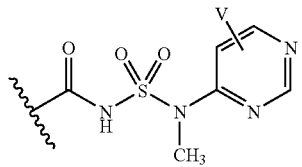

(and pyrimidine isomers).

In another embodiment, when Z is COOH, at least one of $R_1$-$R_8$ and at least one of $R_9$-$R_{12}$ are not hydrogen.

In one embodiment, $R_6$ is not H or halogen. In another embodiment, $R_1$-$R_5$ and $R_7$-$R_8$ are each hydrogen, and $R_6$ is not H or halogen.

In one embodiment, at least one of $R_1$-$R_8$ is not hydrogen, and the remaining $R_1$-$R_8$ are hydrogen. In another embodiment, at least two of $R_1$-$R_8$ are not hydrogen, and the remaining $R_1$-$R_8$ are hydrogen. In another embodiment, at least three of $R_1$-$R_8$ are not hydrogen and the remaining $R_1$-$R_8$ are hydrogen. In another embodiment, at least four of $R_1$-$R_8$ are not hydrogen and the remaining $R_1$-$R_8$ are hydrogen. In one embodiment, $R_2$ is not hydrogen. In one embodiment, $R_3$ is not hydrogen. In one embodiment, $R_6$ is not hydrogen. In one embodiment, $R_7$ is not hydrogen. In one embodiment, $R_3$ and $R_6$ are not hydrogen. In another embodiment, $R_2$ and $R_6$ are not hydrogen. In another embodiment, $R_3$ and $R_7$ are not hydrogen. In another embodiment, $R_2$ and $R_7$ are not hydrogen. In another embodiment, $R_2$ and $R_3$ are not hydrogen. In another embodiment, $R_6$ and $R_7$ are not hydrogen.

In one embodiment, at least one of $R_1$-$R_8$ is methyl, chloro, fluoro, bromo, hydroxy, methoxymethylene or methoxy. In another embodiment, $R_2$ is methyl, chloro, fluoro, bromo, hydroxy, methoxymethylene, or methoxy. In another embodiment, $R_3$ is methyl, chloro, fluoro, bromo, hydroxy, methoxymethylene, or methoxy. In another embodiment, $R_6$ is methyl, chloro, fluoro, bromo, hydroxy, methoxymethylene, or methoxy. In another embodiment, $R_7$ is methyl, chloro, fluoro, bromo, hydroxy, methoxymethylene, or methoxy.

In another embodiment, at least two of $R_1$-$R_8$ are methyl, chloro, fluoro, bromo, hydroxy, methoxymethylene, or methoxy. In another embodiment, at least two of $R_1$-$R_8$ are methyl, methoxymethylene, chloro, fluoro, bromo, hydroxy, or methoxy; and Z is COOH. In another embodiment, at least two of $R_1$-$R_8$ are methyl, methoxymethylene, chloro, fluoro, bromo, hydroxy, or methoxy; $R_9$ and $R_{10}$ are hydrogen; and Z is COOH.

In one embodiment, $R_3$ and $R_6$ are both methyl, methoxy, hydroxy, methoxymethylene, chloro, fluoro, or bromo, and the remaining $R_1$-$R_2$, $R_4$-$R_5$, and $R_7$-$R_8$ are hydrogen. In another embodiment, $R_2$ and $R_6$ are both methyl, methoxy, hydroxy, methoxymethylene, chloro, fluoro, or bromo, and the remaining $R_1$, $R_3$-$R_5$, and $R_7$-$R_8$ are hydrogen. In one embodiment, $R_3$ and $R_7$ are both methyl, methoxy, hydroxy, methoxymethylene, chloro, fluoro, or bromo, and the remaining $R_1$-$R_2$, $R_4$-$R_6$, and $R_8$ are hydrogen. In one embodiment, $R_2$ and $R_7$ are both methyl, methoxy, hydroxy, methoxymethylene, chloro, fluoro, or bromo, and the remaining $R_1$, $R_3$-$R_6$, and $R_8$ are hydrogen. In one embodiment, $R_2$ and $R_3$ are both methyl, methoxy, hydroxy, methoxymethylene, chloro, fluoro, or bromo, and the remaining $R_1$ and $R_4$-$R_8$ are hydrogen.

In one embodiment, $R_6$ is methyl. In one embodiment, $R_6$ is methyl and $R_2$ or $R_3$ is methyl, methoxy, methoxymethylene, chloro, fluoro, or bromo. In another embodiment, $R_6$ is fluoro, and $R_2$ or $R_3$ is methyl, methoxymethylene, or methoxy. In one embodiment, $R_6$ is methoxy. In one embodiment, $R_6$ is methoxy and $R_2$ or $R_3$ is methyl, methoxy, hydroxy, methoxymethylene, chloro, fluoro, or bromo. In another embodiment, $R_6$ is fluoro and $R_2$ or $R_3$ is methoxy.

In one embodiment, $R_9$ and $R_{10}$ are hydrogen.

In one embodiment, $R_9$ and $R_{10}$ are methyl. In another embodiment, $R_9$ and $R_{10}$ are methyl, $R_6$ is hydrogen or halogen, and $R_1$-$R_5$ and $R_7$-$R_8$ are hydrogen. In another embodiment, $R_9$ and $R_{10}$ are methyl, $R_6$ is hydrogen or halogen, $R_1$-$R_5$ and $R_7$-$R_8$ are hydrogen, and Z is COOH.

In one embodiment, $R_9$ and $R_{10}$ are ethyl. In another embodiment, $R_9$ and $R_{10}$ are ethyl, $R_6$ is hydrogen or halogen, and $R_1$-$R_5$ and $R_7$-$R_8$ are hydrogen. In another embodiment, $R_9$ and $R_{10}$ are ethyl, $R_6$ is hydrogen or halogen, $R_1$-$R_5$ and $R_7$-$R_8$ are hydrogen, and Z is COOH.

In one embodiment, $R_9$ and $R_{10}$ and the carbon to which they are attached are connected to form a three-membered spiro (cyclopropyl) ring. In another embodiment, $R_9$ and $R_{10}$ and the carbon to which they are attached are connected to form a three-membered spiro (cyclopropyl) ring, $R_6$ is hydrogen or halogen, and $R_1$-$R_5$, $R_7$-$R_8$ are hydrogen. In another embodiment, $R_9$ and $R_{10}$ and the carbon to which they are attached are connected to form a three-membered spiro (cyclopropyl) ring, $R_6$ is hydrogen or halogen, and $R_1$-$R_5$ and $R_7$-$R_8$ are hydrogen, and Z is COOH.

In another embodiment, $R_9$ and $R_{10}$ are methyl, $R_6$ is methoxy, and $R_1$-$R_5$ and $R_7$-$R_8$ are hydrogen. In another embodiment, $R_9$ and $R_{10}$ are methyl, $R_6$ is methoxy, $R_1$-$R_5$ and $R_7$-$R_8$ are hydrogen, and Z is COOH.

In another embodiment, $R_9$ and $R_{10}$ are ethyl, $R_6$ is methoxy, and $R_1$-$R_5$ and $R_7$-$R_8$ are hydrogen. In another embodiment, $R_9$ and $R_{10}$ are ethyl, $R_6$ is methoxy, $R_1$-$R_5$ and $R_7$-$R_8$ are hydrogen, and Z is COOH.

In another embodiment, $R_9$ and $R_{10}$ and the carbon to which they are attached are connected to form a three-membered spiro (cyclopropyl) ring, $R_6$ is methoxy, and $R_1$-$R_5$ and $R_7$-$R_8$ are hydrogen. In another embodiment, $R_9$ and $R_{10}$ and the carbon to which they are attached are connected to form a three-membered spiro (cyclopropyl) ring, $R_6$ is methoxy, and $R_1$-$R_5$ and $R_7$-$R_8$ are hydrogen and Z is COOH.

In one embodiment, $R_{11}$ and $R_{12}$ are methyl. In another embodiment, $R_{11}$ and $R_{12}$ are methyl, $R_6$ is hydrogen or halogen, and $R_1$-$R_5$ and $R_7$-$R_{10}$ are hydrogen. In another embodiment, $R_{11}$ and $R_{12}$ are methyl, $R_6$ is hydrogen or halogen, $R_1$-$R_5$ and $R_7$-$R_{10}$ are hydrogen, and Z is COOH.

In one embodiment, $R_{11}$ and $R_{12}$ are ethyl. In another embodiment, $R_{11}$ and $R_{12}$ are ethyl, $R_6$ is hydrogen or halogen, and $R_1$-$R_5$ and $R_7$-$R_{10}$ are hydrogen. In another embodiment, $R_{11}$ and $R_{12}$ are ethyl, $R_6$ is hydrogen or halogen, $R_1$-$R_5$ and $R_7$-$R_{10}$ are hydrogen, and Z is COOH.

In one embodiment, $R_{11}$ and $R_{12}$ and the carbon to which they are attached are connected to form a three-membered spiro (cyclopropyl) ring. In another embodiment, $R_{11}$ and $R_{12}$ and the carbon to which they are attached are connected to form a three-membered spiro (cyclopropyl) ring, $R_6$ is hydrogen or halogen, and $R_1$-$R_5$ and $R_7$-$R_{10}$ are hydrogen. In another embodiment, $R_{11}$ and $R_{12}$ and the carbon to which they are attached are connected to form a three-membered spiro (cyclopropyl) ring, $R_6$ is hydrogen or halogen, and $R_1$-$R_5$ and $R_7$-$R_{10}$ are hydrogen, and Z is COOH.

In one embodiment, $R_{11}$ and $R_{12}$ are methyl, and $R_6$ is methoxy. In another embodiment, $R_{11}$ and $R_{12}$ are methyl, $R_6$ is methoxy, and $R_1$-$R_5$ and $R_7$-$R_{10}$ are hydrogen. In another embodiment, $R_{11}$ and $R_{12}$ are methyl, $R_6$ is methoxy, $R_1$-$R_5$ and $R_7$-$R_{10}$ are hydrogen, and Z is COOH.

In one embodiment, $R_{11}$ and $R_{12}$ are ethyl and $R_6$ is methoxy. In another embodiment, $R_{11}$ and $R_{12}$ are ethyl, $R_6$ is methoxy, and $R_1$-$R_5$ and $R_7$-$R_{10}$ are hydrogen. In another embodiment, $R_{11}$ and $R_{12}$ are ethyl, $R_6$ is methoxy, $R_1$-$R_5$ and $R_7$-$R_{10}$ are hydrogen, and Z is COOH.

In one embodiment, $R_{11}$ and $R_{12}$ and the carbon to which they are attached are connected to form a three-membered spiro (cyclopropyl) ring, and $R_6$ is methoxy. In another embodiment, $R_{11}$ and $R_{12}$ and the carbon to which they are attached are connected to form a three-membered spiro (cyclopropyl) ring, $R_6$ is methoxy, and $R_1$-$R_5$ and $R_7$-$R_{10}$ are hydrogen. In another embodiment, $R_{11}$ and $R_{12}$ and the carbon to which they are attached are connected to form a three-membered spiro (cyclopropyl) ring, $R_6$ is methoxy, and $R_1$-$R_5$ and $R_7$-$R_{10}$ are hydrogen, and Z is COOH.

In one embodiment, in the compound of Formula I used in the method of the invention, q is zero. In another embodiment, q is zero, and $R_9$ and $R_{10}$ together with the carbon to which they are attached are absent. In another embodiment, q is zero, $R_9$ and $R_{10}$ together with the carbon to which they are attached are absent, and X and Y are absent. In another embodiment, q is zero, $R_9$ and $R_{10}$ together with the carbon to which they are attached are absent, X and Y are absent, and the sum of m, n, o, and p is 1 or 2.

In one aspect, the compounds of the invention are used to modulate sleep, e.g., by decreasing the time to sleep onset, increasing the average sleep bout length, and/or increasing the maximum sleep bout length. In another aspect, the loxapine analogs of the invention are used to treat a sleep disorder. For example, the loxapine analogs of the invention are used to treat circadian rhythm abnormality, insomnia, parasomnia, sleep apnea syndrome, narcolepsy and/or hypersomnia.

In one embodiment, the loxapine analogs of the invention are used in the treatment of a circadian rhythm abnormality, such as, for example, jet lag, shift-work disorders, delayed sleep phase syndrome, advanced sleep phase syndrome, and non-24 hour sleep-wake disorder.

In another embodiment, the loxapine analogs are used in the treatment of insomnia, including, for example, extrinsic insomnia, psychophysiologic insomnia, altitude insomnia, restless leg syndrome, periodic limb movement disorder, medication-dependent insomnia, drug-dependent insomnia, alcohol-dependent insomnia and insomnia associated with mental disorders.

In one embodiment, the loxapine analogs of the invention are used to treat a parasomnia disorder, such as, e.g., somnambulism, pavor nocturnus, REM sleep behavior disorder, sleep bruxism and sleep enuresis.

In another embodiment, the loxapine analogs are used to treat a sleep apnea disorder, such as, for example, central sleep apnea, obstructive sleep apnea and mixed sleep apnea.

Pharmaceutical compositions that include a compound of Formula I or a pharmaceutically acceptable salt thereof are used in the methods of modulating sleep. In one embodiment, the compound of Formula I or a pharmaceutically acceptable salt thereof is co-administered with one or more additional therapies.

In another aspect, the present invention provides a method of modulating sleep in a subject by administering a therapeutically effective amount of a compound having the formula of Formula II:

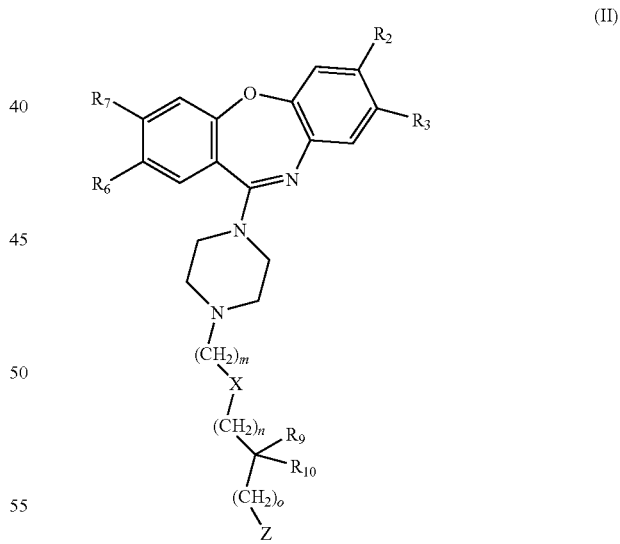

(II)

or a pharmaceutically effective salt thereof, wherein m, n, and o are, independently, 0, 1, 2, 3, 4, 5, or 6; X is absent, O, S, C(O), SO, or $SO_2$; $R_2$, $R_3$, $R_6$, and $R_7$ are, independently, selected from H, F, Cl, Br, $CF_3$, $CH_3$, $CH_2CH_3$, $CH(CH_3)_2$, cyclopropyl, OH, $OCH_3$, $OCF_3$, $CH_2OCH_3$, and $CH_2OCH_2CH_3$; $R_9$, and $R_{10}$, are, independently, H, $C_1$-$C_6$ straight chain alkyl; $C_2$-$C_6$ branched alkyl, or $R_9$ and $R_{10}$ together with the carbon to which they are attached, are connected to form a spiro ring of size 3, 4, 5, 6, or 7 atoms; and Z is COOH, $COOR_{13}$ (where $R_{13}$ is $C_1$-$C_6$ alkyl) $CONHS(O)_2$-alkyl, $CONHS(O)_2$-heteroalkyl, $CONHS(O)_2$-aryl, $CONHS(O)_2$-heteroaryl, $S(O)_2NHCO$-alkyl, $S(O)_2NHCO$-heteroalkyl, $S(O)_2NHCO$-aryl, $S(O)_2NHCO$-heteroaryl, $CONHS(O)_2NH$-alkyl; $CONHS(O)_2NH$-heteroalkyl; $CONHS(O)_2NH$-aryl; $CONHS(O)_2NH$-heteroaryl; or tetrazole, provided that when Z is COOH or $COOR_{13}$, and $R_6$ is H or halogen, then $R_1$-$R_5$ and $R_7$-$R_{12}$ are not each hydrogen, further provided that when m is zero, X is absent.

In one embodiment, the compounds of Formula II for use in the methods of the invention have one or more of the following characteristics: an inhibition constant ($K_i$) with regard to H1 receptor binding of less than 500 nM; a $K_i$ with regard to off target binding to an off target selected from M1, M2, M3, D1, D2, α1 and α2 that is greater than 500 nM and/or more than 5 times greater than the $K_i$ with regard to the H1 receptor; a nonREM peak time value that is greater than 55% nonREM sleep per hour by the third hour after the compound is administered to a subject; a cumulative total increase in nonREM sleep of not less than 20 minutes for compound doses that produce maximum sleep consolidation; a longest sleep bout that is greater than 13 minutes in duration; net longest sleep bout post treatment is greater than or equal to 3 minutes when adjusted using a baseline value obtained at least 24 hours prior to administration of the compound to a subject; an average sleep bout that is greater than 5 minutes at absolute peak; administration of the compound to a subject does not produce appreciable amounts of rebound insomnia; administration of the compound to a subject does not appreciably inhibit REM sleep; and administration of the compound to a subject does not disproportionately inhibit locomotor activity relative to the normal effects of sleep.

In another embodiment, the compound of Formula II for use in the methods of the invention has one or more of the following characteristics: an inhibition constant ($K_i$) with regard to H1 receptor binding of less than 300 nM; a $K_i$ with regard to off target binding to an off target selected from M1, M2, M3, D1, D2, α1 and α2 that is greater than 1 μm; a nonREM peak time value that is greater than 55% nonREM sleep per hour by the third hour after the compound is administered to a subject; a cumulative total increase in nonREM sleep of not less than 20 minutes for compound doses that produce maximum sleep consolidation; a longest sleep bout that is greater than 13 minutes in duration; net longest sleep bout post treatment is greater than or equal to 3 minutes when adjusted using a baseline value obtained at least 24 hours prior to administration of the compound to a subject; an average sleep bout that is greater than 5 minutes at absolute peak; administration of the compound to a subject does not produce appreciable amounts of rebound insomnia; administration of the compound to a subject does not appreciably inhibit REM sleep; and administration of the compound to a subject does not disproportionately inhibit locomotor activity relative to the normal effects of sleep.

In another embodiment, the compound of Formula II for use in the methods of the invention has one or more of the following characteristics: an inhibition constant ($K_i$) with regard to H1 receptor binding of less than 150 nM; a $K_i$ with regard to off target binding to an off target selected from M1, M2, and M3, that is greater than 10 μM; a nonREM peak time value that is greater than 55% nonREM sleep per hour by the third hour after the compound is administered to a subject; a cumulative total increase in nonREM sleep not less than 20 minutes for compound doses that produce maximum sleep consolidation; a longest sleep bout that is greater than 17 minutes in duration; net longest sleep bout post treatment is greater than or equal to 5 minutes when adjusted using a baseline value obtained at least 24 hours prior to administration of the compound to a subject; an average sleep bout that is greater than 6 minutes at absolute peak; administration of the compound to a subject does not produce appreciable amounts of rebound insomnia; administration of the compound to a subject does not appreciably inhibit REM sleep; and administration of the compound to a subject does not disproportionately inhibit locomotor activity or motor tone relative to the normal effects of sleep.

In one embodiment, Z is $CO_2H$ or tetrazole. In another embodiment, when Z is COOH, at least one of $R_2$, $R_3$, $R_6$, and $R_7$, and at least one of $R_9$-$R_{10}$ are not hydrogen. In one embodiment, o is zero.

In one embodiment, at least one of $R_2$, $R_3$, $R_6$, $R_7$, and at least one of $R_9$-$R_{10}$ are not hydrogen when Z is COOH. In one embodiment, $R_2$, $R_3$, and $R_7$ are each hydrogen and $R_6$ is not hydrogen or halogen. In one embodiment, $R_2$, $R_3$, and $R_7$, are each hydrogen, and $R_6$ is methyl, methoxy, methoxymethylene, or hydroxy.

In one embodiment, at least two of $R_2$, $R_3$, $R_6$, and $R_7$ are not hydrogen, and the remaining $R_2$, $R_3$, $R_6$, and $R_7$ are hydrogen. In another embodiment, at least three of $R_2$, $R_3$, $R_6$ and $R_7$ are not hydrogen and the remaining $R_2$, $R_3$, $R_6$, and $R_7$ are hydrogen. In one embodiment, $R_2$ is not hydrogen. In one embodiment, $R_3$ is not hydrogen. In one embodiment, $R_6$ is not hydrogen. In one embodiment, $R_7$ is not hydrogen. In one embodiment, $R_3$ and $R_6$ are not hydrogen. In another embodiment, $R_2$ and $R_6$ are not hydrogen. In another embodiment, $R_3$ and $R_7$ are not hydrogen.

In one embodiment, $R_9$ and $R_{10}$ are each methyl. In another embodiment, $R_9$ and $R_{10}$ are each ethyl. In another embodiment, $R_9$ and $R_{10}$ are each hydrogen.

In one embodiment, $R_9$ and $R_{10}$ and the carbon to which they are attached are connected to form a spiro ring of size from three to seven. For example, in one embodiment, $R_9$ and $R_{10}$ and the carbon to which they are attached are connected to form a three-membered spiro (cyclopropyl) ring.

In one embodiment, $R_9$ and $R_{10}$ are methyl, $R_6$ is hydrogen or halogen, and the remaining $R_2$, $R_3$, and $R_7$ are hydrogen. $R_9$ and $R_{10}$ are methyl, $R_6$ is hydrogen or halogen, and the remaining $R_2$, $R_3$, and $R_7$ are hydrogen, and Z is COOH.

In one embodiment, $R_9$ and $R_{10}$ are ethyl, $R_6$ is hydrogen or halogen, and the remaining $R_2$, $R_3$, and $R_7$ are hydrogen. In another embodiment, $R_9$ and $R_{10}$ are ethyl, $R_6$ is hydrogen or halogen, and the remaining $R_2$, $R_3$, and $R_7$ are hydrogen, and Z is COOH.

In one embodiment, $R_9$ and $R_{10}$ and the carbon to which they are attached are connected to form a three-membered spiro (cyclopropyl) ring. In another embodiment, $R_9$ and $R_{10}$ and the carbon to which they are attached are connected to form a three-membered spiro (cyclopropyl) ring, $R_6$ is hydrogen or halogen, and the remaining $R_2$, $R_3$, and $R_7$ are hydrogen. In another embodiment, $R_9$ and $R_{10}$ and the carbon to which they are attached are connected to form a three-membered spiro (cyclopropyl) ring, $R_6$ is hydrogen or halogen, and the remaining $R_2$, $R_3$, and $R_7$ are hydrogen, and Z is COOH.

In one embodiment, in the compound of Formula II used in the method of the invention, o is zero. In another embodiment, o is zero, and X is absent. In another embodiment, o is zero, X is absent, and the sum of m and n is 1 or 2.

In one embodiment, the sleep modulation is, e.g., decreasing the time to sleep onset, increasing the average sleep bout length, and/or increasing the maximum sleep bout length. In one embodiment, the sleep modulation treats a sleep disorder.

Pharmaceutical compositions that include a compound of Formula II or a pharmaceutically acceptable salt thereof are also used in the compounds of modulating sleep in a subject.

In one embodiment, the compound of Formula II or a pharmaceutically acceptable salt thereof is co-administered with one or more additional therapies.

In another aspect, the invention provides a compound of modulating sleep in a subject by administering a therapeutically effective amount of a compound having the formula of Formula III:

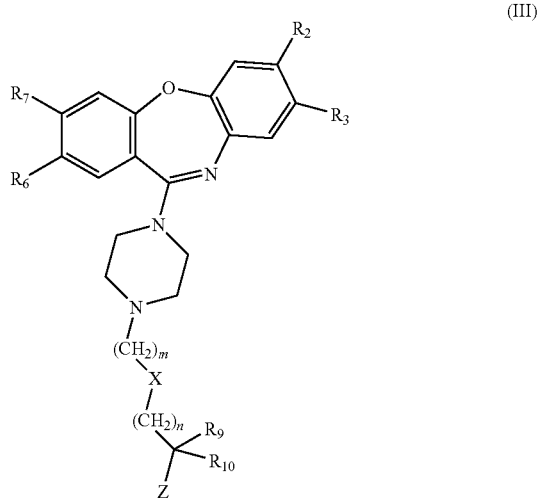

(III)

or a pharmaceutically effective salt thereof, wherein m and n are, independently, 0, 1, 2, 3, or 4, X is absent, O or S; $R_2$, $R_3$, $R_6$, and $R_7$ are, independently, selected from H, F, Cl, Br, $CF_3$, $CH_3$, OH, $CH_2CH_3$, $CH(CH_3)_2$, $OCH_3$, $CH_2OCH_3$, and $CH_2OCH_2CH_3$; $R_9$, and $R_{10}$, are, independently H, $C_1$-$C_6$ straight chain alkyl; $C_2$-$C_6$ branched alkyl, or $R_9$, and $R_{10}$, together with the carbon to which they are attached, are connected to form a spiro ring of size 3, 4, 5, 6, or 7 atoms; and Z is selected from $CO_2H$, $CONHS(O)_2$-alkyl, $CONHS(O)_2$-cycloalkyl, $CONHS(O)_2$-heteroalkyl, $CONHS(O)_2$-aryl, $CONHS(O)_2$-heteroaryl, and tetrazole; provided that when Z is COOH and $R_6$ is H, F, Cl, or Br, then $R_2$, $R_3$, $R_7$, and $R_9$-$R_{10}$ are not each hydrogen, further provided that when m is zero, X is absent.

In one embodiment, the compounds of Formula III for use in the methods of the invention have one or more of the following characteristics: an inhibition constant ($K_i$) with regard to H1 receptor binding of less than 500 nM; a $K_i$ with regard to off target binding to an off target selected from M1, M2, M3, D1, D2, α1 and α2 that is greater than 500 nM and/or more than 5 times greater than the $K_i$ with regard to the H1 receptor; a nonREM peak time value that is greater than 55% nonREM sleep per hour by the third hour after the compound is administered to a subject; a cumulative total increase in nonREM sleep of not less than 20 minutes for compound doses that produce maximum sleep consolidation; a longest sleep bout that is greater than 13 minutes in duration; net longest sleep bout post treatment is greater than or equal to 3 minutes when adjusted using a baseline value obtained at least 24 hours prior to administration of the compound to a subject; an average sleep bout that is greater than 5 minutes at absolute peak; administration of the compound to a subject does not produce appreciable amounts of rebound insomnia; administration of the compound to a subject does not appreciably inhibit REM sleep; and administration of the compound to a subject does not disproportionately inhibit locomotor activity relative to the normal effects of sleep.

In another embodiment, the compound of Formula III for use in the methods of the invention has one or more of the following characteristics: an inhibition constant ($K_i$) with regard to H1 receptor binding of less than 300 nM; a $K_i$ with regard to off target binding to an off target selected from M1, M2, M3, D1, D2, α1 and α2 that is greater than 1 μm; a nonREM peak time value that is greater than 55% nonREM sleep per hour by the third hour after the compound is administered to a subject; a cumulative total increase in nonREM sleep of not less than 20 minutes for compound doses that produce maximum sleep consolidation; a longest sleep bout that is greater than 13 minutes in duration; net longest sleep bout post treatment is greater than or equal to 3 minutes when adjusted using a baseline value obtained at least 24 hours prior to administration of the compound to a subject; an average sleep bout that is greater than 5 minutes at absolute peak; administration of the compound to a subject does not produce appreciable amounts of rebound insomnia; administration of the compound to a subject does not appreciably inhibit REM sleep; and administration of the compound to a subject does not disproportionately inhibit locomotor activity relative to the normal effects of sleep.

In another embodiment, the compound of Formula III for use in the methods of the invention has one or more of the following characteristics: an inhibition constant ($K_i$) with regard to H1 receptor binding of less than 150 nM; a $K_i$ with regard to off target binding to an off target selected from M1, M2, and M3, that is greater than 10 μM; a nonREM peak time value that is greater than 55% nonREM sleep per hour by the third hour after the compound is administered to a subject; a cumulative total increase in nonREM sleep not less than 20 minutes for compound doses that produce maximum sleep consolidation; a longest sleep bout that is greater than 17 minutes in duration; net longest sleep bout post treatment is greater than or equal to 5 minutes when adjusted using a baseline value obtained at least 24 hours prior to administration of the compound to a subject; an average sleep bout that is greater than 6 minutes at absolute peak; administration of the compound to a subject does not produce appreciable amounts of rebound insomnia; administration of the compound to a subject does not appreciably inhibit REM sleep; and administration of the compound to a subject does not disproportionately inhibit locomotor activity or motor tone relative to the normal effects of sleep.

In one embodiment, Z is $CO_2H$ or tetrazole. In one embodiment, m is zero. In one embodiment, at least one of $R_2$, $R_3$, $R_6$, and $R_7$, and at least one of $R_9$-$R_{10}$, are not hydrogen when Z is COOH. In one embodiment, $R_2$, $R_3$, and $R_7$ are each hydrogen and $R_6$ is not hydrogen or halogen. In one embodiment, $R_2$, $R_3$, and $R_7$, are each hydrogen, and $R_6$ is methyl, methoxymethylene, methoxy, or hydroxy.

In one embodiment, $R_2$, $R_3$, and $R_7$ are each hydrogen, and $R_6$ is not hydrogen or halogen. In one embodiment, $R_2$, $R_3$, and $R_7$, are each hydrogen, and $R_6$ is methyl, methoxymethylene, methoxy, or hydroxy.

In one embodiment, at least two of $R_2$, $R_3$, $R_6$, and $R_7$ are not hydrogen, and the remaining $R_2$, $R_3$, $R_6$, and $R_7$ are hydrogen. In another embodiment, at least three of $R_2$, $R_3$, $R_6$, and $R_7$ are not hydrogen and the remaining $R_2$, $R_3$, $R_6$, and $R_7$ are hydrogen. In one embodiment, $R_2$ is not hydrogen. In one embodiment, $R_3$ is not hydrogen. In one embodiment, $R_6$ is not hydrogen. In one embodiment, $R_7$ is not hydrogen. In one embodiment, $R_3$ and $R_6$ are not hydrogen. In another embodiment, $R_2$ and $R_6$ are not hydrogen. In another embodiment, $R_3$ and $R_7$ are not hydrogen.

In one embodiment, $R_9$ and $R_{10}$ are each methyl. In another embodiment, $R_9$ and $R_{10}$ are each ethyl. In another embodiment, $R_9$ and $R_{10}$ are each hydrogen.

In one embodiment, $R_9$ and $R_{10}$ and the carbon to which they are attached are connected to form a spiro ring of size from three to seven. For example, in one embodiment, $R_9$ and $R_{10}$ and the carbon to which they are attached are connected to form a three-membered spiro (cyclopropyl) ring.

In one embodiment, $R_9$ and $R_{10}$ are methyl, $R_6$ is hydrogen or halogen, and the remaining $R_2$, $R_3$, and $R_7$ are hydrogen. In another embodiment, $R_9$ and $R_{10}$ are methyl, $R_6$ is hydrogen or halogen, and the remaining $R_2$, $R_3$, and $R_7$ are hydrogen, and Z is COOH.

In one embodiment, $R_9$ and $R_{10}$ are ethyl, $R_6$ is hydrogen or halogen, and the remaining $R_2$, $R_3$, and $R_7$ are hydrogen. In another embodiment, $R_9$ and $R_{10}$ are ethyl, $R_6$ is hydrogen or halogen, and the remaining $R_2$, $R_3$, and $R_7$ are hydrogen, and Z is COOH.

In one embodiment, $R_9$ and $R_{10}$ and the carbon to which they are attached are connected to form a three-membered spiro (cyclopropyl) ring. In another embodiment, $R_9$ and $R_{10}$ and the carbon to which they are attached are connected to form a three-membered spiro (cyclopropyl) ring, $R_6$ is hydrogen or halogen, and the remaining $R_2$, $R_3$, and $R_7$ are hydrogen. In another embodiment, $R_9$ and $R_{10}$ and the carbon to which they are attached are connected to form a three-membered spiro (cyclopropyl) ring, $R_6$ is hydrogen or halogen, and the remaining $R_2$, $R_3$, and $R_7$ are hydrogen, and Z is COOH.

In one embodiment, in the compound of Formula III used in the method of the invention, X is absent. In another embodiment, X is absent, and the sum of m and n is 1 or 2.

In one embodiment, the sleep modulation is, e.g., decreasing the time to sleep onset, increasing the average sleep bout length, and/or increasing the maximum sleep bout length. In one embodiment, the sleep modulation treats a sleep disorder.

Pharmaceutical compositions that include a compound of Formula III or a pharmaceutically acceptable salt thereof are also used in the compounds of modulating sleep according to the invention.

In another aspect, the invention provides a compound of modulating sleep in a subject by administering a therapeutically effective amount of a compound having the formula of Formula IV:

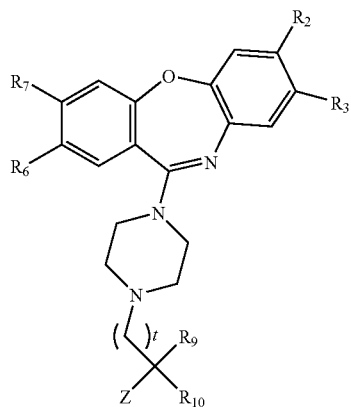

(IV)

or a pharmaceutically effective salt thereof wherein t is 1, 2, 3, or 4; $R_2$, $R_3$ $R_6$ and $R_7$ are, independently, H, F, Cl, Br, $CF_3$, $CH_3$, OH, $OCH_3$, $CH_2OCH_3$, or $CH_2OCH_2CH_3$; $R_9$-$R_{10}$ are H, $CH_3$, $CH_2CH_3$, or $R_9$ and $R_{10}$, together with the carbon to which they are attached, are connected to form a spiro ring of size 3, 4, 5, 6, or 7 atoms; and Z is selected from $CO_2H$, $CONHS(O)_2$-alkyl, $CONHS(O)_2$-cycloalkyl, $CONHS(O)_2$-heteroalkyl, $CONHS(O)_2$-aryl, $CONHS(O)_2$-heteroaryl, or tetrazole; provided that when Z is COOH and $R_6$ is H, F, Cl, or Br, then $R_2$, $R_3$, $R_7$, and $R_9$-$R_{10}$ are not each hydrogen.

In one embodiment, t=1 or 2.

In one embodiment, the compounds of Formula IV for use in the methods of the invention have one or more of the following characteristics: an inhibition constant ($K_i$) with regard to H1 receptor binding of less than 500 nM; a $K_i$ with regard to off target binding to an off target selected from M1, M2, M3, D1, D2, α1 and α2 that is greater than 500 nM and/or more than 5 times greater than the $K_i$ with regard to the H1 receptor; a nonREM peak time value that is greater than 55% nonREM sleep per hour by the third hour after the compound is administered to a subject; a cumulative total increase in nonREM sleep of not less than 20 minutes for compound doses that produce maximum sleep consolidation; a longest sleep bout that is greater than 13 minutes in duration; net longest sleep bout post treatment is greater than or equal to 3 minutes when adjusted using a baseline value obtained at least 24 hours prior to administration of the compound to a subject; an average sleep bout that is greater than 5 minutes at absolute peak; administration of the compound to a subject does not produce appreciable amounts of rebound insomnia; administration of the compound to a subject does not appreciably inhibit REM sleep; and administration of the compound to a subject does not disproportionately inhibit locomotor activity relative to the normal effects of sleep.

In another embodiment, the compound of Formula IV for use in the methods of the invention has one or more of the following characteristics: an inhibition constant ($K_i$) with regard to H1 receptor binding of less than 300 nM; a $K_i$ with regard to off target binding to an off target selected from M1, M2, M3, D1, D2, α1 and α2 that is greater than 1 μm; a nonREM peak time value that is greater than 55% nonREM sleep per hour by the third hour after the compound is administered to a subject; a cumulative total increase in nonREM sleep of not less than 20 minutes for compound doses that produce maximum sleep consolidation; a longest sleep bout that is greater than 13 minutes in duration; net longest sleep bout post treatment is greater than or equal to 3 minutes when adjusted using a baseline value obtained at least 24 hours prior to administration of the compound to a subject; an average sleep bout that is greater than 5 minutes at absolute peak; administration of the compound to a subject does not produce appreciable amounts of rebound insomnia; administration of the compound to a subject does not appreciably inhibit REM sleep; and administration of the compound to a subject does not disproportionately inhibit locomotor activity relative to the normal effects of sleep.

In another embodiment, the compound of Formula IV for use in the methods of the invention has one or more of the following characteristics: an inhibition constant ($K_i$) with regard to H1 receptor binding of less than 150 nM; a $K_i$ with regard to off target binding to an off target selected from M1, M2, and M3, that is greater than 10 μM; a nonREM peak time value that is greater than 55% nonREM sleep per hour by the third hour after the compound is administered to a subject; a cumulative total increase in nonREM sleep not less than 20 minutes for compound doses that produce maximum sleep consolidation; a longest sleep bout that is greater than 17 minutes in duration; net longest sleep bout post treatment is greater than or equal to 5 minutes when adjusted using a baseline value obtained at least 24 hours prior to administration of the compound to a subject; an average sleep bout that is greater than 6 minutes at absolute peak; administration of the compound to a subject does not produce appreciable amounts of rebound insomnia; administration of the compound to a subject does not appreciably inhibit REM sleep;

and administration of the compound to a subject does not disproportionately inhibit locomotor activity or motor tone relative to the normal effects of sleep.

In one embodiment, Z is $CO_2H$ or tetrazole. In another embodiment, when Z is COOH, at least one of $R_2$, $R_3$, and $R_7$, and at least one of $R_9$-$R_{10}$, are not hydrogen.

In one embodiment, $R_9$ and $R_{10}$ are each methyl. In another embodiment, $R_9$ and $R_{10}$ are each ethyl. In one embodiment, $R_9$ and $R_{10}$ and the carbon to which they are attached are connected to form a spiro ring of size from three to seven. For example, in one embodiment, $R_9$ and $R_{10}$ and the carbon to which they are attached are connected to form a three-membered spiro (cyclopropyl) ring.

In one embodiment, $R_9$ and $R_{10}$ are methyl; $R_6$ is hydrogen or halogen; and $R_2$ $R_3$ and $R_7$ are hydrogen. In another embodiment, $R_9$ and $R_{10}$ are methyl; $R_6$ is hydrogen or halogen; and $R_2$ $R_3$ and $R_7$ are hydrogen; and Z is COOH.

In one embodiment, $R_9$ and $R_{10}$ are ethyl; $R_6$ is hydrogen or halogen; and $R_2$ $R_3$ and $R_7$ are hydrogen. In another embodiment, $R_9$ and $R_{10}$ are methyl; $R_6$ is hydrogen or halogen; and $R_2$ $R_3$ and $R_7$ are hydrogen; and Z is COOH.

In one embodiment, $R_9$ and $R_{10}$ and the carbon to which they are attached are connected to form a three-membered spiro (cyclopropyl) ring. In another embodiment, $R_9$ and $R_{10}$ and the carbon to which they are attached are connected to form a three-membered spiro (cyclopropyl) ring, $R_6$ is hydrogen or halogen; and $R_2$ $R_3$ and $R_7$ are hydrogen. In another embodiment, $R_9$ and $R_{10}$ and the carbon to which they are attached are connected to form a three-membered spiro (cyclopropyl) ring, $R_6$ is hydrogen or halogen; and $R_2$ $R_3$ and $R_7$ are hydrogen; and Z is COOH.

In one embodiment, the sleep modulation is selected from decreasing the time to sleep onset, increasing the average sleep bout length, and increasing the maximum sleep bout length. In one embodiment, the sleep modulation treats a sleep disorder.

Pharmaceutical compositions that include a compound of Formula IV or a pharmaceutically acceptable salt thereof are also used in the compounds of modulating sleep according to the invention.

In one embodiment, the compound of Formula IV used in the methods of the invention is IVa, IVb, IVc, IVd, or IVe.

For example, when $R_9$ and $R_{10}$ are methyl, compounds have the general formula IVa:

(IVa)

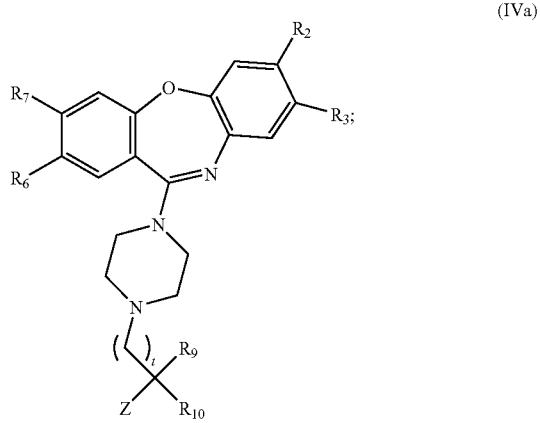

when $R_9$ and $R_{10}$ are connected to form a 3 membered spiro ring (cyclopropyl), compounds have the general formula IVb:

(IVb)

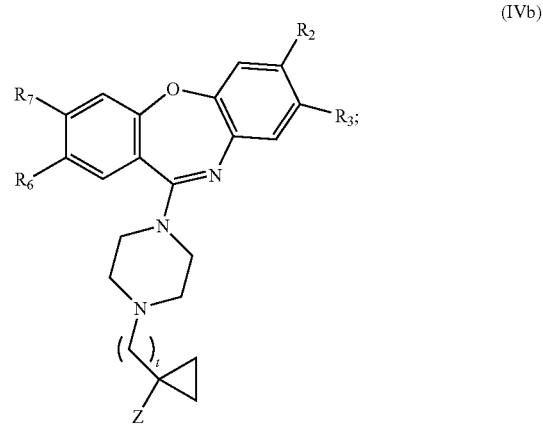

when $R_9$ and $R_{10}$ are ethyl, compounds have the general formula IVc:

(IVc)

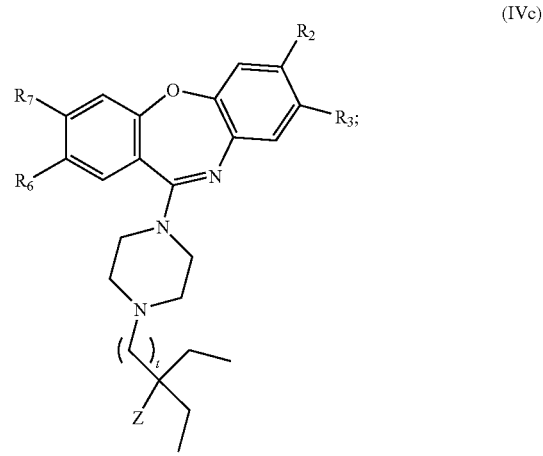

when $R_9$ and $R_{10}$ are ethyl, and the C-1 carbons are connected to form a 3 membered spiro ring (cyclopropyl), compounds have the general formula IVd:

(IVd)

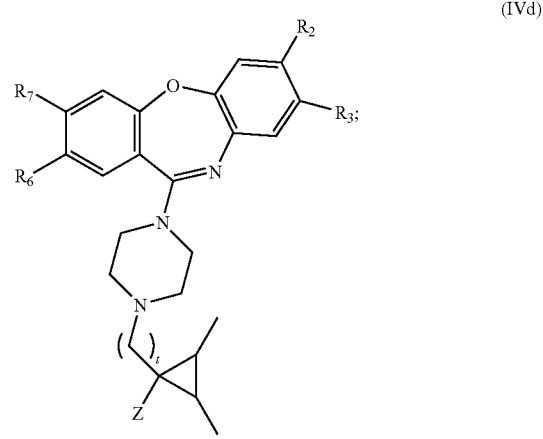

and when and $R_9$ and $R_{10}$ are hydrogen, compounds have the general formula IVe:

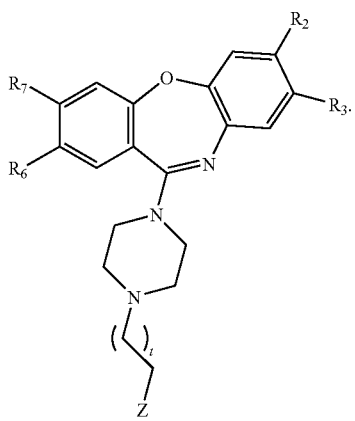

(IVe)

In another aspect, the invention provides a compound according to Formula I:

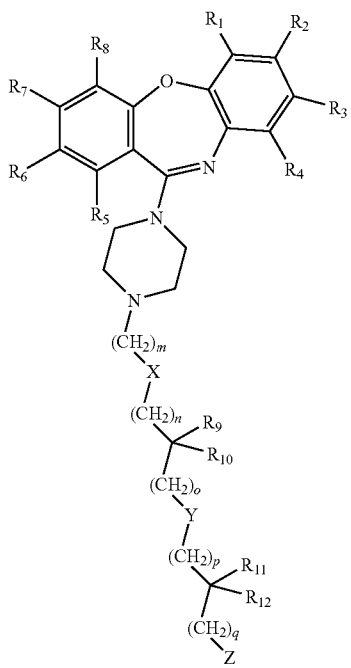

(I)

or a pharmaceutically effective salt thereof, wherein m, n, o, p, q are, independently, 0, 1, 2, 3, 4, 5, or 6; X and Y are, independently, absent, O, S, C(O), SO, or $SO_2$; $R_1$, $R_2$, $R_3$, $R_4$, $R_5$, $R_6$, $R_7$, and $R_8$ are, independently selected from H, F, Cl, Br, $CF_3$, $CH_3$, $C_2$-$C_6$ straight chain alkyl, $C_3$-$C_6$ branched alkyl, $C_3$-$C_7$ cycloalkyl, $C_3$-$C_7$ heterocyclyl, OH, $OCH_3$, $OCF_3$, $CH_2OCH_3$, $CH_2CH_2OCH_3$, $CH_2OCH_2CH_3$, and $C_1$-$C_6$ hydroxyalkyl; any hydrogen in the $CH_2$ groups in the linker is optionally substituted with H, F, Cl, Br, $CF_3$, $CH_3$, $C_2$-$C_6$ straight chain alkyl, $C_3$-$C_6$ branched alkyl, $C_3$-$C_7$ cycloalkyl, $C_3$-$C_7$ heterocyclyl, $OCH_3$, $OCF_3$, $CH_2OCH_3$, $CH_2CH_2OCH_3$, $CH_2OCH_2CH_3$, or $C_1$-$C_6$ hydroxyalkyl; $R_9$, $R_{10}$, $R_{11}$, and $R_{12}$ are, independently, H, $C_1$-$C_6$ straight chain alkyl, $C_2$-$C_6$ branched alkyl, or $R_9$ and $R_{10}$ together with the carbon to which they are attached are connected to form a spiro ring of size 3, 4, 5, 6, or 7 atoms, or $R_{11}$ and $R_{12}$ together with the carbon to which they are attached, are connected to form a spiro ring of size 3, 4, 5, 6, or 7 atoms; or substituents on two different atoms are connected to form a ring of size 3, 4, 5, 6, or 7 atoms; and Z is selected from $CO_2H$, $CO_2R_{13}$, where $R_{13}$ is $C_1$-$C_6$ alkyl, $CONR_{14}R_{15}$, where $R_{14}$ and $R_{15}$ are, independently, hydrogen or lower alkyl, $CONHS(O)_2$-alkyl, $CONHS(O)_2$-cycloalkyl, $CONHS(O)_2$-heteroalkyl, $CONHS(O)_2$-aryl, $CONHS(O)_2$-heteroaryl, $S(O)_2NHCO$-alkyl, $S(O)_2NHCO$-cycloalkyl, $S(O)_2NHCO$-heteroalkyl, $S(O)_2NHCO$-aryl, $S(O)_2NHCO$-heteroaryl, $CONHS(O)_2NH$-alkyl, $CONHS(O)_2NH$-cycloalkyl, $CONHS(O)_2NH$-heteroalkyl, $CONHS(O)_2N$-aryl, $CONHS(O)_2N$-heteroaryl, $SO_3H$, $SO_2H$, $S(O)NHCO$-alkyl, $S(O)NHCO$-aryl, $S(O)NHCO$-heteroaryl, $P(O)(OH)_2$, $P(O)OH$,

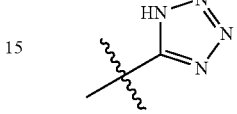

(tetrazole), or

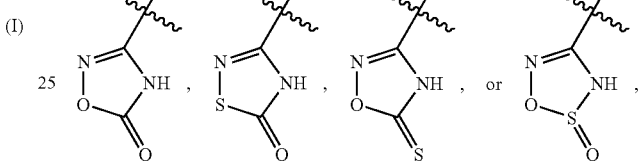

provided that when Z is COOH or $COOR_{13}$, and $R_6$ is H or halogen, then $R_1$-$R_5$ and $R_7$-$R_{12}$ are not each hydrogen, further provided that when m is zero, X is absent.

In one embodiment, the compound is Compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, or 88.

In one embodiment, Z is $CO_2H$, tetrazole, a sulfonamide, or a sulfamide. In another embodiment, when Z is COOH, at least one of $R_1$-$R_8$ and at least one of $R_9$-$R_{12}$ are not hydrogen.

In one embodiment, $R_6$ is not H or halogen. In another embodiment, $R_1$-$R_5$ and $R_7$-$R_8$ are each hydrogen and $R_6$ is not H or halogen.

In one embodiment, at least one of $R_1$-$R_8$ is not hydrogen, and the remaining $R_1$-$R_8$ are hydrogen. In another embodiment, at least two of $R_1$-$R_8$ are not hydrogen, and the remaining $R_1$-$R_8$ are hydrogen. In another embodiment, at least three of $R_1$-$R_8$ are not hydrogen and the remaining $R_1$-$R_8$ are hydrogen. In another embodiment, at least four of $R_1$-$R_8$ are not hydrogen and the remaining $R_1$-$R_8$ are hydrogen. In one embodiment, $R_2$ is not hydrogen. In one embodiment, $R_3$ is not hydrogen. In one embodiment, $R_6$ is not hydrogen. In one embodiment, $R_7$ is not hydrogen. In one embodiment, $R_3$ and $R_6$ are not hydrogen. In another embodiment, $R_2$ and $R_6$ are not hydrogen. In another embodiment, $R_3$ and $R_7$ are not hydrogen. In another embodiment, $R_2$ and $R_7$ are not hydrogen. In another embodiment, $R_2$ and $R_3$ are not hydrogen. In another embodiment, $R_6$ and $R_7$ are not hydrogen.

In one embodiment, at least one of $R_1$-$R_8$ is methyl, methoxymethylene, chloro, fluoro, bromo, hydroxy, or methoxy. In another embodiment, $R_2$ is methyl, methoxymethylene, chloro, fluoro, bromo, hydroxy, or methoxy. In another embodiment, $R_3$ is methyl, methoxymethylene, chloro, fluoro, bromo, hydroxy, or methoxy. In another embodiment, $R_6$ is methyl, methoxymethylene, chloro, fluoro, bromo, hydroxy, or methoxy. In another embodiment, $R_7$ is methyl, methoxymethylene, chloro, fluoro, bromo, hydroxy, or methoxy.

In another embodiment, at least two of $R_1$-$R_8$ are methyl, methoxymethylene, chloro, fluoro, bromo, hydroxy, or methoxy. In another embodiment, at least two of $R_1$-$R_8$ are methyl, methoxymethylene, chloro, fluoro, bromo, hydroxy, or methoxy; and Z is COOH. In another embodiment, at least two of $R_1$-$R_8$ are methyl, methoxymethylene, chloro, fluoro, bromo, hydroxy, or methoxy; $R_9$ and $R_{10}$ are hydrogen; and Z is COOH.

In one embodiment, $R_3$ and $R_6$ are both methyl, methoxy, methoxymethylene, methoxymethylene, hydroxy, chloro, fluoro, or bromo, and the remaining $R_1$-$R_2$, $R_4$-$R_5$, and $R_7$-$R_8$ are hydrogen. In another embodiment, $R_2$ and $R_6$ are both methyl, methoxy, methoxymethylene, hydroxy, chloro, fluoro, or bromo, and the remaining $R_1$, $R_3$-$R_5$, and $R_7$-$R_8$ are hydrogen. In one embodiment, $R_3$ and $R_7$ are both methyl, methoxy, methoxymethylene, hydroxy, chloro, fluoro, or bromo, and the remaining $R_1$-$R_2$, $R_4$-$R_6$, and $R_8$ are hydrogen. In one embodiment, $R_2$ and $R_7$ are both methyl, methoxy, hydroxy, methoxymethylene, chloro, fluoro, or bromo, and the remaining $R_1$, $R_3$-$R_6$, and $R_8$ are hydrogen. In one embodiment, $R_2$ and $R_3$ are both methyl, methoxy, hydroxy, methoxymethylene, chloro, fluoro, or bromo, and the remaining $R_1$ and $R_4$-$R_8$ are hydrogen.

In one embodiment, $R_6$ is methyl. In one embodiment, $R_6$ is methyl and $R_2$ or $R_3$ is methyl, methoxy, methoxymethylene, chloro, fluoro, or bromo. In another embodiment, $R_6$ is fluoro and $R_2$ or $R_3$ is methyl methoxymethylene, or methoxy. In one embodiment, $R_6$ is methoxy. In one embodiment, $R_6$ is methoxy and $R_2$ or $R_3$ is methyl, methoxy, methoxymethylene, hydroxy, chloro, fluoro, or bromo. In another embodiment, $R_6$ is fluoro and $R_2$ or $R_3$ is methoxy.

In one embodiment, $R_9$ and $R_{10}$, together with the carbon to which they are attached, are connected to form a spiro ring of size 3 to 7. In one embodiment, $R_9$ and $R_{10}$, together with the carbon to which they are attached are absent, and $R_{11}$ and $R_{12}$, together with the carbon to which they are attached, are connected to form a spiro ring of size 3 to 7. For example, $R_9$ and $R_{10}$ together with the carbon to which they are attached or $R_{11}$ and $R_{12}$ together with the carbon to which they are attached, are connected to form a spiro 3-membered cyclopropyl ring.

In one embodiment, $R_9$ and $R_{10}$ are hydrogen.

In one embodiment, $R_9$ and $R_{10}$ are methyl. In another embodiment, $R_9$ and $R_{10}$ are methyl, $R_6$ is hydrogen or halogen, and $R_1$-$R_5$, $R_7$-$R_8$ are hydrogen. In another embodiment, $R_9$ and $R_{10}$ are methyl, $R_6$ is hydrogen or halogen, $R_1$-$R_5$, $R_7$-$R_8$ are hydrogen, and Z is COOH.

In one embodiment, $R_9$ and $R_{10}$ are ethyl. In another embodiment, $R_9$ and $R_{10}$ are ethyl, $R_6$ is hydrogen or halogen, and $R_1$-$R_5$, $R_7$-$R_8$ are hydrogen. In another embodiment, $R_9$ and $R_{10}$ are ethyl, $R_6$ is hydrogen or halogen, $R_1$-$R_5$, $R_7$-$R_8$ are hydrogen, and Z is COOH.

In one embodiment, $R_9$ and $R_{10}$ and the carbon to which they are attached are connected to form a three-membered spiro (cyclopropyl) ring. In another embodiment, $R_9$ and $R_{10}$ and the carbon to which they are attached are connected to form a three-membered spiro (cyclopropyl) ring, $R_6$ is hydrogen or halogen, and $R_1$-$R_5$, $R_7$-$R_8$ are hydrogen. In another embodiment, $R_9$ and $R_{10}$ and the carbon to which they are attached are connected to form a three-membered spiro (cyclopropyl) ring, $R_6$ is hydrogen or halogen, and $R_1$-$R_5$, $R_7$-$R_8$ are hydrogen and Z is COOH.

In another embodiment, $R_9$ and $R_{10}$ are methyl, $R_6$ is methoxy, and $R_1$-$R_5$, $R_7$-$R_8$ are hydrogen. In another embodiment, $R_9$ and $R_{10}$ are methyl, $R_6$ is methoxy, $R_1$-$R_5$, $R_7$-$R_8$ are hydrogen, and Z is COOH.

In another embodiment, $R_9$ and $R_{10}$ are methyl, $R_6$ is methoxymethylene, and $R_1$-$R_5$, $R_7$-$R_8$ are hydrogen. In another embodiment, $R_9$ and $R_{10}$ are methyl, $R_6$ is methoxymethylene, $R_1$-$R_5$, $R_7$-$R_8$ are hydrogen, and Z is COOH.

In another embodiment, $R_9$ and $R_{10}$ are ethyl, $R_6$ is methoxy, and $R_1$-$R_5$, $R_7$-$R_8$ are hydrogen. In another embodiment, $R_9$ and $R_{10}$ are ethyl, $R_6$ is methoxy, $R_1$-$R_5$, $R_7$-$R_8$ are hydrogen, and Z is COOH.

In another embodiment, $R_9$ and $R_{10}$ and the carbon to which they are attached are connected to form a three-membered spiro (cyclopropyl) ring, $R_6$ is methoxy, and $R_1$-$R_5$, $R_7$-$R_8$ are hydrogen. In another embodiment, $R_9$ and $R_{10}$ and the carbon to which they are attached are connected to form a three-membered spiro (cyclopropyl) ring, $R_6$ is methoxy, and $R_1$-$R_5$, $R_7$-$R_8$ are hydrogen and Z is COOH.

In one embodiment $R_9$ and $R_{10}$ together with the carbon to which they are attached are absent.

In one embodiment, $R_{11}$ and $R_{12}$ are methyl. In another embodiment, $R_{11}$ and $R_{12}$ are methyl, $R_6$ is hydrogen or halogen, and $R_1$-$R_5$, $R_7$-$R_{10}$ are hydrogen. In another embodiment, $R_{11}$ and $R_{12}$ are methyl, $R_6$ is hydrogen or halogen, $R_1$-$R_5$, $R_7$-$R_{10}$ are hydrogen, and Z is COOH.

In one embodiment, $R_{11}$ and $R_{12}$ are ethyl. In another embodiment, $R_{11}$ and $R_{12}$ are ethyl, $R_6$ is hydrogen or halogen, and $R_1$-$R_5$, $R_7$-$R_{10}$ are hydrogen. In another embodiment, $R_{11}$ and $R_{12}$ are ethyl, $R_6$ is hydrogen or halogen, $R_1$-$R_5$, $R_7$-$R_{10}$ are hydrogen, and Z is COOH.

In one embodiment, $R_{11}$ and $R_{12}$ and the carbon to which they are attached are connected to form a three-membered spiro (cyclopropyl) ring. In another embodiment, $R_{11}$ and $R_{12}$ and the carbon to which they are attached are connected to form a three-membered spiro (cyclopropyl) ring, $R_6$ is hydrogen or halogen, and $R_1$-$R_5$, $R_7$-$R_{10}$ are hydrogen. In another embodiment, $R_{11}$ and $R_{12}$ and the carbon to which they are attached are connected to form a three-membered spiro (cyclopropyl) ring, $R_6$ is hydrogen or halogen, and $R_1$-$R_5$, $R_7$-$R_{10}$ are hydrogen and Z is COOH.

In one embodiment, $R_{11}$ and $R_{12}$ are methyl and $R_6$ is methoxy. In another embodiment, $R_{11}$ and $R_{12}$ are methyl, $R_6$ is methoxy, and $R_1$-$R_5$, $R_7$-$R_{10}$ are hydrogen. In another embodiment, $R_{11}$ and $R_{12}$ are methyl, $R_6$ is methoxy, $R_1$-$R_5$, $R_7$-$R_{10}$ are hydrogen, and Z is COOH.

In one embodiment, $R_{11}$ and $R_{12}$ are ethyl and $R_6$ is methoxy. In another embodiment, $R_{11}$ and $R_{12}$ are ethyl, $R_6$ is methoxy, and $R_1$-$R_5$, $R_7$-$R_{10}$ are hydrogen. In another embodiment, $R_{11}$ and $R_{12}$ are ethyl, $R_6$ is methoxy, $R_1$-$R_5$, $R_7$-$R_{10}$ are hydrogen, and Z is COOH.

In one embodiment, $R_{11}$ and $R_{12}$ and the carbon to which they are attached are connected to form a three-membered spiro (cyclopropyl) ring and $R_6$ is methoxy. In another embodiment, $R_{11}$ and $R_{12}$ and the carbon to which they are attached are connected to form a three-membered spiro (cyclopropyl) ring, $R_6$ is methoxy, and $R_1$-$R_5$, $R_7$-$R_{10}$ are hydrogen. In another embodiment, $R_{11}$ and $R_{12}$ and the carbon to which they are attached are connected to form a three-membered spiro (cyclopropyl) ring, $R_6$ is methoxy, and $R_1$-$R_5$, $R_7$-$R_{10}$ are hydrogen and Z is COOH.

In one embodiment, q is zero. In another embodiment, q is zero, and $R_9$ and $R_{10}$ together with the carbon to which they are attached are absent. In another embodiment, q is zero, $R_9$ and $R_{10}$ together with the carbon to which they are attached are absent, X and Y are absent. In another embodiment, q is zero, $R_9$ and $R_{10}$ together with the carbon to which they are attached are absent, X and Y are absent, and the sum of m, n, o, and p is 1 or 2.

Pharmaceutical compositions that include a compound of Formula I or a pharmaceutically acceptable salt thereof are also used in the methods of modulating sleep according to the invention.

In another aspect, the present invention provides a compound having the formula of Formula II:

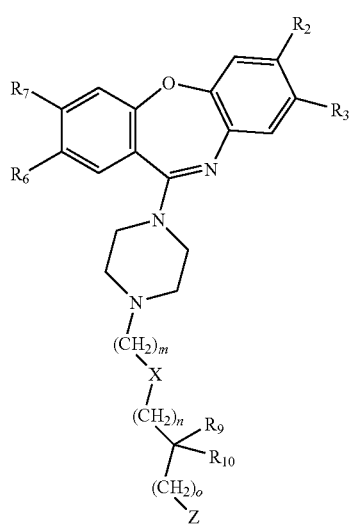

(II)

or a pharmaceutically effective salt thereof, wherein m, n, and o are, independently, 0, 1, 2, 3, 4, 5, or 6; X is absent, O, S, C(O), SO, or $SO_2$; $R_2$, $R_3$, $R_6$, and $R_7$ are, independently selected from H, F, Cl, Br, $CF_3$, $CH_3$, $CH_2CH_3$, $CH(CH_3)_2$, cyclopropyl, OH, $OCH_3$, $OCF_3$, $CH_2OCH_3$ and $CH_2OCH_2CH_3$; $R_9$, and $R_{10}$, are, independently, H, $C_1$-$C_6$ straight chain alkyl; $C_2$-$C_6$ branched alkyl, or $R_9$ and $R_{10}$ together with the carbon to which they are attached, are connected to form a spiro ring of size 3, 4, 5, 6, or 7 atoms; and Z is COOH, $COOR_{13}$ (where $R_{13}$ is $C_1$-$C_6$ alkyl) $CONHS(O)_2$-alkyl, $CONHS(O)_2$-heteroalkyl, $CONHS(O)_2$-aryl, CONHS$(O)_2$-heteroaryl, $S(O)_2$NHCO-alkyl, $S(O)_2$NHCO-heteroalkyl, $S(O)_2$NHCO-aryl, $S(O)_2$NHCO-heteroaryl, $CONHS(O)_2$NH-alkyl; $CONHS(O)_2$NH-heteroalkyl; $CONHS(O)_2$NH-aryl; $CONHS(O)_2$NH-heteroaryl; or tetrazole, provided that when Z is COOH or $COOR_{13}$, and $R_6$ is H or halogen, $R_1$-$R_5$ and $R_7$-$R_{12}$ are not each hydrogen, further provided that when m is zero, X is absent.

In one embodiment, Z is $CO_2H$ or tetrazole. In another embodiment, when Z is COOH, at least one of $R_2$, $R_3$, $R_6$, and $R_7$, and at least one of $R_9$-$R_{10}$, are not hydrogen. In one embodiment, o is zero.

In one embodiment, at least one of $R_2$, $R_3$, $R_6$, $R_7$, and at least one of $R_9$-$R_{10}$, are not hydrogen when Z is COOH. In one embodiment, $R_2$, $R_3$, and $R_7$ are each hydrogen and $R_6$ is not hydrogen or halogen. In one embodiment, $R_2$, $R_3$, and $R_7$, are each hydrogen, and $R_6$ is methyl, methoxy, or hydroxy.

In one embodiment, at least two of $R_2$, $R_3$, $R_6$, $R_7$ are not hydrogen, and the remaining $R_2$, $R_3$, $R_6$, $R_7$ are hydrogen. In another embodiment, at least three of $R_2$, $R_3$, $R_6$, $R_7$ are not hydrogen and the remaining $R_2$, $R_3$, $R_6$, $R_7$ are hydrogen. In one embodiment, $R_2$ is not hydrogen. In one embodiment, $R_3$ is not hydrogen. In one embodiment, $R_6$ is not hydrogen. In one embodiment, $R_7$ is not hydrogen. In one embodiment, $R_3$ and $R_6$ are not hydrogen. In another embodiment, $R_2$ and $R_6$ are not hydrogen. In another embodiment, $R_3$ and $R_7$ are not hydrogen.

In one embodiment, $R_9$ and $R_{10}$ are each methyl. In another embodiment, $R_9$ and $R_{10}$ are each ethyl. In another embodiment, $R_9$ and $R_{10}$ are each hydrogen.

In one embodiment, $R_9$ and $R_{10}$ and the carbon to which they are attached are connected to form a spiro ring of size from three to seven. For example, in one embodiment, $R_9$ and $R_{10}$ and the carbon to which they are attached are connected to form a three-membered spiro (cyclopropyl) ring.

In one embodiment, $R_9$ and $R_{10}$ are methyl, $R_6$ is hydrogen or halogen, and the remaining $R_2$, $R_3$, and $R_7$ are hydrogen. $R_9$ and $R_{10}$ are methyl, $R_6$ is hydrogen or halogen, and the remaining $R_2$, $R_3$, and $R_7$ are hydrogen, and Z is COOH.

In one embodiment, $R_9$ and $R_{10}$ are ethyl, $R_6$ is hydrogen or halogen, and the remaining $R_2$, $R_3$, and $R_7$ are hydrogen. In another embodiment, $R_9$ and $R_{10}$ are ethyl, $R_6$ is hydrogen or halogen, and the remaining $R_2$, $R_3$, and $R_7$ are hydrogen, and Z is COOH.

In one embodiment, $R_9$ and $R_{10}$ and the carbon to which they are attached are connected to form a three-membered spiro (cyclopropyl) ring. In another embodiment, $R_9$ and $R_{10}$ and the carbon to which they are attached are connected to form a three-membered spiro (cyclopropyl) ring, $R_6$ is hydrogen or halogen, and the remaining $R_2$, $R_3$, and $R_7$ are hydrogen. In another embodiment, $R_9$ and $R_{10}$ and the carbon to which they are attached are connected to form a three-membered spiro (cyclopropyl) ring, $R_6$ is hydrogen or halogen, and the remaining $R_2$, $R_3$, and $R_7$ are hydrogen, and Z is COOH.

In one embodiment, in the compound of Formula II, o is zero. In another embodiment, o is zero, and X is absent. In another embodiment, o is zero, X is absent, and the sum of m and n is 1 or 2.

Pharmaceutical compositions that include a compound of Formula II or a pharmaceutically acceptable salt thereof are also used in the methods of modulating sleep according to the invention.

In another aspect, the invention provides a compound having the formula of Formula III:

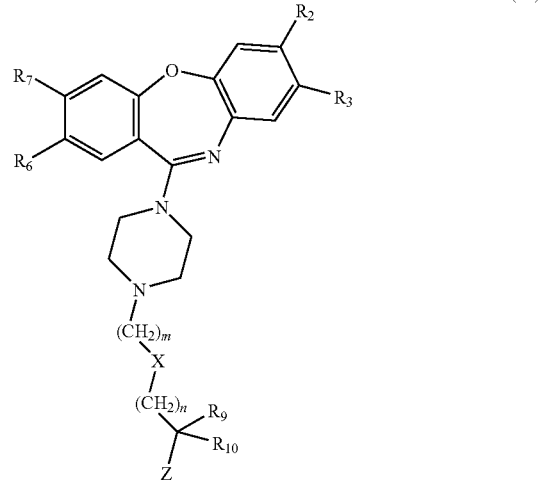

(III)

or a pharmaceutically effective salt thereof, wherein m and n are, independently, 0, 1, 2, 3, or 4, X is absent, O, or S; $R_2$, $R_3$, $R_6$, and $R_7$ are, independently, selected from H, F, Cl, Br, $CF_3$, $CH_3$, OH, $CH_2CH_3$, $CH(CH_3)_2$, $OCH_3$, $CH_2OCH_3$, and $CH_2OCH_2CH_3$; $R_9$, and $R_{10}$, are, independently, H, $C_1$-$C_6$ straight chain alkyl; $C_2$-$C_6$ branched alkyl, or $R_9$ and $R_{10}$, together with the carbon to which they are attached, are connected to form a spiro ring of size 3, 4, 5, 6, or 7; and Z is selected from $CO_2H$, $CONHS(O)_2$-alkyl, $CONHS(O)_2$-cycloalkyl, $CONHS(O)_2$-heteroalkyl, $CONHS(O)_2$-aryl, $CONHS(O)_2$-heteroaryl, and tetrazole; provided that when Z is COOH and $R_6$ is H, F, Cl, or Br, then $R_2$, $R_3$, $R_7$, and $R_9$-$R_{10}$ are not each hydrogen, further provided that when m is zero, X is absent.

In one embodiment, Z is $CO_2H$ or tetrazole. In one embodiment, m is zero. In one embodiment, at least one of $R_2$, $R_3$, $R_6$, $R_7$, and at least one of $R_9$-$R_{10}$ are not hydrogen when Z is COOH. In one embodiment, $R_2$, $R_3$, and $R_7$ are each hydrogen and $R_6$ is not hydrogen or halogen. In one embodiment, $R_2$, $R_3$, and $R_7$, are each hydrogen, and $R_6$ is methyl, methoxy, or hydroxy.

In one embodiment, $R_2$, $R_3$, and $R_7$ are each hydrogen and $R_6$ is not hydrogen or halogen. In one embodiment, $R_2$, $R_3$, and $R_7$, are each hydrogen, and $R_6$ is methyl, methoxymethylene, methoxy, or hydroxy.

In one embodiment, at least two of $R_2$, $R_3$, $R_6$, and $R_7$ are not hydrogen, and the remaining $R_2$, $R_3$, $R_6$, and $R_7$ are hydrogen. In another embodiment, at least three of $R_2$, $R_3$, $R_6$, and $R_7$ are not hydrogen and the remaining $R_2$, $R_3$, $R_6$, and $R_7$ are hydrogen. In one embodiment, $R_2$ is not hydrogen. In one embodiment, $R_3$ is not hydrogen. In one embodiment, $R_6$ is not hydrogen. In one embodiment, $R_7$ is not hydrogen. In one embodiment, $R_3$ and $R_6$ are not hydrogen. In another embodiment, $R_2$ and $R_6$ are not hydrogen. In another embodiment, $R_3$ and $R_7$ are not hydrogen.

In one embodiment, $R_9$ and $R_{10}$ are each methyl. In another embodiment, $R_9$ and $R_{10}$ are each ethyl. In another embodiment, $R_9$ and $R_{10}$ are each hydrogen.

In one embodiment, $R_9$ and $R_{10}$ and the carbon to which they are attached are connected to form a spiro ring of size from three to seven. For example, in one embodiment, $R_9$ and $R_{10}$ and the carbon to which they are attached are connected to form a three-membered spiro (cyclopropyl) ring.

In one embodiment, $R_9$ and $R_{10}$ are methyl, $R_6$ is hydrogen or halogen, and the remaining $R_2$, $R_3$, and $R_7$ are hydrogen. In another embodiment, $R_9$ and $R_{10}$ are methyl, $R_6$ is hydrogen or halogen, and the remaining $R_2$, $R_3$, and $R_7$ are hydrogen, and Z is COOH.

In one embodiment, $R_9$ and $R_{10}$ are ethyl, $R_6$ is hydrogen or halogen, and the remaining $R_2$, $R_3$, and $R_7$ are hydrogen. In another embodiment, $R_9$ and $R_{10}$ are ethyl, $R_6$ is hydrogen or halogen, and the remaining $R_2$, $R_3$, and $R_7$ are hydrogen, and Z is COOH.

In one embodiment, $R_9$ and $R_{10}$ and the carbon to which they are attached are connected to form a three-membered spiro (cyclopropyl) ring. In another embodiment, $R_9$ and $R_{10}$ and the carbon to which they are attached are connected to form a three-membered spiro (cyclopropyl) ring, $R_6$ is hydrogen or halogen, and the remaining $R_2$, $R_3$, and $R_7$ are hydrogen. In another embodiment, $R_9$ and $R_{10}$ and the carbon to which they are attached are connected to form a three-membered spiro (cyclopropyl) ring, $R_6$ is hydrogen or halogen, and the remaining $R_2$, $R_3$, and $R_7$ are hydrogen, and Z is COOH.

In one embodiment, in the compound of Formula III, X is absent. In another embodiment, X is absent, and the sum of m and n is 1 or 2.

Pharmaceutical compositions that include a compound of Formula III or a pharmaceutically acceptable salt thereof are also used in the methods of modulating sleep according to the invention.

In another aspect, the invention provides a compound having the formula of Formula IV:

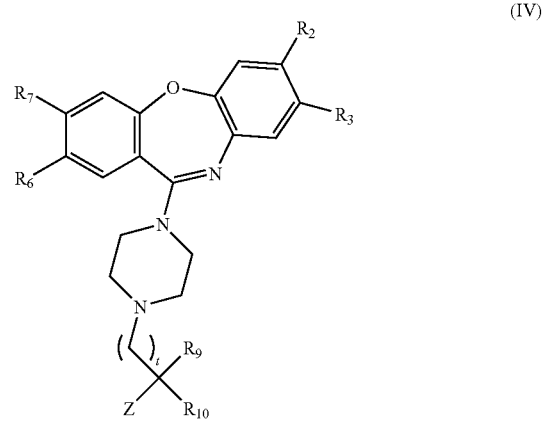

(IV)

or a pharmaceutically effective salt thereof wherein t is 1, 2, 3, or 4; $R_2$, $R_3$ and $R_6$ are, independently, H, F, Cl, Br, $CF_3$, $CH_3$, OH, $OCH_3$, $CH_2OCH_3$, or $CH_2OCH_2CH_3$; $R_9$-$R_{10}$ are H, $CH_3$, $CH_2CH_3$, or $R_9$ and $R_{10}$, together with the carbon to which they are attached, are connected to form a spiro ring of size 3, 4, 5, 6, or 7 atoms; and Z is selected from $CO_2H$, $CONHS(O)_2$-alkyl, $CONHS(O)_2$-cycloalkyl, $CONHS(O)_2$-heteroalkyl, and tetrazole; provided that when Z is COOH and $R_6$ is H, F, Cl, or Br, then $R_2$, $R_3$, $R_7$, and $R_9$-$R_{10}$ are not each hydrogen, further provided that when m is zero, X is absent.

In one embodiment, the compounds have t=1 or 2.

Pharmaceutical compositions that include a compound of Formula IV or a pharmaceutically acceptable salt thereof are also used in the methods of modulating sleep according to the invention.

In one embodiment, Z is $CO_2H$, sulfonamide, sulfamide, or tetrazole. In another embodiment, when Z is COOH, at least one of $R_2$, $R_3$, and $R_7$, and at least one of $R_9$-$R_{10}$, are not hydrogen.

In one embodiment, $R_9$ and $R_{10}$ are each methyl. In another embodiment, $R_9$ and $R_{10}$ are each ethyl. In one embodiment, $R_9$ and $R_{10}$ and the carbon to which they are attached are connected to form a spiro ring of size from three to seven. For example, in one embodiment, $R_9$ and $R_{10}$ and the carbon to which they are attached are connected to form a three-membered spiro (cyclopropyl) ring.

In one embodiment, $R_9$ and $R_{10}$ are methyl; $R_6$ is hydrogen or halogen; and $R_2$ $R_3$ and $R_7$ are hydrogen. In another embodiment, $R_9$ and $R_{10}$ are methyl; $R_6$ is hydrogen or halogen; and $R_2$ $R_3$ and $R_7$ are hydrogen; and Z is COOH.

In one embodiment, $R_9$ and $R_{10}$ are ethyl; $R_6$ is hydrogen or halogen; and $R_2$, $R_3$, and $R_7$ are hydrogen. In another embodiment, $R_9$ and $R_{10}$ are methyl; $R_6$ is hydrogen or halogen; and $R_2$, $R_3$, and $R_7$ are hydrogen; and Z is COOH.

In one embodiment, $R_9$ and $R_{10}$ and the carbon to which they are attached are connected to form a three-membered spiro (cyclopropyl) ring. In another embodiment, R$_9$ and R$_{10}$ and the carbon to which they are attached are connected to form a three-membered spiro (cyclopropyl) ring, R$_6$ is hydrogen or halogen; and R$_2$, R$_3$, and R$_7$ are hydrogen. In another embodiment, R$_9$ and R$_{10}$ and the carbon to which they are attached are connected to form a three-membered spiro (cyclopropyl) ring, R$_6$ is hydrogen or halogen; and R$_2$, R$_3$, and R$_7$ are hydrogen; and Z is COOH.

Pharmaceutical compositions that include a compound of Formula IV or a pharmaceutically acceptable salt thereof are also used in the methods of modulating sleep according to the invention.

In one embodiment, the compound of Formula IV is IVa, IVb, IVc, IVd or IVe. For example, when R$_9$ and R$_{10}$ are methyl, compounds have the general formula IVa:

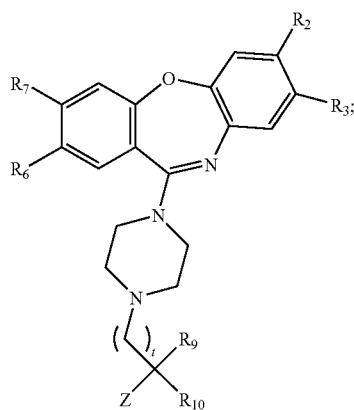
(IVa)

when R$_9$ and R$_{10}$ are connected to form a 3 membered spiro ring (cyclopropyl), compounds have the general formula IVb:

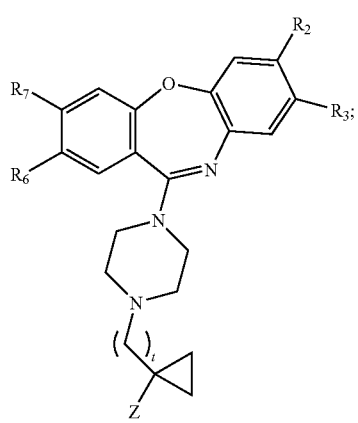
(IVb)

when R$_9$ and R$_{10}$ are ethyl, compounds have the general formula IVc:

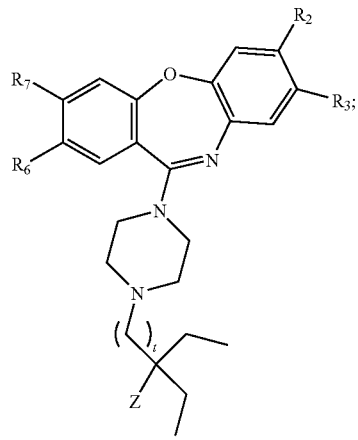
(IVc)

when R$_9$ and R$_{10}$ are ethyl, and the C-1 carbons are connected to form a 3 membered spiro ring (cyclopropyl), compounds have the general formula IVd:

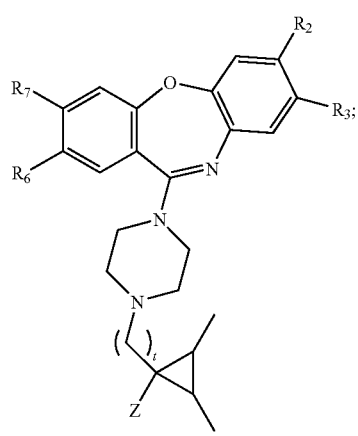
(IVd)

and when and R$_9$ and R$_{10}$ are hydrogen, compounds have the general formula IVe:

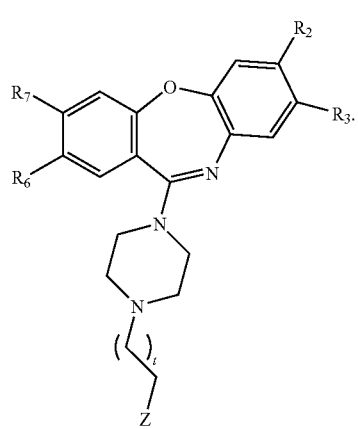
(IVe)

Some representative compounds of the invention are shown in Table 1.

TABLE 1

Loxapine derivatives

| Cmpd # | R$_2$ | R$_3$ | R$_6$ | R$_7$ | R$_9$, R$_{10}$ | T | Size Ring | Z |
|---|---|---|---|---|---|---|---|---|
| 1 | H | H | H | H | CH$_3$ | 1 | none | COOH |
| 2 | H | H | H | H | CH$_3$ | 1 | 3 | COOH |
| 3 | H | H | H | H | CH$_3$ | 2 | none | COOH |
| 4 | H | H | F | H | CH$_3$ | 1 | none | COOH |
| 5 | H | H | Cl | H | CH$_3$ | 1 | none | COOH |
| 6 | H | H | Cl | H | CH$_3$ | 2 | none | COOH |
| 7 | H | H | Cl | H | CH$_3$ | 1 | 3 | COOH |
| 8 | H | H | Br | H | CH$_3$ | 1 | none | COOH |
| 9 | H | H | Br | H | CH$_3$ | 1 | 3 | COOH |
| 10 | H | H | CH$_3$ | H | CH$_3$ | 1 | none | COOH |
| 11 | H | H | CH$_3$ | H | CH$_3$ | 2 | none | COOH |
| 12 | H | H | OCH$_3$ | H | CH$_3$ | 1 | none | COOH |
| 13 | H | H | OCH$_3$ | H | CH$_3$ | 2 | none | COOH |
| 14 | H | H | OH | H | CH$_3$ | 1 | none | COOH |
| 15 | H | F | H | H | CH$_3$ | 1 | none | COOH |
| 16 | H | F | CH$_3$ | H | CH$_3$ | 1 | none | COOH |
| 17 | H | Br | H | H | CH$_3$ | 1 | none | COOH |
| 18 | H | Br | Br | H | CH$_3$ | 1 | none | COOH |
| 19 | H | CH$_3$ | H | H | CH$_3$ | 1 | none | COOH |
| 20 | H | CH$_3$ | CH$_3$ | H | CH$_3$ | 1 | none | COOH |
| 21 | H | OCH$_3$ | H | H | CH$_3$ | 1 | none | COOH |
| 22 | H | OCH$_3$ | F | H | CH$_3$ | 1 | none | COOH |
| 23 | H | OCH$_3$ | OCH$_3$ | H | CH$_3$ | 1 | none | COOH |
| 24 | H | OH | H | H | CH$_3$ | 1 | none | COOH |
| 25 | H | OH | OH | H | CH$_3$ | 1 | none | COOH |
| 26 | F | H | H | H | CH$_3$ | 1 | none | COOH |
| 27 | F | H | CH$_3$ | H | CH$_3$ | 1 | none | COOH |
| 28 | Br | H | H | H | CH$_3$ | 1 | none | COOH |
| 29 | Br | H | Br | H | CH$_3$ | 1 | none | COOH |
| 30 | CH$_3$ | H | H | H | CH$_3$ | 1 | none | COOH |
| 31 | CH$_3$ | H | CH$_3$ | H | CH$_3$ | 1 | none | COOH |
| 32 | OCH$_3$ | H | H | H | CH$_3$ | 1 | none | COOH |
| 33 | OCH$_3$ | H | F | H | CH$_3$ | 1 | none | COOH |
| 34 | OCH$_3$ | H | CH$_3$ | H | CH$_3$ | 1 | none | COOH |
| 35 | OCH3 | H | OCH$_3$ | H | CH$_3$ | 1 | none | COOH |
| 36 | OCH$_3$ | CH$_3$ | H | H | CH$_3$ | 1 | none | COOH |
| 37 | OH | H | H | H | CH$_3$ | 1 | none | COOH |
| 38 | OH | H | OH | H | CH$_3$ | 1 | none | COOH |
| 39 | H | H | H | OCH$_3$ | CH$_3$ | 1 | none | COOH |
| 40 | H | H | H | H | CH$_3$ | 1 | none | CONHSO$_2$CH$_3$ |
| 41 | H | H | H | H | CH$_3$ | 1 | none | tetrazole |
| 42 | H | OCH$_3$ | H | OCH$_3$ | CH$_3$ | 1 | none | COOH |
| 43 | H | OCH$_3$ | CH$_3$ | H | CH$_3$ | 2 | none | COOH |
| 44 | H | Br | H | CH$_3$ | CH$_3$ | 1 | none | COOH |
| 45 | H | H | H | Br | CH$_3$ | 1 | none | COOH |
| 46 | H | H | H | CH$_3$ | CH$_3$ | 1 | none | COOH |
| 47 | H | F | Br | H | CH$_3$ | 1 | none | COOH |
| 48 | H | F | OCH$_3$ | H | CH$_3$ | 1 | none | COOH |
| 49 | H | Br | H | Br | CH$_3$ | 1 | none | COOH |
| 50 | H | Br | CH$_3$ | H | CH$_3$ | 1 | none | COOH |
| 51 | H | Br | OCH$_3$ | H | CH$_3$ | 1 | none | COOH |
| 52 | H | CH$_3$ | H | CH$_3$ | CH$_3$ | 1 | none | COOH |
| 53 | H | CH$_3$ | F | H | CH$_3$ | 1 | none | COOH |
| 54 | H | CH$_3$ | OCH$_3$ | H | CH$_3$ | 1 | none | COOH |
| 55 | H | OCH$_3$ | H | CH$_3$ | CH$_3$ | 1 | none | COOH |
| 56 | H | OCH$_3$ | CH$_3$ | H | CH$_3$ | 1 | none | COOH |
| 57 | CH$_3$ | H | Br | H | CH$_3$ | 1 | none | COOH |
| 58 | CH$_3$ | H | OCH$_3$ | H | CH$_3$ | 1 | none | COOH |
| 59 | H | H | CH$_3$ | H | H | 1 | none | COOH |
| 60 | H | H | CH$_3$ | H | H | 2 | none | COOH |
| 61 | H | H | OCH$_3$ | H | H | 1 | none | COOH |
| 62 | H | H | OCH$_3$ | H | H | 2 | none | COOH |
| 63 | H | H | OCH$_3$ | H | CH$_3$ | 1 | 3 | COOH |
| 64 | H | Br | Br | H | CH$_3$ | 2 | none | COOH |
| 65 | H | CH$_3$ | Br | H | CH$_3$ | 1 | none | COOH |
| 66 | H | OH | OH | H | CH$_3$ | 2 | none | COOH |
| 67 | H | OCH$_3$ | H | F | CH$_3$ | 1 | none | COOH |
| 68 | H | CH$_3$ | H | F | CH$_3$ | 1 | none | COOH |
| 69 | H | H | H | F | CH$_3$ | 1 | none | COOH |
| 70 | H | H | OCH$_3$ | H | CH$_3$ | 1 | none | tetrazole |
| 71 | H | H | OCH$_3$ | H | CH$_3$ | 1 | none | CONHSO$_2$CH$_3$ |
| 72 | Br | H | OCH$_3$ | H | CH$_3$ | 1 | none | COOH |
| 73 | OH | H | OCH$_3$ | H | CH$_3$ | 1 | none | COOH |
| 74 | H | H | OCH$_3$ | H | H | 1 | none | tetrazole |

TABLE 1-continued

Loxapine derivatives

| Cmpd # | $R_2$ | $R_3$ | $R_6$ | $R_7$ | $R_9, R_{10}$ | T | Size Ring | Z |
|---|---|---|---|---|---|---|---|---|
| 75 | H | H | OCH$_3$ | H | H | 1 | none | CONHSO$_2$CH$_3$ |
| 76 | H | H | OCH$_3$ | H | H | 2 | none | tetrazole |
| 77 | H | H | OCH$_3$ | H | H | 2 | none | CONHSO$_2$CH$_3$ |
| 78 | H | H | OCH$_3$ | H | CH$_3$ | 2 | none | tetrazole |
| 79 | H | H | OCH$_3$ | H | CH$_3$ | 2 | none | CONHSO$_2$CH$_3$ |
| 80 | H | H | OCH$_3$ | H | CH$_3$ | 1 | 3 | tetrazole |
| 81 | H | H | OCH$_3$ | H | CH$_3$ | 1 | 3 | CONHSO$_2$CH$_3$ |
| 82 | H | H | OCH$_3$ | H | CH$_3$ | 2 | 3 | tetrazole |
| 83 | H | H | OCH$_3$ | H | CH$_3$ | 2 | 3 | CONHSO$_2$CH$_3$ |
| 84 | H | H | OCH$_3$ | H | CH$_3$ | 2 | 3 | COOH |
| 85 | H | OCH$_3$ | F | H | CH$_3$ | 1 | none | COOH |
| 86 | H | Br | H | OCH$_3$ | CH$_3$ | 1 | none | COOH |
| 87 | H | CH$_3$ | H | OCH$_3$ | CH$_3$ |  | none | COOH |
| 88 | CH$_3$ | H | F | H | CH$_3$ |  | none | COOH |

Some examples include:

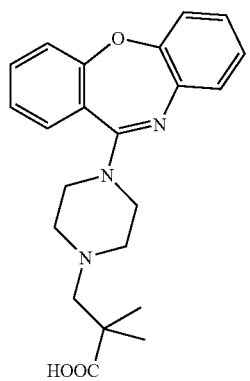

Compound 1

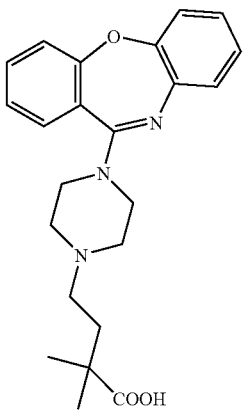

Compound 3

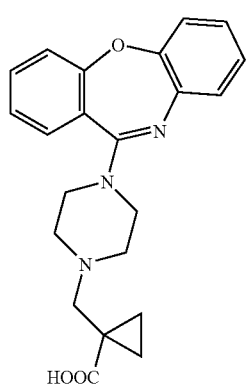

Compound 2

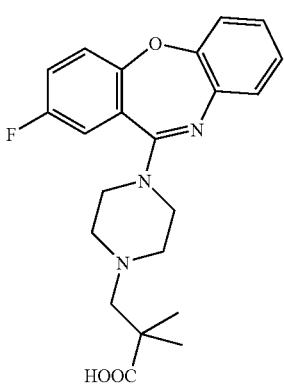

Compound 4

-continued
Compound 5
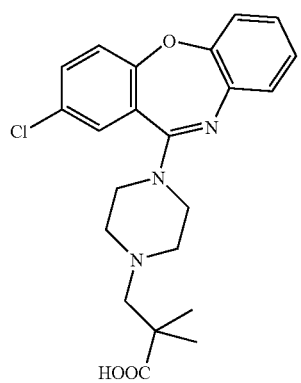
Compound 6
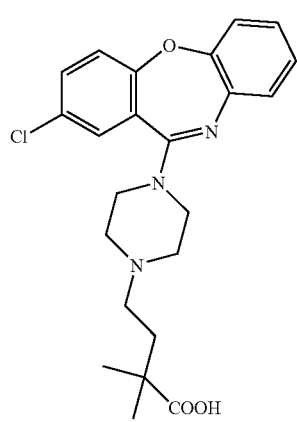
Compound 7
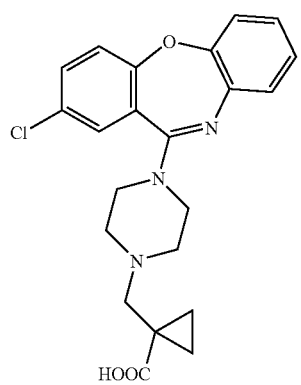
Compound 8
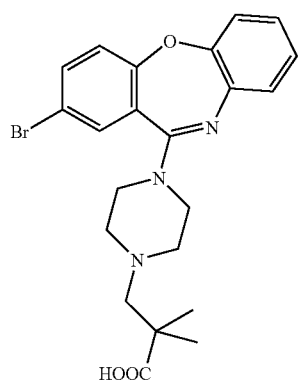
-continued
Compound 9
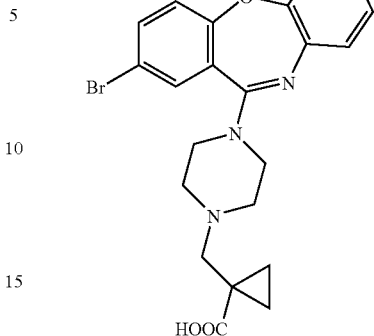
Compound 10
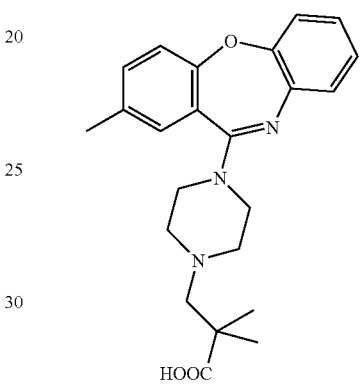
Compound 11
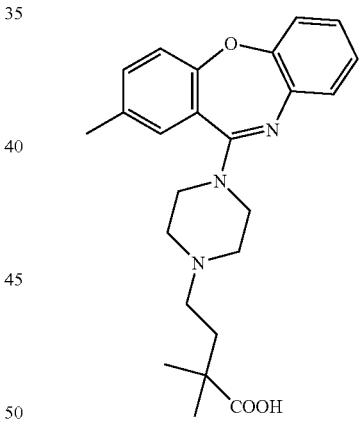
Compound 12
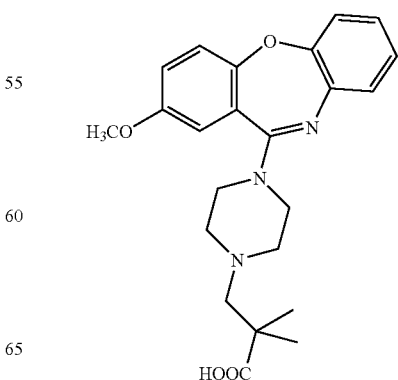

-continued
Compound 13
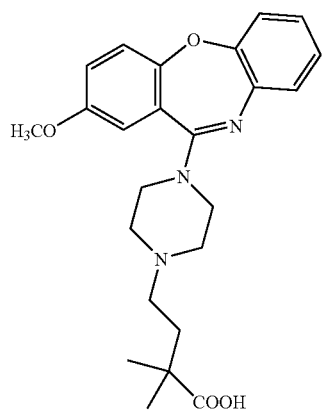
Compound 14
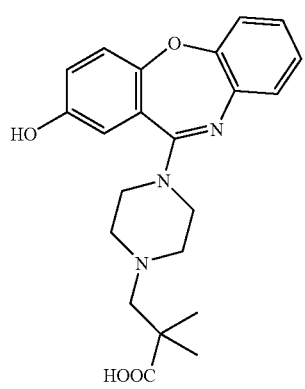
Compound 15
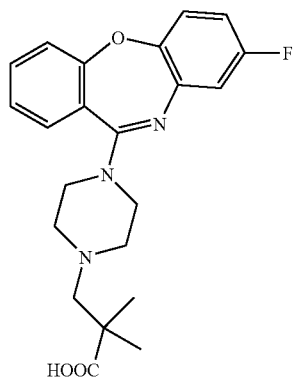
Compound 16
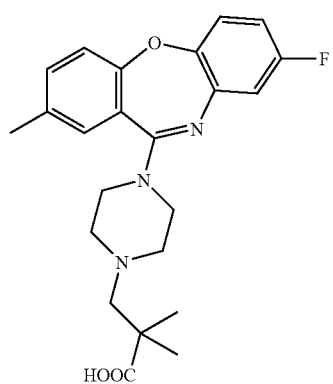
-continued
Compound 17
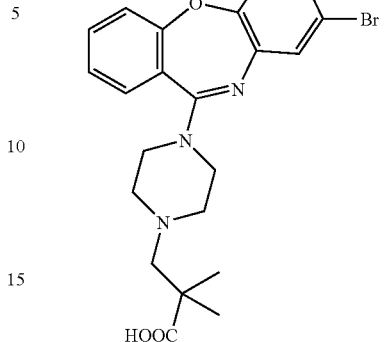
Compound 18
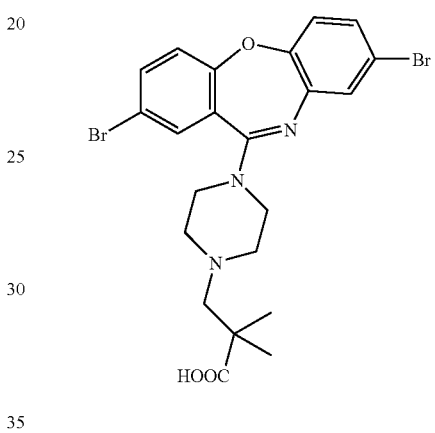
Compound 19
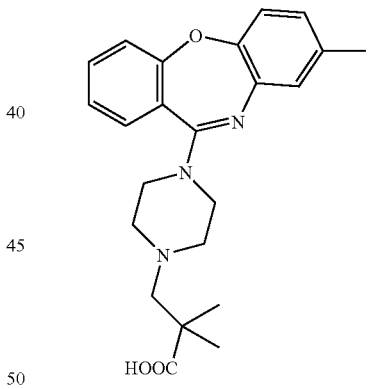
Compound 20
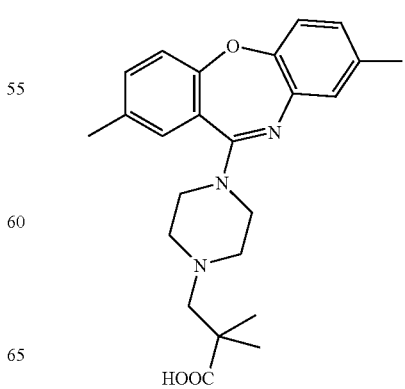

-continued
Compound 21
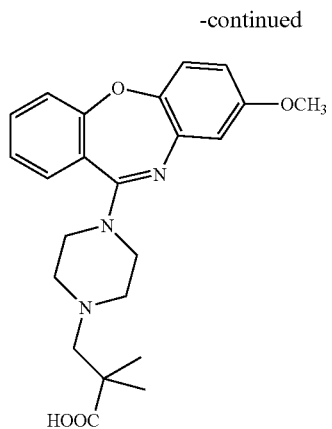
Compound 22
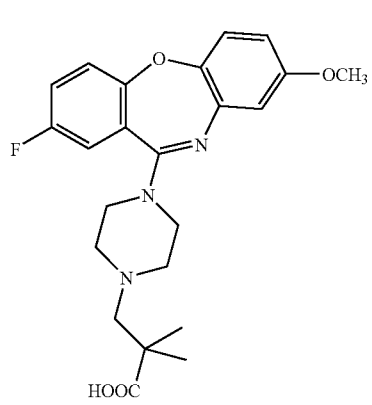
Compound 23
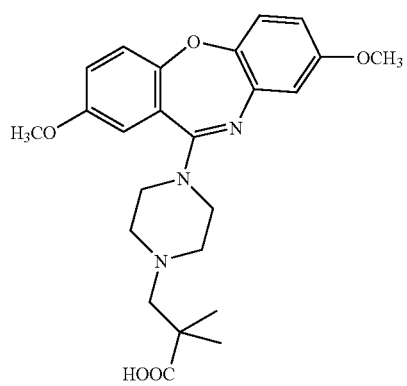
Compound 24
-continued
Compound 25
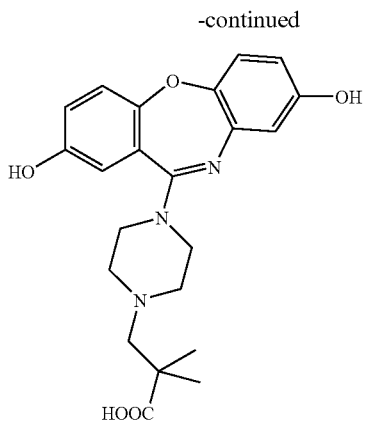
Compound 26
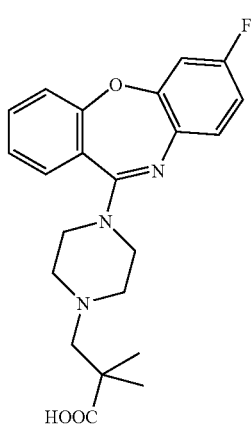
Compound 27
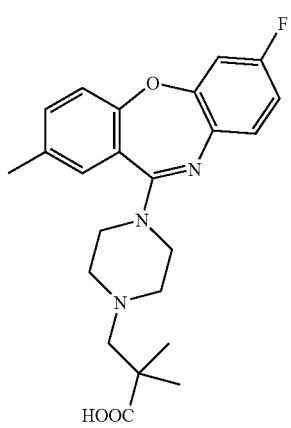
Compound 28
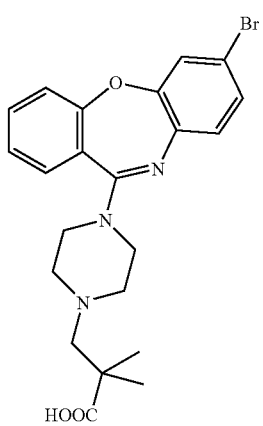

Compound 29
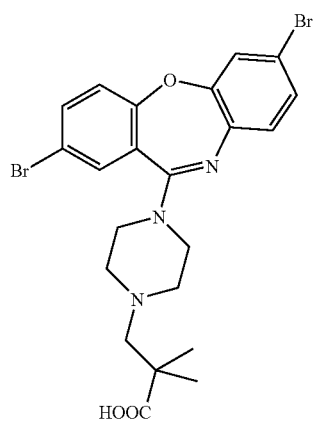
Compound 30
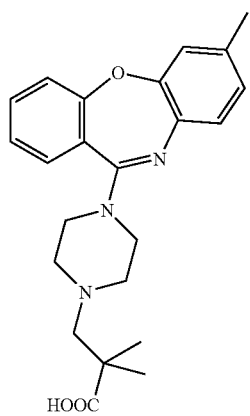
Compound 31
Compound 32
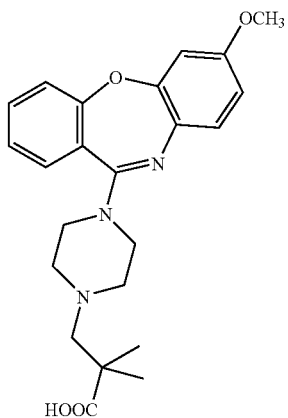
Compound 33
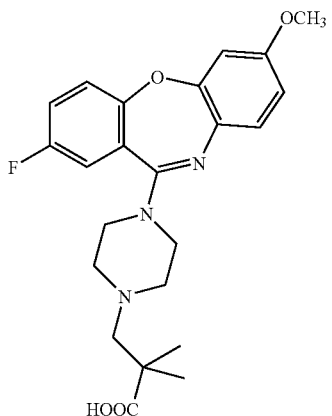
Compound 34
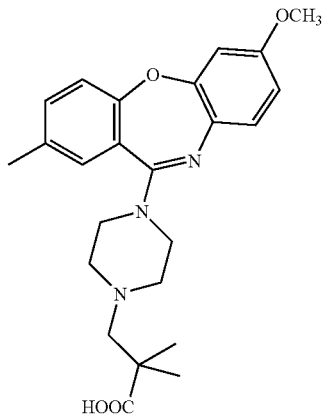

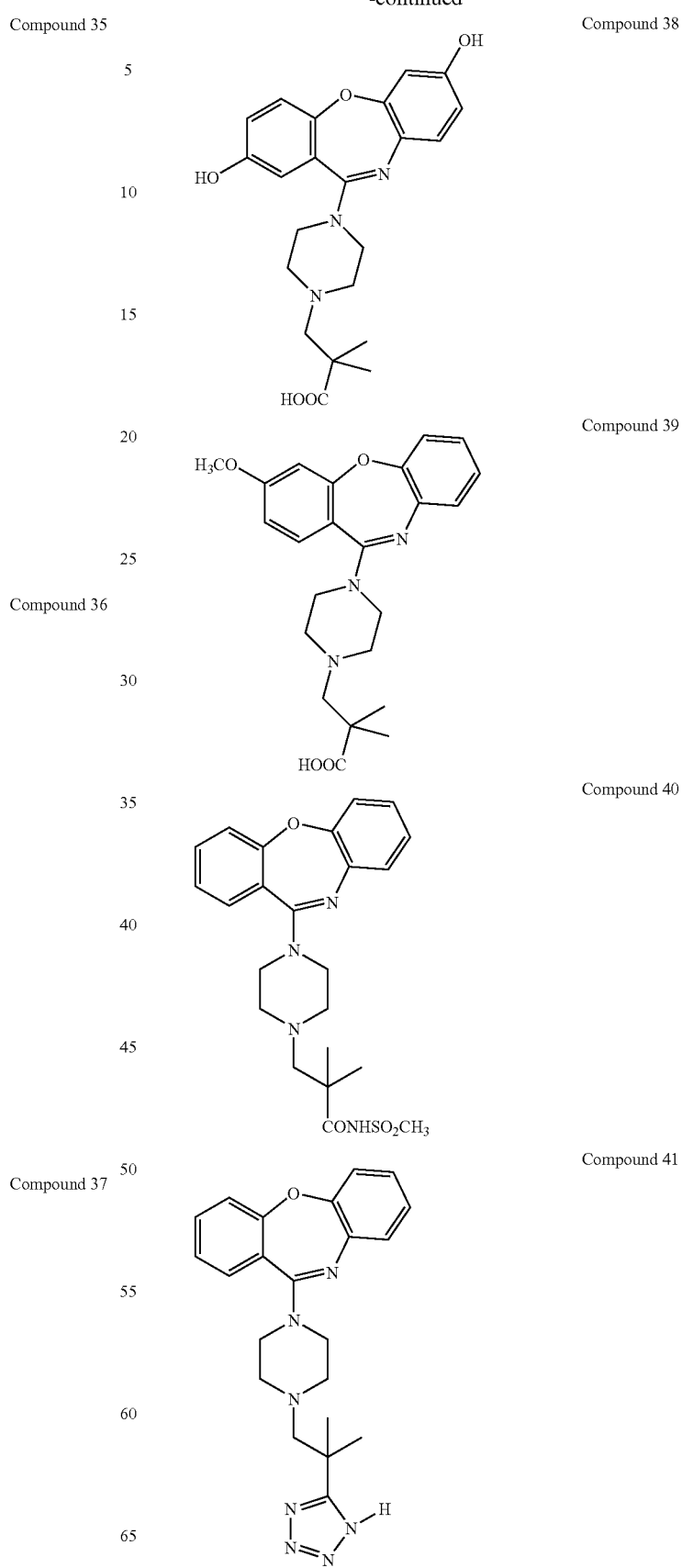
Compound 35
Compound 36
Compound 37
Compound 38
Compound 39
Compound 40
Compound 41

-continued
Compound 42
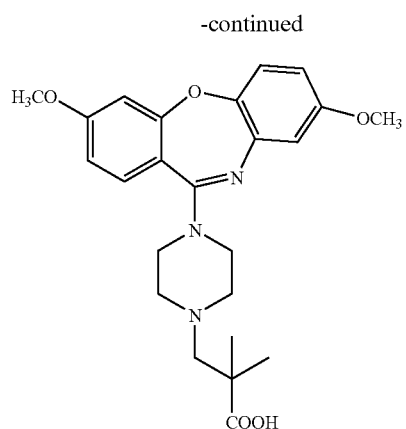
Compound 43
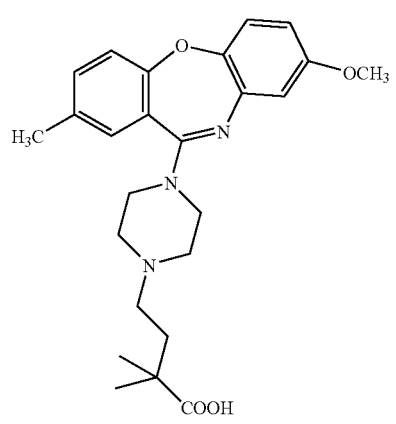
Compound 44
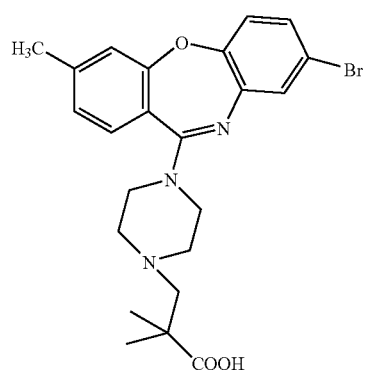
Compound 45
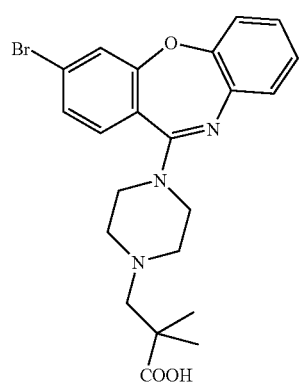
-continued
Compound 46
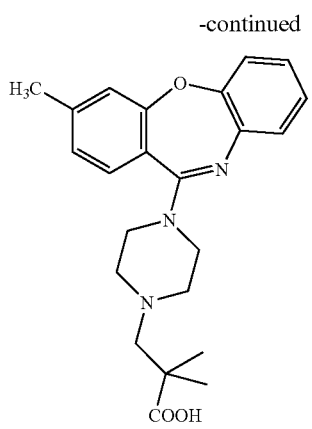
Compound 47
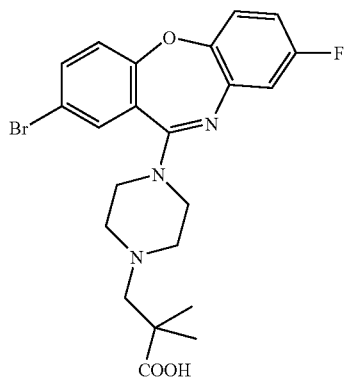
Compound 48
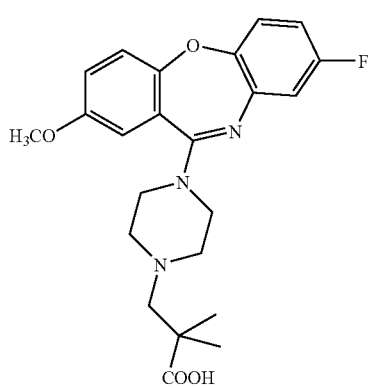
Compound 49
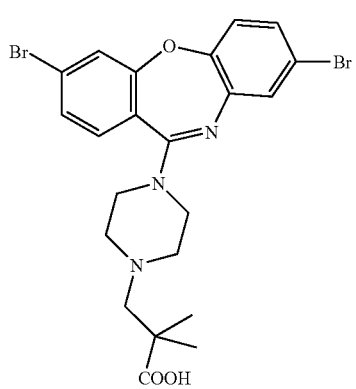

-continued
Compound 50
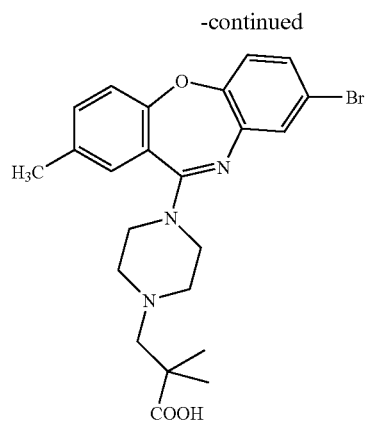
Compound 51
Compound 52
Compound 53
-continued
Compound 54
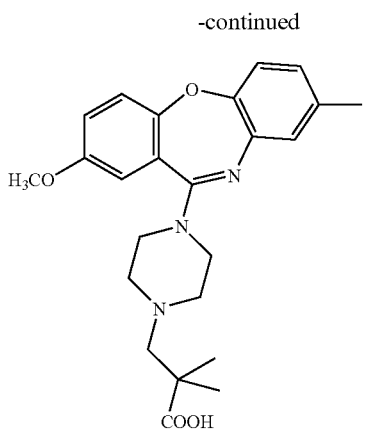
Compound 55
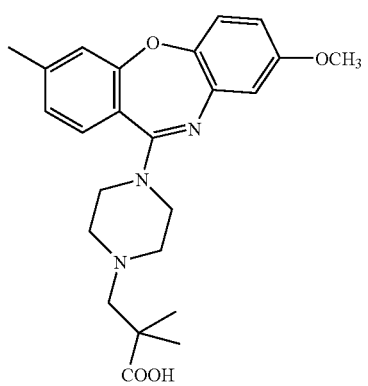
Compound 56
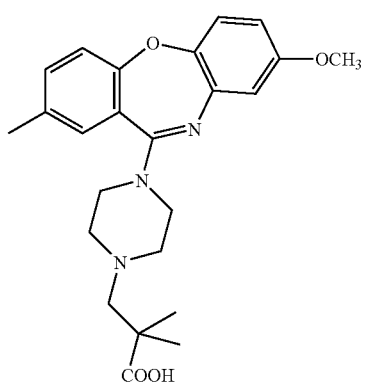
Compound 57
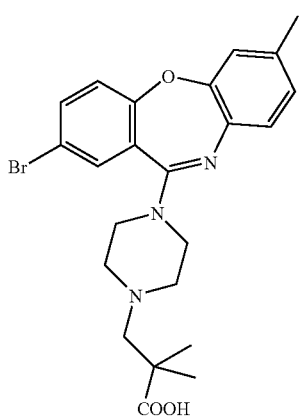

Compound 58
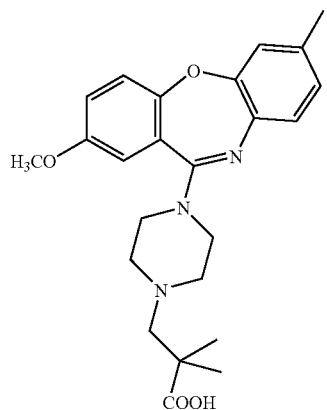
Compound 59
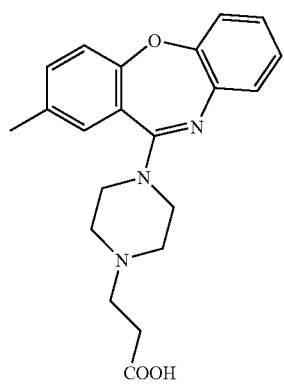
Compound 60
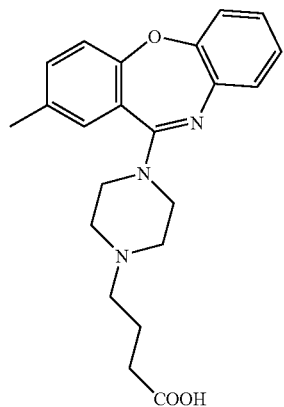
Compound 61
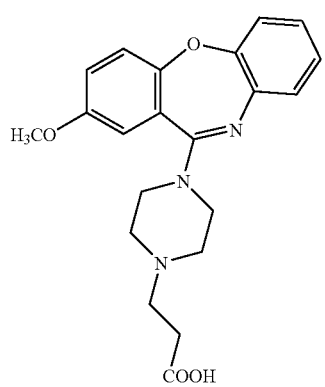
Compound 62
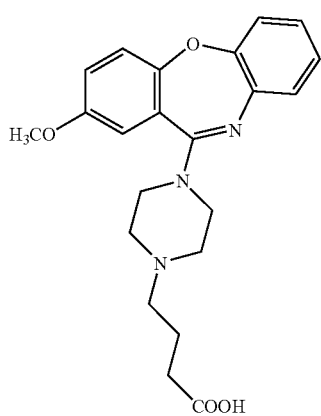
Compound 63
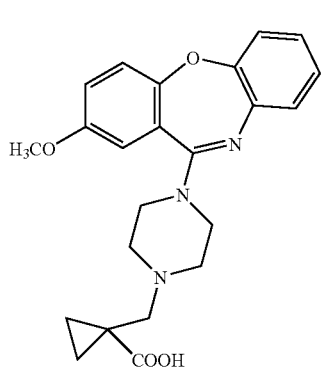
Compound 64
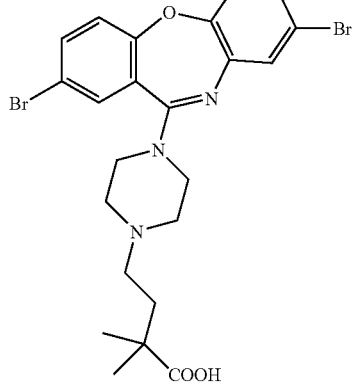
Compound 65
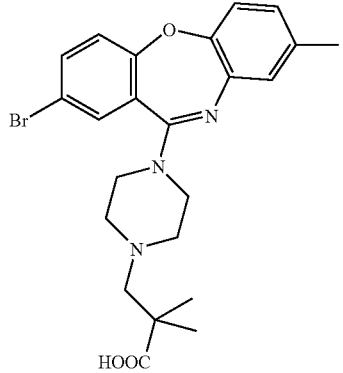

-continued
Compound 66
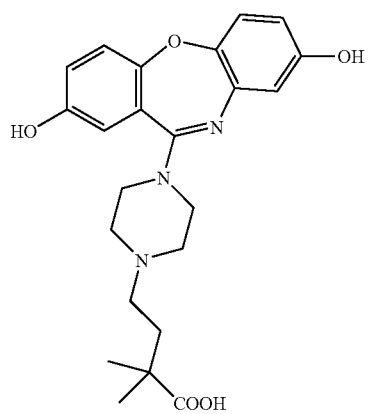
Compound 67
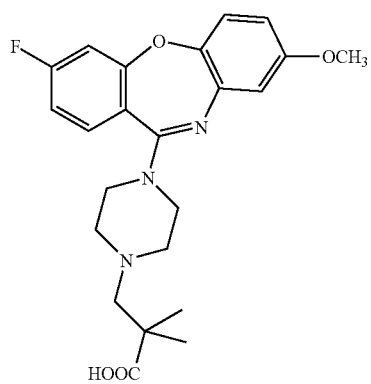
Compound 68
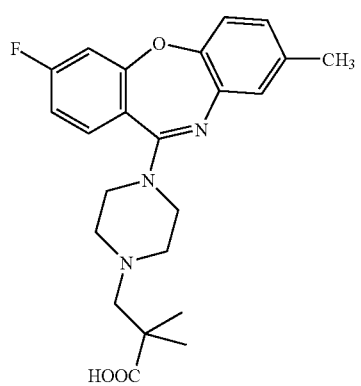
Compound 69
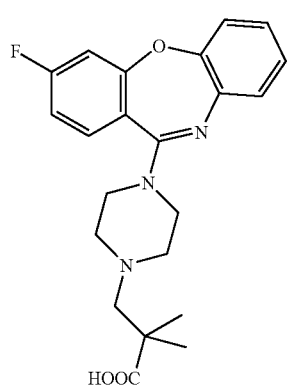
-continued
Compound 70
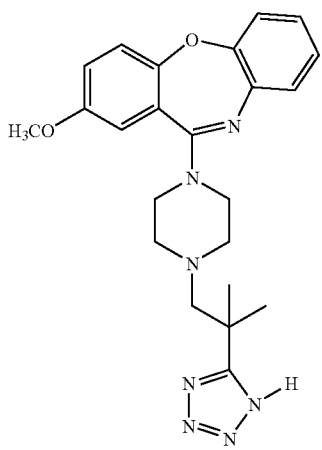
Compound 71
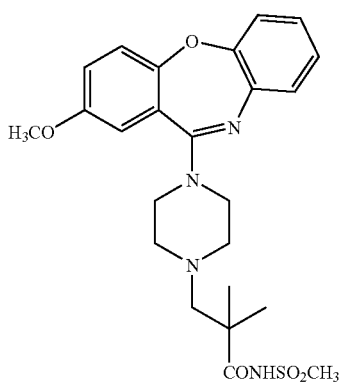
Compound 72
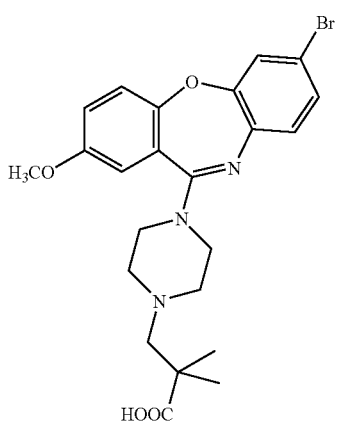

-continued
Compound 73
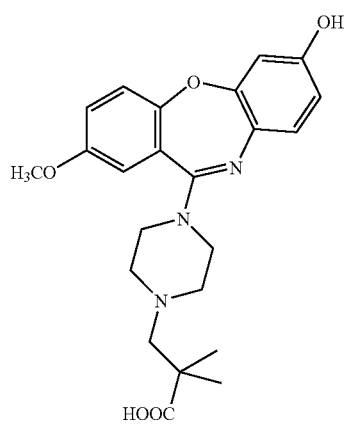
Compound 74
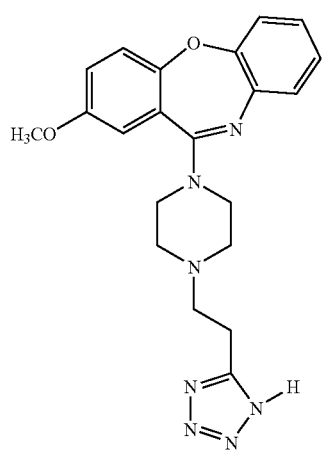
Compound 75
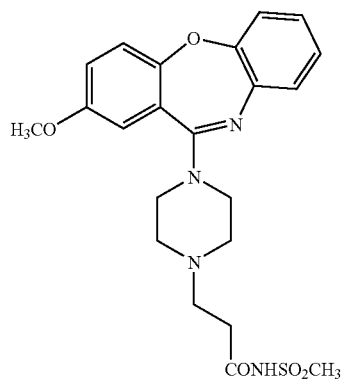
-continued
Compound 76
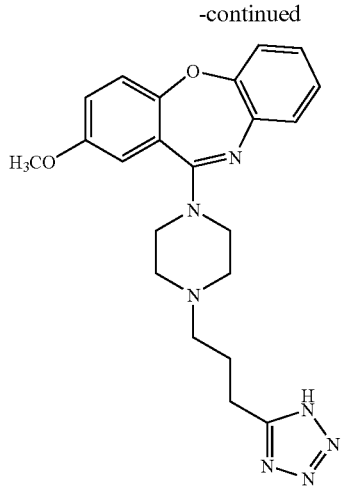
Compound 77
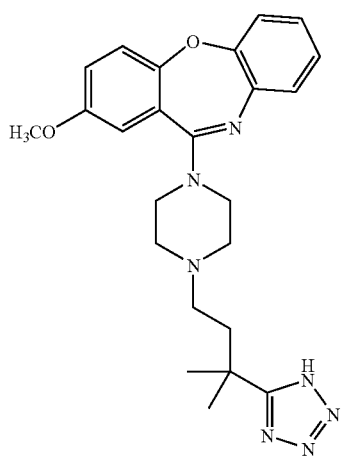
Compound 78

-continued
Compound 79
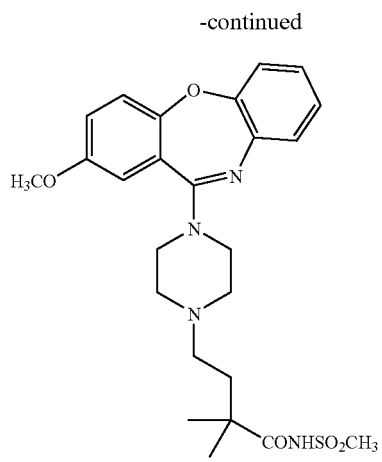
Compound 80
Compound 81
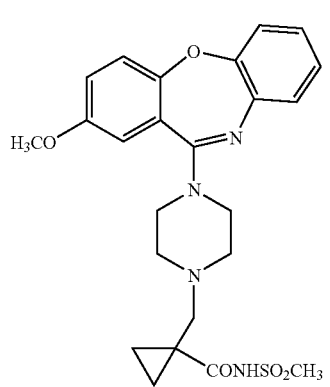
-continued
Compound 82
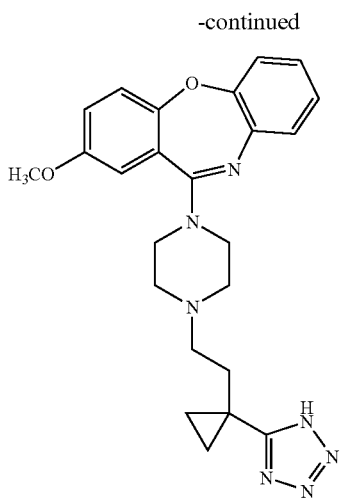
Compound 83
Compound 84
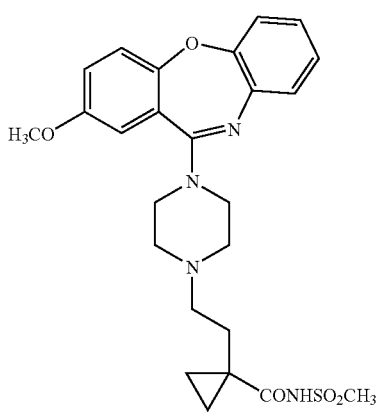
Compound 85
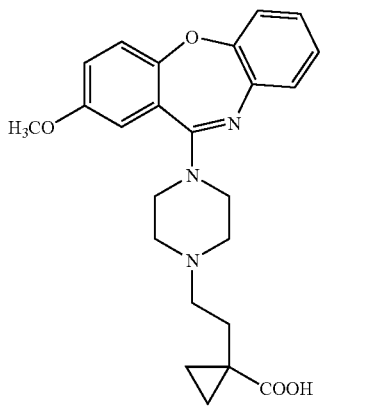

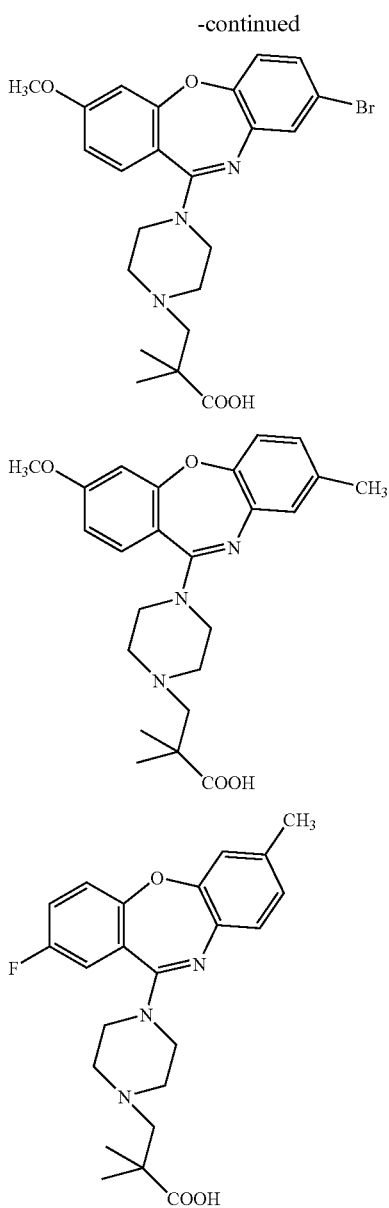

Compound 86

Compound 87

Compound 88

In general, in another aspect, the present invention relates to the use of loxapine-analogs of Formulae I-IVe to modulate sleep. Preferably, compounds of Formulae I-IVe modulate sleep with decreased side effects: e.g., the compounds do not inhibit REM sleep (consequently, sleep induced by these compounds may more closely resemble a person's natural sleep cycles), use of the compounds does not result in rebound insomnia, and/or the compounds do not inhibit locomotor activity or adversely effect body temperature.

The in vitro selection criteria for loxapine analogs of the invention are shown in Table 2.

TABLE 2

| H1 Binding (Primary Target) | Ki < 500 nMolar |
|---|---|
| Off Target Binding | |
| Cholinergic M1, M2, M3 | Ki > 10 times the measured H1 receptor Ki |
| Dopamine D1, D2 | Ki > 10 times the measured H1 receptor Ki |
| Adrenergic α1, α2 | Ki > 10 times the measured H1 receptor Ki |

In one embodiment, the off target binding Ki is 50 times the measured H1 receptor Ki. In some embodiments, the off target binding Ki is 100 times the measured H1 receptor Ki.

In vitro binding assays are used to determine H1 binding (i.e., primary target binding) and M1, M2 and M3 binding (i.e., off target binding). These binding assays measure the ability of loxapine analogs to displace known standards from the H1, M1, M2, and M3 receptors, wherein H1 is a histamine receptor, and M1, M2, and M3 are cholinergic (muscarinic) receptors. Similar assays are performed with H1 and dopamine receptors (D1, and D2), and with H1 and adrenergic receptors (α1 and α2).

The binding studies against the histamine receptor, H1, indicate binding affinity, and therefore, the results of the binding assays are an indication of the activity of the loxapine analog compound. The binding studies against the muscarinic receptors indicate the extent to which the compounds bind the muscarinic receptors responsible for anti-cholinergic activity of the compound. Binding to muscarinic receptors results in several undesired side effects of many known antihistamines, e.g., dry-mouth. A decrease in the binding of the compounds to the M1-M3 receptors, relative to the binding of the compound to the H1 receptor, is an indication of the greater specificity of the compound for the histamine receptor over the muscarinic receptor. Moreover, a drug with increased specificity for the histamine receptor possesses less anti-cholinergic side effects.

The H1 binding of loxapine analogs of the invention (also referred to herein as "test compounds" or "compounds of the invention") is determined by measuring the specific binding of a given test compound, or series of test compounds, to the H1 receptor, and comparing it with the specific binding of known standard (i.e., reference compound). Reference compounds used in this H1 binding assay include, for example, triprolidine ($K_i$ 3.3 nM), chlorpheniramine ($K_i$ 103.0 nM), pyrilamine ($K_i$ 1.9 nM), cyproheptadine ($K_i$ 8.5 nM), cimetidine ($K_i$>10,000) and dimaprit ($K_i$>10,000). (See e.g., Chang et al., J. Neurochem., 32:1653-63 (1979) (with modifications); Martinez-Mir, et al., Brain Res., 526:322-27 (1990); and Haaksme, et al., Pharmac. Ther., 47:73-104 (1990).

For example, in one embodiment of the H1 binding assay, the H1 receptor is from bovine cellular membranes, and a radioligand, [$^3$H]Pyrilamine (15-25 Ci/mmol) at a final ligand concentration of 2.0 nM is used to detect specific binding for the H1 receptor. The assay characteristics include a $K_D$ (binding affinity) of 1.3 nM and a $B_{max}$ (receptor number) of 6.2 fmol/mg tissue (wet weight). Tripolidine (10 μM) is used as the non-specific determinant, reference compound and positive control. Binding reactions are carried out in 50 mM NA-KPO$_4$ (pH 7.5) at 25° C. for 60 minutes. The reaction is terminated by rapid vacuum filtration onto glass fiber filters. The level of radioactivity trapped on the filters is measured and compared to control values to ascertain any interaction between a given test compound and the H1 binding site.

The M1 binding assay determines the M1 binding of a test compound by measuring the specific binding of a given test compound to M1 and comparing it with the specific binding of a reference compound. (See e.g., Buckley, et al., Mol. Pharmacol. 35:469-76 (1989) (with modifications)). Reference compounds used in the M1 binding assay include, for example, scopolamine, MethylBr ($K_i$ 0.09 nM); 4-DAMP methiodide ($K_i$ 0.27 nM); pirenzepine ($K_i$ 2.60 nM); HHSID ($K_i$ 5.00 nM); and methoctramine ($K_i$ 29.70 nM).

For example, in one embodiment of the M1 binding assay, the M1 muscarinic receptor is a human recombinant M1 expressed in CHO cells, and a radioligand, [$^3$H]-scopolamine, N-methyl chloride (80-100 Ci/mmol) at a final ligand concentration of 0.5 nM is used to detect specific binding for M1. The assay characteristics include a $K_D$ (binding affinity) of 0.05 nM and a $B_{max}$ (receptor number) of 4.2 pmol/mg protein. (−)-scopolamine, methyl-, bromide (methylscopolamine bromide) (1.0 µM) is used as the non-specific determinant, reference compound and positive control. Binding reactions are carried out in PBS for 60 minutes at 25° C. The reaction is terminated by rapid vacuum filtration onto glass fiber filters. The level of radioactivity trapped on the filters is measured and compared to control values to ascertain any interaction between a given test compound and the cloned muscarinic M1 binding site.

The M2 binding assay determines the M2 binding of a test compound by measuring the specific binding of a given test compound to M2 and comparing it with the specific binding of a reference compound. (See e.g., Buckley, et al., Mol. Pharmacol. 35:469-76 (1989) (with modifications)). Reference compounds used in the M2 binding assay include, for example, scopolamine, MethylBr ($K_i$ 0.3 nM); 4-DAMP methiodide ($K_i$ 20.7 nM); methoctramine ($K_i$ 20.460 nM); HHSID ($K_i$ 212.7 nM); and pirenzepine ($K_i$ 832.9 nM).

For example, in one embodiment of the M2 binding assay, the M2 muscarinic receptor is a human recombinant M2 expressed in CHO cells, and a radioligand, [$^3$H]-scopolamine, N-methyl chloride (80-100 Ci/mmol) at a final ligand concentration of 0.5 nM is used to detect specific binding for M1. The assay characteristics include a $K_D$ (binding affinity) of 0.29 nM and a $B_{max}$ (receptor number) of 2.1 pmol/mg protein. (−)-scopolamine, methyl-, bromide (methylscopolamine bromide) (1.0 µM) is used as the non-specific determinant, reference compound and positive control. Binding reactions are carried out in PBS for 60 minutes at 25° C. The reaction is terminated by rapid vacuum filtration onto glass fiber filters. The level of radioactivity trapped on the filters is measured and compared to control values to ascertain any interaction between a given test compound and the cloned muscarinic M2 binding site.

The M3 binding assay determines the M3 binding of a test compound by measuring the specific binding of a given test compound to M3 and comparing it with the specific binding of a reference compound. (See e.g., Buckley, et al., Mol. Pharmacol. 35:469-76 (1989) (with modifications)). Reference compounds used in the M3 binding assay include, for example, scopolamine, MethylBr ($K_i$ 0.3 nM); 4-DAMP methiodide ($K_i$ 0.8 nM); HHSID ($K_i$ 14.5 nM); pirenzepine ($K_i$ 153.3 nM); and methoctramine ($K_i$ 700.0 nM).

For example, in one embodiment of the M3 binding assay, the M3 muscarinic receptor is a human recombinant M3 expressed in CHO cells, and a radioligand, [$^3$H]-scopolamine, N-methyl chloride (80-100 Ci/mmol) at a final ligand concentration of 0.2 nM is used to detect specific binding for M1. The assay characteristics include a $K_D$ (binding affinity) of 0.14 nM and a $B_{max}$ (receptor number) of 4.0 pmol/mg protein. (−)-scopolamine, methyl-, bromide (methylscopolamine bromide) (1.0 µM) is used as the non-specific determinant, reference compound and positive control. Binding reactions are carried out in 50 mM TRIS-HCl (pH 7.4) containing 10 mM $MgCl_2$, 1 mM EDTA for 60 minutes at 25° C. The reaction is terminated by rapid vacuum filtration onto glass fiber filters. The level of radioactivity trapped on the filters is measured and compared to control values to ascertain any interaction between a given test compound and the cloned muscarinic M3 binding site.

In vitro selection criteria for loxapine analogs of the invention are shown in Table 3.

TABLE 3

| H1 Binding (Primary Target) Off Target Binding | Ki < 300 nMolar |
|---|---|
| Cholinergic M1 | Ki > 1 uM |
| Cholinergic M2 | Ki > 1 uM |
| Cholinergic M3 | Ki > 1 uM |

Other in vitro selection criteria for loxapine analogs of the invention are shown in Table 4.

TABLE 4

| H1 Binding (Primary Target) Off Target Binding | Ki < 150 nMolar |
|---|---|
| Cholinergic M1 | Ki > 10 uM |
| Cholinergic M2 | Ki > 10 uM |
| Cholinergic M3 | Ki > 10 uM |

H1 binding (primary target binding) and M1, M2 and M3 binding (off target binding) are determined using the H1, M1, M2 and M3 binding assays described above.

Other in vitro selection criteria for loxapine analogs of the invention includes hERG binding. Primary target binding and off target binding are determined as described above. If the test compound exhibits the desired primary target (H1) binding and primary target/off target binding ration, hERG binding (off target binding) is determined using a hERG block comparative study to evaluate the effect of a given test compound on cloned hERG channels expressed in mammalian cells. (See e.g., Brown and Rampe, Pharmaceutical News 7:15-20 (2000); Rampe et al., FEBS Lett., 417:28-32 (1997); Weirich and Antoni, Basic Res. Cardiol. 93 Suppl. 1:125-32 (1998); and Yap and Camm, Clin. Exp. Allergy, 29 Suppl 3, 174-81 (1999)).

Off target binding of hERG, the cardiac potassium channel responsible for the rapid delayed rectifier current ($I_{Kr}$) in human ventricles, is evaluated because inhibition of $I_{Kr}$ is the most common cause of cardiac action potential prolongation by non-cardiac drugs. (See Brown and Rampe (2000), Weirich and Antoni (1998); and Yap and Camm (1999)). Increased action potential duration causes prolongation of the QT interval that has been associated with a dangerous ventricular arrhythmia, torsade de pointes. (Brown and Rampe (2000)).

In the hERG assay, hERG channels are expressed in a human embryonic kidney cell line (HEK293) that lacks endogenous $I_{Kr}$. Expression in a mammalian cell line is preferable to transient expression in *Xenopus oocytes*, as the latter demonstrates a consistent 10-100 fold lower sensitivity to hERG channel blockers. (See, Rampe 1997).

In one embodiment of the hERG assay, the positive control (i.e., reference compound) is terfenadine (Sigma, St. Louis Mo.), which has been shown, at a concentration of 60 nM, to block hERG current by approximately 75%. Test compounds are delivered in HEPES-buffered physiological saline (HB-PS)+0.1% dimethyl sulfoxide (DMSO). Each test compound is applied at a concentration of 10 µM to the HEK293 cells expressing hERG (n≧3, where n=the number of cells). Cells are exposed to the test compound for the time necessary to reach steady-state block, but not longer than 10 minutes. The positive control (60 mM terfenadine) is applied to two cells (n≧2).

The hERG-exposed cells are then transferred to the recording chamber and superfused with HB-PS solution. The pipette solution for whole cell recordings includes potassium aspartate (130 mM), $MgCl_2$ (5 mM), EGTA (5 mM), ATP (4 mM), and HEPES (10 mM) at a pH adjusted to 7.2 with KOH.

Onset and steady state block of hERG current due to the test compound are measured using a pulse pattern with fixed amplitudes (depolarization: +20 mV for 2 seconds; repolarization: −50 mV for 2 seconds), repeated at 10 second intervals, from a holding potential of −80 mV. Peak tail current is measured during the 2 second step to −50 mV. A steady state is maintained for at least 30 seconds before applying the test compound or positive control compound. Peak tail currents are measured until a new steady state is achieved.

In addition to the in vitro selection criteria described above, loxapine analogs of the invention are selected using the following in vivo sleep-wake and physiological assessments:

NonREM Sleep: Loxapine analogs are selected if, in adult, male Wistar rats, (i) peak nonREM amount exceeds 55% nonREM per hour by no later than the third hour post-treatment; and (ii) the nature of this increase in nonREM sleep is such that the net cumulative total increase in nonREM sleep in the initial 6 hours post-treatment (adjusted for baseline at the corresponding circadian time 24 hours earlier, and relative to Vehicle control treatment) is not less than 20 minutes in total for compound doses that produces maximum sleep consolidation as measured by sleep bout length, when drug is delivered orally.

The term "nonREM peak sleep time" is defined as an absolute peak amount of nonREM sleep per hour post treatment, with drug administration occurring at Circadian Time (CT) 18, which is 6 hours after lights off in a nocturnal laboratory rat when housed in a LD 12:12 (12-hours light and 12 hours dark) light-dark cycle. The nominal criteria of 55% nonREM sleep per hour is equivalent to 33 minutes of non-REM sleep per hour.

As used herein, the term "cumulative nonREM sleep" is defined as the net total aggregate increase in the number of minutes of nonREM sleep, measured through out the entire duration of a drug's soporific effect, which typically, but not always occurs in the first 6 hours post-treatment, adjusted for the net total aggregate number of minutes of nonREM sleep that occurred during the corresponding non-treatment baseline times of day recorded 24 hours earlier, relative to like vehicle control treatment.

As defined herein, the term "sleep bout" refers to a discrete episode of continuous or near continuous sleep, comprised of nonREM sleep, REM sleep, or both nonREM and REM sleep stages, delimited prior and after the episode by greater than two contiguous 10 second epochs of wakefulness. The following non-limiting description illustrates this concept: WWWW<u>SSSSWSSSSSSSWWSSSSSSS</u>WWW, wherein each letter represents the predominant state of arousal (S=sleep, W=wake) observed each 10 seconds. The measured sleep "bout" is 21 ten-second epochs or 3.5 minutes in duration.

Sleep Consolidation: Loxapine analogs are selected if, in adult male Wistar rats, (i) the absolute duration of longest continuous sleep episodes (i.e., "sleep bout") post-treatment is greater than 13 minutes in duration; (ii) the net longest sleep bout post treatment is greater than or equal to 3 minutes when adjusted for baseline 24 hours earlier and calculated relative to vehicle treatment; and (iii) the mean absolute duration of every sleep bout when averaged per hour, on an hour by hour basis, is greater than or equal to 5 minutes. The aforementioned selection criteria assume that stages of sleep and wakefulness are determined continuously every 10 seconds (e.g., 10 second sleep scoring "epochs"), that sleep and wakefulness are measured polygraphically using EEG and EMG criteria, and sleep episodes (comprised of nonREM and/or REM sleep) are defined as continuous "bouts" until the episode is interrupted by greater than two contiguous 10 second epochs of wakefulness.

As used herein, the term "longest sleep bout length" is defined as the total number of minutes an animal remains asleep (nonREM and/or REM sleep stages) during the single longest sleep bout that occurred beginning in a given hour post-treatment. The "sleep bout length" measurement criteria assumes sleep is measured continuously in 10 second epochs, and is scored based upon the predominant state, computed or otherwise determined as a discrete sleep stage (where sleep stages are defined as nonREM sleep, REM sleep, or wakefulness) during the 10 second interval that defines the epoch.

The term "average sleep bout length" is defined as the average duration (in minutes) of every and all sleep episodes or bouts that began in a given hour, independent of the individual duration of each episode or bout.

Concurrently Measured Side Effects: Loxapine analogs are selected if, in adult, male Wistar rats, these compounds (i) do not produce appreciable amounts of rebound insomnia; (ii) do not appreciably inhibit REM sleep; and (iii) do not disproportionately inhibit locomotor motor activity and/or motor tone relative to the normal effects of sleep itself. The threshold definitions for these three side-effect variables are as follows:

"Rebound insomnia" is defined as period of rebound, paradoxical, or compensatory wakefulness that occurs after the sleep promoting effects of a hypnotic or soporific agent. Rebound insomnia is typically observed during the usual circadian rest phase 6-18 hours post-treatment at CT-18 (6 hours after lights-off, given LD 12:12), but can occur at any time during the initial 30 hours post-treatment. Rebound is considered unacceptable when, in the adult, male Wistar rat, excess cumulative wakefulness associated with rebound insomnia is greater than 10% reduction in average of hourly NonREM sleep times during post-treatment circadian rest phase (lights-on).

In adult, male Wistar rats, rebound insomnia manifests as an increase in wakefulness relative to corresponding times at baseline (24 hours earlier) subsequent to a drug-induced sleep effect, and rebound insomnia is measured cumulatively.

"REM sleep inhibition" is defined as the reduction of REM sleep time post-treatment at CT-18 (6 hours after lights-off; LD 12:12) or at CT-5 (5 hours after lights-on; LD 12:12). Compounds that reduce REM sleep time by greater than 15 minutes (relative to baseline and adjusted for vehicle treatment) when administered at either CT-18 or CT-5 are considered unacceptable.

As defined herein, "disproportionate locomotor activity inhibition" is a reduction of locomotor activity that exceeds the normal and expected reduction in behavioral activity attributable to sleep. Logic dictates that if an animal is asleep, there will normally be a corresponding reduction in locomotor activity. If a hypnotic or soporific compound reduces locomotor activity levels in excess of 20% greater than that explained by sleep alone, the compound is deemed unacceptable. Locomotor activity (LMA) or motor tone may be quantified objectively using any form of behavioral locomotor activity monitor (non-specific movements, telemetry-based activity monitoring, 3-dimensional movement detection devices, wheel running activity, exploratory measures, electromyographic recording, etc.) so long as it is measured concurrently with objective sleep-wakefulness measures in the same animal.

In one embodiment, locomotor activity within the animal's cage is measured using a biotelemetry device surgically implanted in the animal's peritoneal cavity; the implantable device and associated telemetry receiver detects if and how much animal moves within the cage. Sleep and wakefulness is measured in 10 second epochs simultaneously. Counts of locomotor activity per unit time are divided by the concurrent amount of wakefulness per the same unit, yielding a "locomotor activity intensity" (LMAI) measure for that unit time. Hypnotic or soporific compounds administered at CT-18 (6 hours after lights-off; LD 12:12) that decrease locomotor activity per unit time awake by greater than 20% relative to vehicle would be judged unacceptable.

In another embodiment, the loxapine analogs of the invention are selected using the in vivo sleep-wake and physiological assessment criteria shown in Table 5:

TABLE 5

| SCORE-2000 | Absolute Value | Change from baseline value relative to vehicle only |
|---|---|---|
| NonREM Peak Time | >55% sleep/hour peak | Not applicable |
| Cumulative NonREM | Not applicable | >20 minutes at ED100 for MSBL at $T_{1-6}$ |
| Longest Sleep Bout | >17 minutes absolute peak | >5 minutes |
| Average Sleep Bout | >6 minutes absolute peak | Not used in SAR cuts |
| Rebound Insomnia | <10% reduction in average of hourly NonREM sleep times during post-treatment circadian rest phase (lights-on) | Not applicable |
| REM Sleep Inhibition | not applicable | not to exceed 15 minutes, Rx at CT5 |
| LMAI | not applicable | not to exceed 20% LMAI reduction |

Methods for evaluating these sleep-wake and physiological assessment criteria are described above. The "absolute value" shown in second column of Table 5 refers to the value as determined for each test compound, while the "change" value shown in the third column of Table 5 reflects an adjusted value in which the absolute value is the difference from vehicle, when the vehicle values are adjusted for baseline.

In some embodiments, the longest sleep bout is greater than 13 minutes in duration. In others, it is greater than 17 minutes in duration. In some embodiments, the net longest sleep bout post treatment is greater than or equal to 3 minutes in duration. In others, it is greater than or equal to 6 minutes in duration.

Other in vivo sleep-wake and physiological assessment criteria used to select loxapine analogs of the invention include measurement of acute body temperature and latent body temperature as a change in baseline relative to vehicle. The acute body temperature change should not exceed −0.50° C., and the latent body temperature change should not exceed +0.50° C. at Time 1-6 hours. The acute body temperature ($T_{1-6}$) is adjusted for the corresponding baseline measured 24 hours earlier, relative to vehicle (the decrease from vehicle). The latent body temperature, measured 7-18 hours post drug treatment ($T_{7-18}$), is adjusted for the corresponding baseline measured 24 hours earlier, relative to vehicle (the decrease from vehicle).

The invention provides a method of modulating sleep by administering to a subject a therapeutically effective amount of a compound of Formula I-IVe or a pharmaceutically effective salt thereof. The compounds modulate sleep in several ways, including decreasing the time to sleep onset, increasing the average sleep bout length, and increasing the maximum sleep bout length.

The compounds, or pharmaceutically acceptable salts thereof, is administered orally, nasally, transdermally, pulmonary, inhalationally, buccally, sublingually, intraperintoneally, intravenously, rectally, intrapleurally, intrathecally and parenterally. In one embodiment, the compound is administered orally. One skilled in the art will recognize the advantages of certain routes of administration.

The method of modulating sleep by administering to a subject a therapeutically effective amount of a compound of Formula I-IVe or a pharmaceutically effective salt thereof is used to treat a variety of sleep disorders including circadian rhythm abnormality, insomnia, parasomnia, sleep apnea syndrome, narcolepsy and/or hypersomnia. In one embodiment, the method treats circadian rhythm abnormalities such as jet lag, shift-work disorders, delayed sleep phase syndrome, advanced sleep phase syndrome and non-24 hour sleep-wake disorder. In another embodiment, the method treats insomnia including extrinsic insomnia, psychophysiologic insomnia, altitude insomnia, restless leg syndrome, periodic limb movement disorder, medication-dependent insomnia, drug-dependent insomnia, alcohol-dependent insomnia and insomnia associated with mental disorders.

In another embodiment, the method treats parasomnias including somnambulism, pavor nocturnus, REM sleep behavior disorder, sleep bruxism and sleep enuresis. In yet another embodiment, the method treats sleep apnea disorder including central sleep apnea, obstructive sleep apnea and mixed sleep apnea. Additionally, the method treats other sleep disorders such as narcolepsy or hypersomnia.

In some embodiments, a compound of Formula I-IVe is administered as a pharmaceutically acceptable salt. One skilled in the art will recognize the various methods for creating pharmaceutically acceptable salts and identifying the appropriate salt. In a one embodiment, the compound or a pharmaceutically acceptable salt thereof is included in a pharmaceutical composition.

As used herein, the term "sleep disorder" includes conditions recognized by one skilled in the art as sleep disorders, for example, conditions known in the art or conditions that are proposed to be sleep disorders or discovered to be sleep disorders. See, for example, Thorpy, M J *International Classification of Sleep Disorders, Revised: Diagnostic and Coding Manual*. American Sleep Disorders Association; Rochester, Minnesota 1997; and *ICD-9-CM, International Classification of Diseases, Ninth Revision, Clinical Modification*, National Center for Health Statistics, Hyattsville, Md.

For example, sleep disorders can be generally classed into dyssomnias, e.g., intrinsic, extrinsic, and circadian rhythm disorders; parasomnias, e.g., arousal, sleep-wake transition, and rapid eye movement (REM) associated disorders, and other parasomnias; disorders associated with mental, neurological, and other medical disorders; and other sleep disorders.

Intrinsic sleep disorders include, for example, psychophysiological insomnia, sleep state misperception, idiopathic insomnia, narcolepsy, recurrent hypersomnia, idiopathic hypersomnia, post-traumatic hypersomnia, obstructive sleep apnea syndrome, central sleep apnea syndrome, central alveolar hypoventilation syndrome, periodic limb movement disorder, and restless legs syndrome.

Extrinsic sleep disorders include, for example, inadequate sleep hygiene, environmental sleep disorder, altitude insomnia, adjustment sleep disorder, insufficient sleep syndrome, limit-setting sleep disorder, sleep-onset association disorder, food allergy insomnia, nocturnal eating (drinking) syndrome, hypnotic-dependent sleep disorder, stimulant-dependent sleep disorder, alcohol-dependent sleep disorder, and toxin-induced sleep disorder.

Circadian rhythm sleep disorders include, for example, time-zone change (et lag) syndrome, shift work sleep disorder, irregular sleep-wake pattern, delayed sleep phase syndrome, advanced sleep phase syndrome, and non-24-hour sleep-wake disorder.

Arousal sleep disorders include, for example, confusional arousals, sleepwalking and sleep terrors.

Sleep-wake transition disorders include, for example, rhythmic movement disorder, sleep starts, sleeptalking, and nocturnal leg cramps.

REM-associated sleep disorders include, for example, nightmares, sleep paralysis, impaired sleep-related penile erections, sleep-related painful erections, REM sleep-related sinus arrest, and REM sleep behavior disorder.

Other parasomnias include, for example, sleep bruxism, sleep enuresis, sleep-related abnormal swallowing syndrome, nocturnal paroxysmal dystonia, sudden unexplained nocturnal death syndrome, primary snoring, infant sleep apnea, congenital central hypoventilation syndrome, sudden infant death syndrome, and benign neonatal sleep myoclonus.

A "sleep disorder" also arises in a subject that has other medical disorders, diseases, or injuries, or in a subject being treated with other medications or medical treatments, where the subject as a result has difficulty falling asleep and/or remaining asleep, or experiences unrefreshing sleep or non-restorative sleep, e.g., the subject experiences sleep deprivation. For example, some subjects have difficulty sleeping after undergoing medical treatment for other conditions, e.g., chemotherapy or surgery, or as a result of pain or other effects of physical injuries.

It is well known in the art that certain medical disorders, for example, central nervous system (CNS) disorders, e.g., mental or neurological disorders, e.g., anxiety, can have a sleep disorder component, e.g., sleep deprivation. Thus, "treating a sleep disorder" also includes treating a sleep disorder component of other disorders, e.g., CNS disorders. Further, treating the sleep disorder component of CNS disorders can also have the beneficial effect of ameliorating other symptoms associated with the disorder. For example, in some subjects experiencing anxiety coupled with sleep deprivation, treating the sleep deprivation component also treats the anxiety component. Thus, the present invention also includes a method of treating such medical disorders.

For example, sleep disorders associated with mental disorders include psychoses, mood disorders, anxiety disorders, panic disorder, addictions, and the like. Specific mental disorders include, for example, depression, obsessive compulsive disorder, affective neurosis/disorder, depressive neurosis/disorder, anxiety neurosis; dysthymic disorder, behavior disorder, mood disorder, schizophrenia, manic depression, delirium, and alcoholism.

Sleep disorders associated with neurological disorders include, for example, cerebral degenerative disorders, dementia, parkinsonism, Huntington's disease, Alzheimer's, fatal familial insomnia, sleep related epilepsy, electrical status epilepticus of sleep, and sleep-related headaches. Sleep disorders associated with other medical disorders include, for example, sleeping sickness, nocturnal cardiac ischemia, chronic obstructive pulmonary disease, sleep-related asthma, sleep-related gastroesophageal reflux, peptic ulcer disease, and fibrositis syndrome.

In some circumstances, sleep disorders are also associated with pain, e.g., neuropathic pain associated with restless leg syndrome; migraine; hyperalgesia, fibromyalgia, pain; enhanced or exaggerated sensitivity to pain, such as hyperalgesia, causalgia and allodynia; acute pain; burn pain; atypical facial pain; neuropathic pain; back pain; complex regional pain syndromes I and II; arthritic pain; sports injury pain; pain related to infection, e.g., HIV, post-polio syndrome, and post-herpetic neuralgia; phantom limb pain; labor pain; cancer pain; post-chemotherapy pain; post-stroke pain; post-operative pain; neuralgia; conditions associated with visceral pain including irritable bowel syndrome, migraine and angina.

Other sleep disorders include, for example, short sleeper, long sleeper, subwakefulness syndrome, fragmentary myoclonus, sleep hyperhidrosis, menstrual-associated sleep disorder, pregnancy-associated sleep disorder, terrifying hypnagogic hallucinations, sleep-related neurogenic tachypnea, sleep-related laryngospasm, and sleep choking syndrome.

Insomnia is typically classed into sleep onset insomnia, where a subject takes more than 30 minutes to fall asleep; and sleep maintenance insomnia, where the subject spends more than 30 minutes awake during an expected sleep period, or, for example, waking before the desired wake-up time with difficulty or an inability to get back to sleep. The disclosed compounds may be effective in treating sleep onset and sleep maintenance insomnias, insomnia resulting from circadian rhythm adjustment disorders, or insomnia resulting from CNS disorders. A one embodiment is treating a subject for a circadian rhythm adjustment disorder. Another embodiment is treating a subject for insomnia resulting from a mood disorder. In other embodiments, a subject is treated for sleep apnea, somnambulism, night terrors, restless leg syndrome, sleep onset insomnia, and/or sleep maintenance insomnia; or more preferably, sleep onset insomnia or sleep maintenance insomnia. The disclosed compounds may be effective for treating sleep onset insomnia. The disclosed compounds may also be effective for treating sleep maintenance insomnia.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Oral dosages of the present invention, when used for the indicated effects, will range between about 0.05 to 5000 mg/day orally. Effective amounts of the disclosed compounds typically range between about 0.01 mg/kg per day and about 100 mg/kg per day, and preferably between 0.1 mg/kg per day and about 10 mg/kg/day. Techniques for administration of the disclosed compounds of the invention can be found in *Remington: the Science and Practice of Pharmacy*, 19$^{th}$ edition, Mack Publishing Co., Easton, Pa. (1995).

For example, in some embodiments, an acid salt of a compound containing an amine or other basic group is obtained by reacting the compound with a suitable organic or inorganic acid, such as hydrogen chloride, hydrogen bromide, acetic acid, perchloric acid and the like. Compounds with a quaternary ammonium group also contain a counter anion such as chloride, bromide, iodide, acetate, perchlorate and the like. Other examples of such salts include hydrochlorides, hydrobromides, sulfates, methanesulfonates, nitrates, maleates, acetates, citrates, fumarates, tartrates (e.g., (+)-tartrates, (−)-tartrates or mixtures thereof including racemic mixtures), succinates, benzoates and salts with amino acids such as glutamic acid.

Salts of compounds containing a carboxylic acid or other acidic functional group are prepared by reacting with a suitable base. Such a pharmaceutically acceptable salt is made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, N-benzyl-β-phenethylamine, dehydroabietylamine, N,N'-bisdehydroabietylamine, glucamine, N-methylglucamine, collidine, quinine, quinoline, and basic amino acid such as lysine and arginine.

In some embodiments, certain compounds and their salts also exist in the form of solvates, for example hydrates, and the present invention includes each solvate and mixtures thereof.

In an embodiment, the compounds described herein, and the pharmaceutically acceptable salts thereof are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein. Techniques for formulation and administration of the disclosed compounds of the invention can be found in *Remington: the Science and Practice of Pharmacy*, above.

Typically, the compound is prepared for oral administration, wherein the disclosed compounds or salts thereof are combined with a suitable solid or liquid carrier or diluent to form capsules, tablets, pills, powders, syrups, solutions, suspensions and the like.

The tablets, pills, capsules, and the like contain from about 1 to about 99 weight percent of the active ingredient and a binder such as gum tragacanth, acacias, corn starch or gelatin; excipients such as dicalcium phosphate; a disintegrating agent such as corn starch, potato starch or alginic acid; a lubricant such as magnesium stearate; and/or a sweetening agent such as sucrose, lactose, saccharin, xylitol, and the like. When a dosage unit form is a capsule, it often contains, in addition to materials of the above type, a liquid carrier such as a fatty oil.

In some embodiments, various other materials are present as coatings or to modify the physical form of the dosage unit. For instance, in some embodiments, tablets are coated with shellac, sugar or both. In some embodiments, a syrup or elixir contains, in addition to the active ingredient, sucrose as a sweetening agent, methyl and propylparabens as preservatives, a dye and a flavoring such as cherry or orange flavor, and the like.

For some embodiments relating to parental administration, the disclosed compounds, or salts, solvates, or polymorphs thereof, can be combined with sterile aqueous or organic media to form injectable solutions or suspensions. Injectable compositions are preferably aqueous isotonic solutions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1 to 75%, preferably about 1 to 50%, of the active ingredient.

For example, injectable solutions are produced using solvents such as sesame or peanut oil or aqueous propylene glycol, as well as aqueous solutions of water-soluble pharmaceutically-acceptable salts of the compounds. In some embodiments, dispersions are prepared in glycerol, liquid polyethylene glycols and mixtures thereof in oils. Under ordinary conditions of storage and use, these preparations contain a preservative to prevent the growth of microorganisms. The terms "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

For rectal administration, suitable pharmaceutical compositions are, for example, topical preparations, suppositories or enemas. Suppositories are advantageously prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1 to 75%, preferably about 1 to 50%, of the active ingredient.

In some embodiments, the compounds are formulated to deliver the active agent by pulmonary administration, e.g., administration of an aerosol formulation containing the active agent from, for example, a manual pump spray, nebulizer or pressurized metered-dose inhaler. In some embodiments, suitable formulations of this type also include other agents, such as antistatic agents, to maintain the disclosed compounds as effective aerosols.

A drug delivery device for delivering aerosols comprises a suitable aerosol canister with a metering valve containing a pharmaceutical aerosol formulation as described and an actuator housing adapted to hold the canister and allow for drug delivery. The canister in the drug delivery device has a headspace representing greater than about 15% of the total volume of the canister. Often, the polymer intended for pulmonary administration is dissolved, suspended or emulsified in a mixture of a solvent, surfactant and propellant. The mixture is maintained under pressure in a canister that has been sealed with a metering valve.

For nasal administration, either a solid or a liquid carrier can be used. The solid carrier includes a coarse powder having particle size in the range of, for example, from about 20 to about 500 microns and such formulation is administered by rapid inhalation through the nasal passages. In some embodiments where the liquid carrier is used, the formulation is administered as a nasal spray or drops and includes oil or aqueous solutions of the active ingredients.

Also contemplated are formulations that are rapidly dispersing dosage forms, also known as "flash dose" forms. In particular, some embodiments of the present invention are formulated as compositions that release their active ingredients within a short period of time, e.g., typically less than about five minutes, preferably less than about ninety seconds, more preferably in less than about thirty seconds and most preferably in less than about ten or fifteen seconds. Such formulations are suitable for administration to a subject via a variety of routes, for example by insertion into a body cavity or application to a moist body surface or open wound.

Typically, a "flash dosage" is a solid dosage form that is administered orally, which rapidly disperses in the mouth, and hence does not require great effort in swallowing and allows the compound to be rapidly ingested or absorbed through the oral mucosal membranes. In some embodiments, suitable rapidly dispersing dosage forms are also used in other applications, including the treatment of wounds and other bodily insults and diseased states in which release of the medicament by externally supplied moisture is not possible.

"Flash dose" forms are known in the art; see for example, effervescent dosage forms and quick release coatings of insoluble microparticles in U.S. Pat. Nos. 5,578,322 and 5,607,697; freeze dried foams and liquids in U.S. Pat. Nos. 4,642,903 and 5,631,023; melt spinning of dosage forms in U.S. Pat. Nos. 4,855,326, 5,380,473 and 5,518,730; solid, free-form fabrication in U.S. Pat. No. 6,471,992; saccharide-based carrier matrix and a liquid binder in U.S. Pat. Nos. 5,587,172, 5,616,344, 6,277,406, and 5,622,719; and other forms known to the art.

The loxapine analogs of the invention are also formulated as "pulsed release" formulations, in which the analog is released from the pharmaceutical compositions in a series of releases (i.e., pulses). The loxapine analogs are also formulated as "sustained release" formulations in which the analog is continuously released from the pharmaceutical composition over a prolonged period.

Also contemplated are formulations, e.g., liquid formulations, including cyclic or acyclic encapsulating or solvating agents, e.g., cyclodextrins, polyethers, or polysaccharides (e.g., methylcellulose), or more preferably, polyanionic β-cyclodextrin derivatives with a sodium sulfonate salt group separate from the lipophilic cavity by an alkyl ether spacer group or polysaccharides. In one embodiment, the agent is methylcellulose. In another embodiment, the agent is a polyanionic β-cyclodextrin derivative with a sodium sulfonate salt separated from the lipophilic cavity by a butyl ether spacer group, e.g., CAPTISOL® (CyDex, Overland, Kan.). One skilled in the art can evaluate suitable agent/disclosed compound formulation ratios by preparing a solution of the agent in water, e.g., a 40% by weight solution; preparing serial dilutions, e.g., to make solutions of 20%, 10, 5%, 2.5%, 0% (control), and the like; adding an excess (compared to the amount that can be solubilized by the agent) of the disclosed compound; mixing under appropriate conditions, e.g., heating, agitation, sonication, and the like; centrifuging or filtering the resulting mixtures to obtain clear solutions; and analyzing the solutions for concentration of the disclosed compound.

In addition to the therapeutic formulations described above, a therapy including the compounds of the present invention optionally includes, co-administration with one or more additional therapies, e.g., drugs or physical or behavioral treatments (e.g., light therapy, electrical stimulation, behavior modification, cognitive therapy, circadian rhythm modification, and the like). Such a practice is referred to as "combination therapy." The other therapy or therapies in the combination therapy include therapies recognized by one skilled in the art as desirable in combination with the compound of the invention, for example, therapies known to the art or therapies which are proposed or discovered in the art for treating sleep disorders or treating diseases associated with sleep disorders, for example, therapies for any of the sleep disorders or other conditions disclosed herein. In some embodiments the compound is administered as a combination therapy whereas it is administered as a monotherapy in other embodiments.

Typically, the compound is administered as a monotherapy.

One skilled in the art will appreciate that a therapy administered in combination with the compounds of the present invention is directed to the same or a different disorder target as that being targeted by the compounds of the present invention. Administration of the compound of the invention is first, followed by the other therapy; or alternatively, administration of the other therapy may be first. The other therapy is any known in the art to treat, prevent, or reduce the symptoms of the targeted disorder, e.g., a sleep disorder, or other disorders, e.g., other CNS disorders. In addition, some embodiments of the present invention have compounds administered in combination with other known therapies for the target disorder. Furthermore, the other therapy includes any agent of benefit to the patient when administered in combination with the disclosed compound.

For example, in some embodiments where the other therapy is a drug, it is administered as a separate formulation or in the same formulation as the compound of the invention. A compound of the invention is administered in combination therapy with any one or more of commercially-available, over-the-counter or prescription medications, including, but not limited to antihistamines, antimicrobial agents, fungistatic agents, germicidal agents, hormones, antipyretic agents, antidiabetic agents, bronchodilators, antidiarrheal agents, antiarrhythmic agents, coronary dilation agents, glycosides, spasmolytics, antihypertensive agents, antidepressants, antianxiety agents, other psychotherapeutic agents, steroids, corticosteroids, analgesics, cold medications, vitamins, sedatives, hypnotics, contraceptives, nonsteroidal anti-inflammatory drugs, blood glucose lowering agents, cholesterol lowering agents, anticonvulsant agents, other antiepileptic agents, immunomodulators, anticholinergics, sympatholytics, sympathomimetics, vasodilatory agents, anticoagulants, antiarrhythmics, prostaglandins having various pharmacologic activities, diuretics, sleep aids, antihistaminic agents, antineoplastic agents, oncolytic agents, antiandrogens, antimalarial agents, antileprosy agents, and various other types of drugs. See Goodman and Gilman's The Basis of Therapeutics (Eighth Edition, Pergamon Press, Inc., USA, 1990) and The Merck Index (Eleventh Edition, Merck & Co., Inc., USA, 1989).

Examples of drugs used in combination with the compounds of the invention include, but are not limited to, AMBIEN® STILNOX® (zolpidem tartrate), indiplon, ESTORRA™ (eszopiclone), NEURONTIN® (gabapentin), LYRICA® (pregabalin), eplivanserin, SONATA® (zaleplon), ESTORRA™ (eszopiclone), ZOPICLONE™ (imovane), DESYREL™ (trazodone hydrochloride), SERO- QUEL® (quetiapine fumarate), CLOZARIL® (clozapine), ZYPREXA™ (olanzapine), RISPERDAL® (risperidone), M100907 and LUNESTA™.

In one embodiment, the compounds of the invention are useful in combination with a mechanical therapy, such as CPAP. "CPAP" or "continuous positive airway pressure" is a mechanical device for the treatment for sleep apnea and other sleep-related breathing disorders (including snoring). Treatment with a CPAP device is typically administered via the nose or mouth of the patient.

Under CPAP treatment, a subject wears a tight-fitting plastic mask over the nose when sleeping. The mask is attached to a compressor, which forces air into the nose creating a positive pressure within the subject's airways. The principle of the method is that pressurizing the airways provides a mechanical "splinting" action, which prevents or lessens airway collapse and therefore, obstructive sleep apnea. Although an effective therapeutic response is observed in most subjects who undergo CPAP treatment, many subjects cannot tolerate the apparatus or pressure and refuse treatment. Moreover, recent covert monitoring studies demonstrated that long-term compliance with CPAP treatment is very poor. It is known that subjects remove their mask while sleeping.

In one aspect, the compound of the invention is administered in conjunction with a CPAP device to promote sleep. In another aspect, the compound of the invention is administered in conjunction with a CPAP device to improve sleep. In another aspect, the compound of the invention is administered in conjunction with a CPAP device to improve compliance regarding with CPAP treatment. Without wishing to be bound by theory, it is thought that by administering an effective amount of a sleep promoting compound of the invention to a subject in conjunction with CPAP treatment, the subject will sleep better and more soundly and therefore, not be as likely to remove the mask.

In one embodiment, the compound of the present invention is administered prior to the CPAP treatment. In another embodiment, the compound of the present invention is administered at substantially the same time as the CPAP treatment. In one embodiment, parallel administration of an effective amount of the compound is accomplished by adding an additional aerosol channel to the air pressure treatment portion of the CPAP device, thus administering the compound of the present invention in a nebulized form via the nasal or oral mask of the CPAP device. Alternatively, an effective amount of the compound can be added to the water or into the liquid reservoir that is typically part of the CPAP treatment device.

Using the CPAP mask treatment, the compound of the invention is administered in a low concentration throughout the night, or at higher concentrations, as a bolus, at different time points in the beginning and during the course of the night.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLE 1

Synthesis of Loxapine Analogs

The compounds of the invention, and related derivatives, can be synthesized by methods known to one skilled in the art.

EXAMPLE 2

Sleep-Inducing Properties of Compounds of the Invention

Sleep in mammals can be divided into sleep occurring during periods of rapid eye movement (REM), accompanied by substantial brain activity, and periods of non-REM (NREM) sleep, accompanied by decreased brain activity. Typically, a normal nighttime sleep period is occupied primarily by NREM sleep, and thus NREM cumulation can serve as a measure of total sleep cumulation, e.g., significantly decreased NREM can be associated with insomnia and an accumulation of "sleep debt", e.g., an accumulated physiological need for sleep that tends to persist until a sufficient amount of additional sleep is accumulated. Thus, an increase in NREM associated with a treatment can indicate the treatment's effectiveness in treating insomnia.

Sleep quality can be associated with sleep continuity or sleep maintenance. For example, a subject with sleep apnea wakes up numerous times during a sleep period, e.g., the subject has difficulty maintaining continuous sleep. Although such a subject can accumulate a typical nights length of sleep, e.g., 8 hours, the sleep is unrefreshing or non-restorative due to the waking caused by the sleep apnea. Thus, an increase in the longest uninterrupted sleep bout (LUSB, also known as longest sleep bout) associated with a treatment can indicate the treatment's effectiveness in enhancing sleep continuity, and therefore in treating sleep maintenance insomnia.

Sleep-wakefulness, locomotor activity and body temperature are monitored in male Wistar rats treated with a test compound (i.e., loxapine analog) initially at a concentration of 10 mg/kg. Higher and lower doses are assayed for select compounds (e.g., as high as 45 mg/kg, and as low as necessary to establish a no-effect dose). Treatments are administered at CT-18, the peak of the activity dominated period (6 hours after lights-off), and produce soporific (sleep-inducing) effects characterized by increased non-REM sleep time, increased sleep continuity, but without evidence of REM sleep inhibition or rebound insomnia.

Sleep-wakefulness, locomotor activity and body temperature were monitored in vivo with certain of the disclosed sleep-inducing agents (e.g., compounds 1, 2, 3, 5, 6, 7, 8, 9, 10, 12, 14, 17, 19, 20, 21, 23, 30, 31, 32, 39, 40, 42, 46, 50, 51, 52, 54, 56, and 58) and other compounds listed in Table 1. Adult, male Wistar rats (250 g at time of surgery, Charles River Laboratories, Wilmington Ma.) were anesthetized (2% isoflourane in medical grade oxygen) and surgically prepared with a cranial implant to permit chronic electro-encephalogram (EEG) and electromyogram (EMG) recording. Body temperature and locomotor activity were monitored via a miniature transmitter (Mini-Mitter, Bend, Oreg.) surgically placed in the abdomen. The cranial implant consisted of stainless steel screws (two frontal (+3.2 AP from bregma, ±2.0 ML) and two occipital (−6.9 AP, ±5.5 ML)) for EEG recording. Two Teflon®-coated stainless steel wires were positioned under the nuchal trapezoid muscles for EMG recording. All leads were soldered to a miniature connector prior to surgery, and gas sterilized in ethylene oxide. The implant assembly was affixed to the skull with dental acrylic. A minimum of three weeks was allowed for surgical recovery.

Each rat was permanently housed in its own individual recording cage located within separate, ventilated compartments of custom-designed stainless steel cabinets. Each cage was enhanced with a filter-top riser and low-torque swivel-commutator. Food and water were available ad libitum. A 24-hr light-dark cycle (12 hours light, 12 hours dark) was maintained throughout the study. Animals were undisturbed for at least 48 hours before and after treatments.

Sleep and wakefulness were determined using "SCORE-2000™" (Hypnion, Worcester, Mass.)—an internet-based sleep-wake and physiological monitoring system. The system monitored amplified EEG (bandpass 1-30 Hz), integrated EMG (bandpass 10-100 Hz), body temperature and non-specific locomotor activity (LMA) via telemetry, and drinking activity, continuously and simultaneously. Arousal states were classified on-line as non-REM (NREM) sleep, REM sleep, wake, or theta-dominated wake every 10 seconds. Total drinking and locomotor activity counts, and body temperature were quantitated and recorded each minute, using EEG feature extraction and pattern-matching algorithms. From this data, the longest uninterrupted sleep bout (LUSB) was obtained. The classification algorithm used individually-taught EEG-arousal-state templates, plus EMG criteria to differentiate REM sleep from theta-dominated wakefulness, plus behavior-dependent contextual rules (e.g., if the animal was drinking, it is awake). Drinking and locomotor activity intensity (LMA) were recorded every 10 seconds, while body temperature was recorded each minute. Locomotor activity was detected by a telemetry receiver (Mini-Mitter) beneath the cage. Telemetry measures (LMA and body temperature) were not part of the scoring algorithm; thus, sleep-scoring and telemetry data were independent measures.

Compounds were administered at CT-18, the peak of the activity-dominated period, sufficient time was allowed to view the time course of the treatment effect before lights-on (6 hours post-treatment). Compounds were suspended in sterile 0.25% or 0.5% methylcellulose (1-2 ml/kg). Treatments were administered orally as a bolus.

A paraellel group study design was employed. Vehicle controls were drawn from a large pool (N>200): a subset of the pooled vehicle controls was selected, based on computerized matching with the 24-hour pre-treatment baseline of the active treatment group.

The results of NREM and LUSB parameters were measured for the loxapine derivatives such as Compounds 1, 2, 3, 5, 6, 7, 8, 9, 10, 12, 14, 17, 19, 20, 21, 23, 30, 31, 32, 39, 40, 42, 46, 50, 51, 52, 54, 56, and 58 and other compounds listed in Table 1. Representative results are shown in Table 6.

TABLE 6

| Sleep Inducing Properties* of Compounds | | | | | | | |
|---|---|---|---|---|---|---|---|
| # | dose | NREM | LUSB | # | dose | NREM | LUSB |
| 1 | 1 | | 6.0 ± 2.3 | 21 | 1 | | |
|   | 3 | 39 ± 6 | 18.8 ± 3.0 |   | 3 | | 9.9 ± 1.8 |
|   | 10 | | 19.7 ± 6.7 |   | 10 | 49 ± 5 | 9.2 ± 3.4 |
| 2 | 1 | | | 23 | 1 | | |
|   | 3 | | | | 3 | | 4.8 ± 2.6 |
|   | 10 | 33 ± 7 | 12.6 ± 3.4 | | 10 | 28 ± 7 | 9.6 ± 2.0 |
| 3 | 1 | | | 30 | 1 | | |
|   | 3 | | | | 3 | | 9.2 ± 3.3 |
|   | 10 | 32 ± 8 | 6.1 ± 1.8 | | 10 | 30 ± 7 | 10.7 ± 2.4 |

TABLE 6-continued

| Sleep Inducing Properties* of Compounds | | | | | | | |
|---|---|---|---|---|---|---|---|
| # | dose | NREM | LUSB | # | dose | NREM | LUSB |
| 5 | 1 | | | 31 | 1 | | |
|   | 3 | | 13.5 ± 4.0 |   | 3 | | 17.5 ± 7.6 |
|   | 10 | 38 ± 9 | 8.7 ± 3.3 |   | 10 | 42 ± 8 | 20.7 ± 2.9 |
| 6 | 1 | | | 32 | 1 | | |
|   | 3 | | 10.5 ± 1.7 |   | 3 | | |
|   | 10 | 46 ± 5 | 17.0 ± 5.0 |   | 10 | 34 ± 8 | 16 ± 2.6 |
| 7 | 1 | | | 39 | 1 | | |
|   | 3 | | | | 3 | | |
|   | 10 | 27 + 9 | 11.3 ± 3.5 | | 10 | 33 ± 5 | 12.2 ± 2.7 |
| 8 | 1 | | | 42 | 1 | | |
|   | 3 | | | | 3 | | |
|   | 10 | 47 ± 10 | 16.7 ± 3.0 | | 10 | 14 ± 7 | 4.8 ± 2.7 |
| 9 | 1 | | | 46 | 1 | | 4.1 ± 1.6 |
|   | 10 | 36 ± 7 | 17.7 ± 4.2 |   | 3 | | 17 ± 4.4 |
|   | 30 | | 8.9 ± 3.7 |   | 10 | 50 ± 8 | 11.1 ± 3.7 |
| 10 | 1 | | 12.5 ± 3.1 | 50 | 1 | | |
|   | 3 | | 17.0 ± 4.9 |   | 3 | | |
|   | 10 | 37 ± 7 | 14.5 ± 3.2 |   | 10 | -11 ± 6 | 3.4 ± 2.6 |
| 12 | 1 | | 7.7 ± 3.2 | 51 | 1 | | |
|   | 3 | | 8.3 ± 3.0 |   | 3 | | |
|   | 10 | 49 ± 10 | 18.1 ± 2.1 |   | 10 | 49 ± 9 | 10.1 ± 3.6 |
| 14 | 1 | | | 52 | 1 | | |
|   | 3 | | -2.9 ± 1.8 |   | 3 | | |
|   | 10 | 26 ± 7 | 5.1 ± 1.4 |   | 10 | 24 ± 6 | 15.9 ± 2.3 |
| 17 | 1 | | | 54 | 1 | | |
|   | 3 | | | | 3 | | |
|   | 10 | 39 ± 10 | 5.0 ± 2.0 | | 10 | 23 ± 6 | 11.1 ± 2.9 |
| 19 | 1 | | | 56 | 1 | | |
|   | 3 | | 18.6 ± 3.3 |   | 3 | | |
|   | 10 | 44 ± 6 | 11.7 ± 4.0 |   | 10 | 20 ± 4 | 11.7 ± 2.3 |
| 20 | 1 | | | 58 | 1 | | |
|   | 3 | | | | 3 | | |
|   | 10 | -11 ± 5 | 4.7 ± 2.3 | | 10 | 34 ± 8 | 12.2 ± 2.5 |
| 40 | 3 | | 5.6 ± 2.1 | | | | |
|    | 10 | 30 ± 7 | 7.6 ± 4.2 | | | | |
|    | 30 | 43 ± 4 | 16.4 ± 2.9 | | | | |

*dose is in mg/kg; NREM and LUSB are in minutes.

EXAMPLE 3

Irwin Screen Side Effects

The Irwin screen can provide useful information on potential side effects of compounds on general physiological and behavioural functions. The screen is conducted by administering the test compounds orally in 0.25% aqueous methylcellulose using male Wistar rats, a frequently used species in such studies and for which background data are readily available.

The Irwin screen tests for numerous parameters in animals that have been administered the test compound. For example, the screen can include: in-cage effects, e.g., dispersion, respiratory rate, locomotor activity, restlessness, fighting, alertness, apathy, and exophthalmus; in-arena effects, e.g., transfer arousal, spatial locomotion, ptosis, startle, tail elevation, piloerection, touch escape, positional passivity, catalepsy, tighting reflex, visual placing, grip strength, pinna, corneal, pain response, and wire manoeuvre; parameters observed in handling, e.g., cyanosis, cutaneous blood flow, hypothermia, body tone, pupil size, light-pupil response, lacrimation, grooming, red staining, salivation, and provoked biting; general scores e.g., fearfulness, irritability, abnormal gait, abnormal body carriage, tremors, twitches, convulsions, bizarre behaviour, writhing, vocalisation, diarrhoea, number of defaecations, number of urinations, moribund, lethality, and abnormalities detected. Further details can be found in Irwin, S; Comprehensive observational assessment: I a. A systematic, quantitative procedure for assessing the behavioural and physiological state of the mouse. *Psychopharmacologia* (Berl.) 13: 222-257, 1968, the entire teachings of which are incorporated herein by reference.

Irwin screening of the disclosed sleep-inducing agents are performed by Covance (Princeton, N.J.) according to Irwin, above; Covance Standard Operating Procedure (current revision of SOP PHARM 8.10); relevant regulatory authority guidelines ICH (International Committee for Harmonization) Guideline (Topic S7A; CPMP/ICH/539/00) on Safety Pharmacology Studies for human pharmaceuticals (November 2000); and all procedures carried out on live animals are subject to the provisions of United Kingdom Law, in particular the Animals (Scientific Procedures) Act, 1986. which obliges all UK laboratories to maintain a local ethical review process to ensure that all animal use in the establishment is carefully considered and justified; that proper account is taken of all possibilities for reduction, refinement or replacement and that high standards of accommodation and care are achieved.

All chemicals used are purchased from Colorcon, Ltd, Dartford Kent, UK unless otherwise noted and are of ACS reagent grade purity or higher. All test compound formulations are prepared on the day of dosing by Covance Harrogate Dispensary. The test compounds are formulated in 0.25% aqueous methylcellulose at the highest concentration required. Lower doses are obtained by serial dilution of the highest concentration using 0.25% aqueous methylcellulose. Dose levels are expressed in terms of the amount of test compound administered without regard to purity or active content. All formulations are stored at room temperature (nominally 10 to 30° C.) in sealed containers and protected from light.

An adequate number of male Wistar (Crl:WI(Glx/BRL/Han) BR:WH) rats are obtained from Charles River Ltd. (Margate, Kent, United Kingdom). The rats are approximately 5 weeks of age and weigh between 150 and 170 g on arrival. The animals are housed in groups of no more than six in polypropylene cages (33×15×13 cm) or (45×28×20 cm) with solid floors and Grade 10 woodflakes (Datesand Ltd., Cheshire, United Kingdom) as bedding. The cages are cleaned and dried before use. Aspen chew blocks are placed within the cages as a form of environmental enrichment. Routinely, holding rooms are maintained within acceptable limits for temperature and relative humidity (nominally 19 to 25° C. and 40% to 70%, respectively). These rooms are illuminated by fluorescent light for 12 hours out of each 24 hour cycle and designed to receive at least 15 fresh air changes per hour. Diet (RM1.(E).SQC. (Special Diets Services Ltd. Witham, United Kingdom) and water from the mains tap supply are provided ad libitum (except during handling). These are routinely analysed for specific constituents and are not found to contain any biological or chemical entity which might interfere with the test system. On arrival, all animals are examined for ill-health. Animals are acclimatised for a period of at least 5 days. During this time, animals are identified by their cage labels. A veterinary examination is performed before the start of any experimental procedures to ensure their suitability for the study. Prior to the start of the study, animals are allocated randomly to treatment groups and individually tail-marked as they come to hand. At the end of the study, the animals are euthanized.

Each animal receives a single oral administration of vehicle or test article, using a constant dose of 1 mg/kg. Individual doses are based on individual body weights, obtained on the day of dosing.

The Irwin screen parameters above are systematically assessed in accordance with the relevant controls. In general, drug-induced changes, absent in normal animals, are scored using increasing integers with '0' being normal (+/−, present/absent may also be used). Parameters present in normal animals are scored using an integer that allows for increases and decreases to be recorded. Detailed observations are performed at 30, 60, 90, 180 and 300 minutes post-dose. The animals are kept for a 7-day post-dose period during which time they are observed daily for gross signs of toxicity and mortality.

EXAMPLE 4 hERG Side Effects of Disclosed Agents

The cardiac potassium channel, hERG, is responsible for the rapid delayed rectifier current (IKr) in human ventricles. This channel has been selected for evaluation because inhibition of IKr is the most common cause of undesirable cardiac action potential prolongation by non-cardiac drugs. Increased action potential duration causes prolongation of the QT interval that has been associated with a dangerous ventricular arrhythmia, torsade de pointes (Brown, A M; Rampe, D. (2000). Drug-induced long QT syndrome: is hERG the root of all evil?; and Pharmaceutical News 7, 15-20; Rampe, D; Roy, M L; Dennis, A; Brown, A M. (1997), the entire teachings of which are incorporated herein by reference). hERG channels were expressed in a human embryonic kidney (HEK293) cell line that lacks endogenous tKr. Expression in a mammalian cell line is preferable to transient expression in Xenopus oocytes because the latter shows a consistent 10-100 fold lower sensitivity to hERG channel blockers. See also, for example: A mechanism for the pro-arrhythmic effects of cisapride (Propulsid): high affinity blockade of the human cardiac potassium channel hERG. FEBS Lett. 417, 28-32; Weirich, J; Antoni, H. (1998); Rate-dependence of anti-arrhythmic and pro-arrhythmic properties of class I and class III anti-arrhythmic drugs. Basic Res Cardiol 93 *Suppl* 1, 125-132; and Yap, Y G; Camm, A J. (1999); and Arrhythmogenic mechanisms of non-sedating antihistamines. Clin. Exp. Allergy 29 *Suppl* 3, 174-181. The entire teachings of the preceding articles are incorporated herein by reference.

The in vitro effects of the disclosed sleep-inducing agents on the hERG (human ether-à-go-go-related gene) channel current (IKr, the rapidly activating, delayed rectifier cardiac potassium current) were determined by ChanTest (Cleveland, Ohio) according to Standard Operating Procedures of ChanTest.

All chemicals used were purchased from Sigma (St. Louis, Mo.) unless otherwise noted and were of ACS reagent grade purity or higher. Stock solutions of test articles and terfenadine (positive control) were prepared using dimethyl sulfoxide (DMSO) and stored frozen. Test article and positive control concentrations were prepared by diluting stock solutions into a HEPES (N-[2-hydroxyethyl]piperazine-N'-[2-ethanesulfonic acid])-buffered physiological saline (HB-PS) solution (composition in mM): NaCl, 137; KCl, 4.0; $CaCl_2$, 1.8; $Mg Cl_2$, 1; HEPES, 10; Glucose, 10; pH adjusted to 7.4 with NaOH (prepared weekly and refrigerated until use). Since previous results have shown that 0.3% DMSO does not affect channel current, all test and control solutions will contain 0.1% DMSO. If the final DMSO concentration must be greater than 0.3%, to reach a specified test article concentration, a separate vehicle control test with an n>2 was performed at the highest final DMSO concentration. Test and control solutions were prepared from stock solutions on a daily basis.

Cells used were human embryonic epithelial kidney cells (HEK293; source strain, American Type Culture Collection, Manassas, Va.; sub-strain, ChanTest, Cleveland, Ohio), transformed with adenovirus 5 DNA and transfected with hERG cDNA. Stable transfectants were selected by coexpression with the G418-resistance gene incorporated into the expression plasmid. Selection pressure was maintained by including G418 in the culture medium. Cells were cultured in Dulbecco's Modified Eagle Medium/Nutrient Mixture F-12 (D-MEM/F-12) supplemented with 10% fetal bovine serum, 100 U/mL penicillin G sodium, 100 µg/mL streptomycin sulfate and 500 µg/mL G418.

Data acquisition and analyses were performed using the suite of pCLAMP programs (Axon Instruments, Calif.). Steady state was a limiting constant rate of change with time (linear time dependence) before and after test article application. The decrease in current amplitude upon reaching steady state was used to calculate the percent block relative to control.

All experiments were performed at room temperature (18° C.-24° C.). Each cell acted as its own control. One concentration (10 µM) of each test article was applied to cells expressing hERG (n≧3, where n=the number cells). Duration of exposure to each concentration was limited to the time necessary to reach steady-state block, but no longer than 10 minutes. One concentration of the positive control article (60 nM terfenadine) was applied to two cells (n≧2). Cells were transferred to the recording chamber and superfused with HB-PS solution. Pipette solution for whole cell recordings were (composition in mM): potassium aspartate, 130; Mg Cl$_2$, 5; EGTA (ethylene glycol tetraacetate), 5; ATP(adenosine triphosphate), 4; HEPES, 10; pH adjusted to 7.2 with KOH. Pipette solution was prepared in batches, aliquoted, stored frozen, and a fresh aliquot thawed each day. Patch pipettes were made from glass capillary tubing using a P-97 micropipette puller (Sutter Instruments, Calif.). A commercial patch clamp amplifier was used for whole cell recordings. Before digitization, current records were low-pass filtered at one-fifth of the sampling frequency.

Onset and steady state block of hERG current due to test article were measured using a pulse pattern with fixed amplitudes (depolarization: +20 mV for 2 s; repolarization: −50 mV for 2 s) repeated at 10 s intervals, from a holding potential of −80 mV. Peak tail current was measured during the 2 s step to −50 mV. A steady state was maintained for at least 30 seconds before applying test article or positive control. Peak tail currents were measured until a new steady state was achieved.

Table 7 show the % blocking of the hERG channel at the indicated concentrations for various disclosed sleep inducing agents. Typically, values of about 10% or less are regarded as desirable, values from about 12% to about 30% can be acceptable if the compound has strong sleep-inducing performance and no other significant side effects; and values greater than about 30% are regarded as undesirable.

TABLE 7

| hERG Blocking | |
|---|---|
| Compound | hERG at 10 micromolar |
| 1 | 6.2% |
| 2 | 19% |
| 3 | 3.8% |

TABLE 7-continued

| hERG Blocking | |
|---|---|
| Compound | hERG at 10 micromolar |
| 4 | 8% |
| 5 | 36% |
| 6 | 27% |
| 7 | 42.8% |
| 8 | 49% |
| 9 | 59% |
| 10 | 14% |
| 12 | 7.20% |
| 14 | 0.30% |
| 17 | 30.10% |
| 19 | 9.90% |
| 20 | 5.30% |
| 21 | 0% |
| 23 | 8.90% |
| 30 | 4.50% |
| 31 | 3.80% |
| 32 | 1.60% |
| 35 | 0.10% |
| 39 | 61.40% |
| 40 | 5.6% |
| 42 | 5.80% |
| 44 | 65.90% |
| 46 | 20.40% |
| 50 | 45.00% |
| 51 | 32% |
| 52 | 19.80% |
| 54 | 6.10% |
| 56 | 0.30% |
| 58 | 0.20% |
| 72 | 10.90% |
| 86 | 86.90% |

EXAMPLE 5

Specificity for H1 Histamine Receptors

Binding assays were performed using the disclosed sleep-inducing agents and derivatives selected from those listed in Table 1 in competitive binding assays with known standards for the H1 histamine receptor, and the M1, M2, and M3 muscarinic receptors, alpha 1 and alpha 2 receptors, and D1 and D2 receptors.

The histamine H1 assays are described in Chang, et al., Heterogeneity of Histamine H$_1$-Receptors: Species Variation in [$^3$H]Mepyramine Binding of Brain Membranes. *Journal of Neurochemistry.* 32: 1653-1663 (1979); Martinez-Mir, M. I., Pollard, H., Moreau, J., et al. Three Histamine Receptors (H$_1$, H$_2$, and H$_3$) Visualized in the Brain of Human and Non-Human Primates. *Brain Res.* 526: 322-327 (1990); Haaksma, E. E. J., Leurs, R. and Timmerman, H. Histamine Receptors: Subclasses and Specific Ligands. *Pharmac. Ther.* 47: 73-104 (1990). The muscarinic assays are described in Buckley, N. J., Bonner, T. I., Buckley, C. M., and Brann, M. R. Antagonist Binding Properties of Five Cloned Muscarinic Receptors Expressed in CHO-K1 Cells. *Mol. Pharmacol.* 35: 469-476 (1989). The assays were performed according to the preceding articles, with the following modifications. Chemical reagents in the following were obtained from Sigma, St. Louis, Mo.

For the histamine H1 assays, the receptors were obtained from bovine cerebellar membrane tissue, with a B$_{max}$ (receptor number) of 6.2 femtomol/mg tissue (wet weight) and a KD (binding affinity) of 1.3 nM. A radioactive ligand ([$^3$H]pyrilamine (15-25)Ci/mmol), $K_i$ 1.9 nM, final concentration 2.0 nM) was employed, and 10 μM triprolidine ($K_i$ 3.3 nM) was employed as a non-specific determinant, reference compound, and positive control. The receptor and the radioactive ligand were combined with the test compound at a range of test compound concentrations from about $10^{-10}$ to about $10^{-6}$ M, and the mixture was incubated out in 50 mM Na-KPO$_4$ (pH 7.5) at 25° C. for 60 minutes. The reaction was terminated by rapid vacuum filtration onto glass fiber filters. Radioactivity from the displaced radioactive ligand trapped onto the filters was determined and compared to control values in order to measure any interactions of the test compound with the histamine H1 binding site.

For the muscarinic assays, the receptors were obtained from human recombinant receptors expressed in CHO cells (PerkinElmer, Inc., Wellesley, Mass.). The radioactive ligand employed was [$^3$H]-scopolamine, N-methyl chloride (80-100 Ci/mmol). (−)-Methylscopolamine bromide, 1.0 μM, was employed as the non-specific determinant, reference compound, and positive control. After incubation, reactions were terminated by rapid vacuum filtration onto glass fiber filters. Radioactivity from the displaced radioactive ligand trapped onto the filters was determined and compared to control values in order to measure any interactions of the test compound with the respective receptor.

For the M1 receptor assay, the $B_{max}$ (receptor number) was 4.2 picomol/mg protein, and the $K_D$ (binding affinity) of the receptor was 0.05 nM. The radioactive ligand was employed at a final concentration 0.5 nM, while the (−)-methylscopolamine bromide had a $K_i$ of 0.09 nM. The receptor and the radioactive ligand were combined with the test compound at a range of test compound concentrations from about $10^{-12}$ to about $10^{-5}$ M, incubated in Dulbecco's Phosphate Buffered Saline (PBS) for 60 minutes at 25° C., and worked up as described above.

For the M2 receptor assay, the $B_{max}$ (receptor number) was 2.1 picomol/mg protein, and the $K_D$ (binding affinity) of the receptor was 0.29 nM. The radioactive ligand was employed at a final concentration 0.5 nM, while the (−)-methylscopolamine bromide had a $K_i$ of 0.3 nM. The receptor and the radioactive ligand were combined with the test compound at a range of test compound concentrations from about $10^{-12}$ to about $10^{-5}$ M, incubated in Dulbecco's Phosphate Buffered Saline (PBS) for 60 minutes at 25° C., and worked up as described above.

For the M3 receptor assay, the $B_{max}$ (receptor number) was 4.0 picomol/mg protein, and the $K_D$ (binding affinity) of the receptor was 0.14 nM. The radioactive ligand was employed at a final concentration 0.2 nM, while the (−)-methylscopolamine bromide had a $K_i$ of 0.3 nM. The receptor and the radioactive ligand were combined with the test compound at a range of test compound concentrations from about $10^{-12}$ to about $10^{-5}$ M, incubated in 50 mM TRIS-HCl (pH 7.4) containing 10 mM MgCl$_2$, 1 mM EDTA for 60 minutes at 25° C., and worked up as described above.

Adenosine, purinergic $A_1$ binding assay was performed according to published procedures. See, e.g., Bruns, et al., *Naunyn Schmiedebergs Arch. Pharmacol.*, 335(1): 59-63 (1987), with minor modifications; and Ferlany, et al. *Drug Dev. Res.* 9: 85-93 (1986).

Adenosine, purinergic $A_2$ binding assay was performed according to published procedures. See, e.g., Jarvis, et al., *J. Pharmacol. Exper. Ther.* 251(3): 888-93 (1989) with modifications; and Bruns, et al., *Mol. Pharmacol.* 29(4): 331-46 (1986) with modifications Dopamine, $D_1$ (human recombinant) binding assay was performed according to published procedures. See, e.g., Jarvie, et al. *J. Recept Res.*, 13(1-4): 573-90 (1993); and Billard, et al. *Life Sciences*, 35(18): 1885-93 (1984), with modifications Dopamine, $D_1$ (human recombinant) binding assay was performed according to published procedures. See, e.g., Jarvie, et al. *J. Recept Res.*, 13(1-4): 573-90 (1993); and Gundlach, et al. *Life Sciences*, 35(19): 1981-8 (1984) with modifications Binding to H1 can be an indication of the desired sleep-inducing activity of the compound. Binding to muscarinic receptors shows non-specific binding, and can indicate anticholinergic activity which can result in undesired side effects, e.g., the side effects of many known antihistamines, e.g., blurred vision, dry mouth, constipation, urinary problems, dizziness, anxiety, and the like. A decrease in the binding of the compounds to the M1-M3 receptors, relative the binding of the compound to the H1 receptor, is an indication of the greater specificity of the compound for the histamine receptor over the muscarinic receptor. Moreover, a drug with increased specificity for the histamine receptor would possess less anticholinergic side effects.

Table 8 shows the inhibition constant $K_i$ in nM for H1 and the muscarinic receptors. It can be seen that the disclosed compounds are highly specific for H1 over the muscarinic receptors. Thus, the disclosed compounds can be expected to exhibit good sleep-inducing performance with limited side effects associated with muscarinic receptor inhibition.

TABLE 8

Specificity for H1 Histamine Receptors

| CMPD # | H1 (bovine) | M1 | M2 | M3 | Alpha1 | Alpha2 | D1 | D2 |
|---|---|---|---|---|---|---|---|---|
| 1 | 40.3[1] | >10,000 | >10,000 | >10,000 | >10,000 | >10,000 | >10,000 rat and human | >10,000 rat and human |
| 2 | 51.4 | >10,000 | >10,000 | >10,000 | >10,000 | >10,000 | >10,000 | >10,000 |
| 3 | 7.33 | >10,000 | >10,000 | >10,000 | >10,000 | >10,000 | 4920 | 1190 |
| 4 | | >10,000 | | >10,000 | >10,000 | >10,000 | >10,000 | >10,000[3] |
| 5 | 23.9 | >10,000 | >10,000 | >10,000 | 3020 | >10,000 | 4520 | 1610 |
| 6 | 13.8 | >10,000 | >10,000 | >10,000 | 2730 | >10,000 | 7170 | 96.1 |
| 7 | 217 | >10,000 | >10,000 | >10,000 | >10,000 | >10,000 | 1730 | 222 |
| 8 | 11.7 | >10,000 | >10,000 | >10,000 | >10,000 | >10,000 | 3350 | 434 |
| 9 | 36 | >10,000 | >10,000 | >10,000 | >10,000 | >10,000 | 1120 | 53.3 |
| 10 | 39.6 | >10,000 | >10,000 | >10,000 | >10,000 | >10,000 | 3160 | 1670 |
| 12 | 137 | >10,000 | >10,000 | >10,000 | >10,000 | >10,000 | 5220 | 1240 |
| 14 | 283 | >10,000 | >10,000 | >10,000 | >10,000 | >10,000 | 942 | >10,000 |
| 17 | 12 | >10,000 | >10,000 | >10,000 | 1990 | | 3450 | 883 |
| 19 | 39.5 | >10,000 | >10,000 | >10,000 | >10,000 | >10,000 | 6800 | 3160 |

TABLE 8-continued

Specificity for H1 Histamine Receptors

| CMPD # | H1 (bovine) | M1 | M2 | M3 | Alpha1 | Alpha2 | D1 | D2 |
|---|---|---|---|---|---|---|---|---|
| 20 | 76.8 | >10,000 | >10,000 | >10,000 | 1960 | >10,000 | 1930 | 1590 |
| 21 | 57.2 | >10,000 | >10,000 | >10,000 | >10,000 | >10,000 | >10,000 | >10,000 |
| 23 | 135 | >10,000 | >10,000 | >10,000 | >10,000 | >10,000 | >10,000 | >10,000 |
| 30 | 90.6 | >10,000 | >10,000 | >10,000 | >10,000 | >10,000 | 5060 | >10,000 |
| 31 | 239; 337; 224 | >10,000 | | >10,000 | >10,000 | >10,000 | 873 | 2200 |
| 32 | 3770 | >10,000 | >10,000 | >10,000 | >10,000 | >10,000 | >10,000 | >10,000 |
| 35 | | >10,000 | | >10,000 | >10,000 | >10,000 | >10,000 | >10,000 |
| 39 | 98.7 | >10,000 | >10,000 | >10,000 | >10,000 | >10,000 | >10,000 | >10,000 |
| 40 | $22.8^2$ | >10,000 | >10,000 | >10,000 | >10,000 | >10,000 | >10,000 rat and human | >10,000 rat 1870 in human |
| 42 | 1120 | >10,000 | | >10,000 | >10,000 | >10,000 | >10,000 | >10,000 |
| 44 | 41.4 | >10,000 | | >10,000 | >10,000 | >10,000 | | |
| 46 | 18.8 | >10,000 | | >10,000 | >10,000 | >10,000 | >10,000 | >10,000 |
| 48 | 27.1 | >10,000 | | >10,000 | >10,000 | | | |
| 50 | 31.8 | >10,000 | >10,000 | >10,000 | 595 | 1,950 | 1140 | 360 |
| 51 | 27.8 | >10,000 | >10,000 | >10,000 | 148 | 966 | 1040 | 170 |
| 52 | 55.4 | >10,000 | >10,000 | >10,000 | >10,000 | >10,000 | | >10,000 |
| 54 | 40.4 | >10,000 | >10,000 | | 1210 | 5820 | 4970 | 1080 |
| 56 | 117 | >10,000 | | >10,000 | >10,000 | >10,000 | >10,000 | >10,000 |
| 58 | | >10,000 | >10,000 | >10,000 | >10,000 | >10,000 | 2000 | 4030 |
| 72 | | >10,000 | | >10,000 | >10,000 | | 514 | 470 |

[1] 11.5 in rat, 23.7 in human;
[2] 58.8 in rat, 31.7 in human;
[3] 2730 in rat

EXAMPLE 6

Evaluation of Loxapine Analogs

The following pharmacokinetic parameters are computed from the individual plasma contrations of the modified antihistamine compound using a noncompartmental approach and appoprriate validated pharmacokinetic software (e.g., WinNonlin Professional). Concentration values reported as BLQ are set to zero. If concentration data are available, interim calculations are done (non-QC.d data) between periods if possible. Dose escalation does not depend on pharmacokinetic calculations.

Descriptive statistics, including mean, standard deviation, coefficient of variation, geometric mean, median, minimum and maximum are computed for each pharmacokinetic parameter by dose group. Descriptive statistics for natural-log transformed AUC(0-t), AUC(0-inf), and Cmax are provided for each dose level. In addition, mean and median concentration versus time graphs are provided.

Dose proportionality following study medication is explored by analyzing natural log-transformed pharmacokinetic variables AUC(0-t), AUC(0-inf), and Cmax with a linear model including the natural log-transformed dose as covariates. Dose proportionality is concluded if the 95% confidence interval for the slope of the covariate includes the value of 1. Dose linearity for AUC(0-t), AUC(0-inf), and Cmax is also explored by a linear model. See, e.g., Gibaldi and Perrier, *Pharmacokinetics*, Second Ed., Marcel Dekker: New York, N.Y. (1982). Nominal sample collection times were used in calculations, except where actual sampling times fell outside the protocol-specified acceptable time ranges. The following parameters were estimated:

$C_{max}$ Maximum plasma concentration.
$T_{max}$ Time to maximum concentration.
$C_{max}$ and $T_{max}$ were reported directly from the concentration-time data.

$AUC_{0-t}$ Area under the plasma concentration-time curve from time 9 to the last time point with measurable concentrations, estimated by linear trapezoidal rule.
$AUC_{0-00}$ Area under the plasma concentration-time curve extrapolated to infinity, calculated using the formula:

$$AUC_{0\text{-}00} = AUC_{0\text{-}t} + C_0/\lambda_0$$

Where $C_t$ is the last measurable concentration in plasma and $\lambda_z$ is the terminal phase elimination rate constant estimated using log-linear regression during the terminal elimination phase. The number of points used in $\lambda_z$ calculation was determined by visual inspection of the data describing the terminal phase. At lest the last three time points with measurable values were used in $\lambda_z$ calculation. The number of points used in $\lambda_z$ calculation is based on the best correlation ($r_2$ adjusted) obtained for the time points describing the terminal elimination phase. A $r_2$ adjusted value for the regression line is considered to accurately define the terminal elimination phase if the value is >0.7.

$T_{1/2}$ Elimination half-life, determined by $\ln(2)\lambda_z$.
CL Systemic clearance; for intravenous bolus or infusion, calculated using the formula:

$$CL = Dose/AUC_{0\text{-}00}$$

Report CL/F, where F=Absolute bioavailability, for all other routes of administration.
$V_2$ Volume of distribution for all routes of administration, calculated using the formula:

$$V_z = CL\,\lambda_z$$

CL/F is used to calculate $V_2/F$ for extravascular routes of administration.

Pharmacokinetic analysis is performed using WinNonlin Professional Edition (Pharsight Corporation, Version 3.3 or 4.1). Descriptive statistics such as mean and standard deviation are calculated in Microsoft Excel (Version 8.0e).

Metabolism of test articles in monkey and human cryopreserved hepatocytes was assayed as follows:

| MATERIALS | |
| --- | --- |
| Materials | Manufacturer, lot number and exp. Date |
| Hepatocytes from Cellzdirect | Monkey Human |
| Williams E medium | Sigma W1878, exp 2004-11 |
| Foetal calf serum | Fisher BW 14-501F, lot 01104637, exp 17 Feb. 2010 |
| 0.45 Trypan Blue | Biowhittaker 17-942E, lot 01104637, exp Jan. 14 |
| Test Material Stock Solution | CB-1/III/6 |
| DMSO | Fisher BP231-100, lot 041215, exp 12 Jul. 2009 |
| 10 mM ethoxycoumarin in methanol | PSLB 22-A-15, exp Sep. 25, 2004 |
| ACN | Fisher A998-4, lot 041181, exp June 2007 |
| Formic Acid | Fisher 032879, exp Mar. 14, 2006 |

Pre-Incubation Preparation:

Sample is diluted with DMSO, to prepare 100 μM and 10 μM stocks. 0.1% formic acid in acetonitrile is prepared by the addition of 1 mL formic acid per 1 L acetonitrile (store RT for 3 months). 10 minute, 60 and 120 minute 96 well quenching plates are prepared with 150 μL acetonitrile+0.1% formic acid in each well. Store on ice or refrigerated.

Next, hepatocytes are thawed and 100 μL of cell suspension is placed into a microfuge tube with 100 μL 0.4% Trypan Blue solution and gently mix by inversion. A small amount of the stained cell suspension (approximately 15 μL) is placed into a clean hemacytometer with a coverslip. The hemacytometer is placed onto the stage of the microscope and the focus and power are adjusted until a single counting square fills the field. The number of cells in the four outside corner subdivided squares of the hemacytometer are counted. Viable cells are opalescent, round, and pale with a darker outline. Non-viable cells are dark, opaque blue.

The % viability is calculated as the number of viable cells divided by the total of cells×100.

The viable cell density and total number of viable cells are calculated: Viable cell Density (D)=Mean 3 of viable cells counted (C)×$10^{4\times f/2}$; Total number of viable cells (E)=D×26 (resuspension volume). The additional media required to achieve a concentration of 1×10$^6$ cells/mL is calculated:

$$\text{Volume of additional medium} = \frac{\text{total viable cells}}{1 \times 10^6}(E) - 26 \text{ mL}$$

Cells are diluted accordingly and stored at room temperature.

Incubations

198 μL of hepatocytes are transferred to relevant wells on dosing plate. The remaining hepatocyte suspension is combined and placed in a suitable container of near boiling water and left for 5 minutes to inactivate the cells (for inactive controls and standard curve preparation).

198 μL of inactive hepatocytes are transferred to control wells and 198 μL of blank media are transferred to buffer control wells. Plates are preincubated for at least 15 min. Reactions are started 2 μL of appropriate test compound dilution from dosing plate. Plates are incubated in an incubator set at 37° C. for approximately 10 minutes, then 50 μL of incubate is removed to 10 a minute quenching plate containing 150 μL acetonitrile+0.1% formic acid and stored refrigerated or on ice. Following 60 minutes, 50 μL of incubate is removed to 60 minute quenching plate containing 150 μL acetonitrile+0.1% formic acid and stored refrigerated or on ice. Following 120 minutes, 50 μL of incubate is removed to 120 minute quenching plate containing 150 μL acetonitrile+0.1% formic acid and stored refrigerated or on ice. The remaining 50 μL is frozen in incubation plates. Tubes are then centrifuged at ~4° C. at ~1400×g for ~10 minutes. 100 μL of supernatant is diluted with 100 μL water in analysis plates, plates are stored frozen at −20° C. prior to analysis.

Preparation of Standard Curves 0.1 μM standard is prepared by the addition of 2 μL of 10 μM dosing solutions to 198 μL of inactive hepatocytes in standard prep plate. 150 μL acetonitrile+0.1% formic acid is added to the standard quenching plate. 150 μL of 0.1 μM standard is transferred into one column of a standard plate. 75 μL inactive hepatocytes is added to remaining wells. 75 μL from 0.1 μM standard is transferred into adjacent well in column in the plate, and mixed well by titration. Serial dilution is continued. 75 μL is removed from final standard (all wells contain 75 μL). Plates are incubated at approximately 37° C. for 10 minutes. 50 μL is transferred into standard quench plate containing 150 μL acetonitrile+0.1% formic acid. Plates are centrifuged along with samples and dilute supernatant 1:1 with water as above. Samples are stored frozen at ~−20° C.

For compound 5, the hepatocytes remaining 120 minutes after treatment at 1 μm, was 75.105 for primate and 90.405 for human.

EXAMPLE 7

Clinical Evaluation of Loxapine Analogs

The goal of a human clinical trial is to collect data on the effects of loxapine derivatives. Such data includes, for example, clinical signs and symptoms from physical exam, adverse events, laboratory safety (e.g., hematology, serum clinical chemistry, urinalysis), vital signs (e.g., blood pressure, heart rate, temperature, respiratory rate), and electrocardiogram (ECG) data.

The clinical trials are conducted as follows:

I. Subject Selection

A minimum of 18 subjects are used (2 enrollment groups of 9 subjects each). Subject candidates fulfilling the following inclusion criteria are eligible for participation in the study:

Healthy adult male subjects, 18-45 years of age.

Weighing at least 60 kg and within 15% of their ideal weights (see Table of Desirable Weights of Adults, Metropolitan Life Insurance Company, 1983).

Medically healthy subjects with clinically insignificant screening results (e.g., laboratory profiles, medical histories, ECGS, physical exam).

Subject candidates fulfilling one of the following exclusion criteria are ineligible for participation in the study:

History or presence of significant cardiovascular, pulmonary, hepatic, renal, hematologic, gastrointestinal, endocrine, immunologic, dermatologic, neurologic, or psychiatric disease.

History or presence of sleep disorders.

History of chronic or seasonal allergies requiring treatment with H1 receptor antagonists (i.e., terfenadine, astemizole) within the 90 days prior to the study.

History or presence of alcoholism or drug abuse within the past 2 years.

Tobacco or nicotine use within the 90 days prior to the study.

Known hypersensitivity or idiosyncratic reaction to the study drug, possible excipients of the study formulation (Captisol®; sodium saccharin, F.C.C.; glycerin, U.S.P.; orange flavor; methylcellulose 400 centipoise, U.S.P.; opurified water), or related compounds.

Donation (standard donation amount or more) of blood or blood products within 90 days prior to the study.

Participation in another clinical trial within 90 days prior to the first dose.

History or presence of any disease, medical condition, or surgery, which may have an effect on drug absorption, metabolism, distribution, or excretion.

Weight loss or gain (±10%) within 30 days prior to the study.

Regular consumption of (e.g., more days than not) excessive quantities of caffeine-containing beverages (e.g., more than 5 cups of coffee or equivalent per day) within 30 days prior to the study.

Any condition that, in the opinion of the Investigator or Sponsor makes the subject unsuitable for the study.

Use of any prohibited prior or concomitant medications.

Each subject who completes the study screening assessments, meets all eligibility criteria, and is accepted for the study is assigned a unique identification number and receives designated doses of the modified antihistamine and placebo according to a randomization scheme. The randomization scheme is available only to the clinic pharmacy staff preparing the drug (who are not involved in the administration of the drug) and is not made available to the subjects, analysts, or members of the staff responsible for the monitoring and evaluation of the adverse experiences.

Subjects may be withdrawn from the study by the Principal Investigator for the following reasons:

Secondary occurrence of a major exclusion criteria.
To protect their health.
Adverse events.
Difficulties in blood collection.
To protect the integrity of the study.
Protocol violation.
Failure to comply with study directions.

The clinical report includes reasons for subject withdrawals as well as details relevant to withdrawal. Subjects withdrawn from the trial prior to study completion undergo all procedures scheduled for study completion. Subjects withdrawn due to any adverse event (whether serious or non-serious) or clinically significant abnormal laboratory test values are evaluated by the Investigator, or a monitoring physician, and are treated and/or followed up until the symptoms or values return to normal or acceptable levels, as judged by the Investigator.

II. Study Restrictions

Subjects do not take prescription or over-the-counter medication (including herbal products) during the 7 days preceding the study until the final sample of the final pharmacokinetic sampling period has been collected. Additionally, consumption of foods and beverages containing the following substances is prohibited as indicated:

Methylxanthine: 72 hours before each dosing and throughout the period of sample collection, i.e., caffeine beverages and equivalents (e.g., chocolate bars) are prohibited.

Alcohol: 72 hours before each dosing and throughout the period of sample collection.

All medications taken during the 30 days prior to study start are recorded. Any medications taken for chronic or seasonal allergies in the 90 days prior to the study is recorded.

Pre-Study Subject Screening: The Informed Consent Form is administered at screening. Within 14 days prior to dosing, medical history and demographic data, including name, sex, age, race, body weight (kg), height (cm), alcohol use, and tobacco use are recorded. Each subject receives a physical examination including complete vital signs, 12-lead ECG, and laboratory tests as specified. The laboratory tests include the following:

a) Hematology including hemoglobin, MCV, red blood cell count, hematocrit, MCHC, white blood cell count with differential platelet count and MCH;

b) Serum Chemistry including bun, albumin, ALT (SGOT), creatinine, alkaline phosphatase, glucose, total bilirubin, creatine phosphokinase (CPK), sodium, uric acid, AST (SGOT) and triglycerides;

c) Urinalysis including appearance and color, glucose, nitrite, pH, ketones, urobilinogen, specific gravity, bilirubin, leukocytes, protein and blood;

d) Additional Tests including HIV, urine drug screen, HbsAg, cannabinoids, HCV, benzodiasepines, HCV, amphetamines, hepatitis A (IgM), opiates, alcohol, cocaine, and continine.

Subject Management: Subjects are housed from at least 36 hours before dosing until completion of the 24-hour postdose events. They will return for a follow-up visit one week following the final dose or upon early withdrawal.

Subjects remain semi-recumbent in bed for the first 4 hours following drug administration. However, should adverse events occur at any time, subjects are placed in an appropriate position or are permitted to lie down on their right side. Subjects do not engage in strenuous activity at any time during the confinement period.

Standard meals are provided on Day 1 and Day 2. On Day 1, subjects are required to fast for a minimum of 10 hours overnight before dosing and for at least 4 hours thereafter. However, if the option for a previous dose in the fed state is used in Period 3 of Group 2, a standard high-fat meal is given 30 minutes prior to dose. In this case, the high-fat breakfast (i.e., approximately 50% of calories from fat) consists of two eggs fried in butter, two strips of bacon, two slices of buttered toast, four ounces of hash brown potatoes, and eight ounces of whole milk. Foods and beverages containing caffeine or equivalent (e.g., chocolate bars) are prohibited during confinement.

Water is not permitted from 2 hours before until 2 hours after dosing. Water is allowed at all other times. Standard meals are provided at approximately 4 and 9 hours after dosing, and at appropriate times thereafter.

III. Drug Administration

Subjects receive the dose for each period as assigned according to the randomization schedule for dosing sequence for each dose (enrollment) group. Subjects receive the assigned dose in a glass dosing cup, and within each dose group, all doses, active and placebo, are administered at the same volume to maintain the double-blind. Subjects are instructed to swallow the dose.

A total of 240 mL of water is given with dosing. A designated portion of the water (assigned by pharmacist based on dosing volume) is added to the emptied dosing cup, swirled to rinse, and swallowed by the subject. This process is repeated twice and then the remainder of the water is consumed by the subject.

The starting dose for the first human dose level is based on the toxicity and safety profiles in the preclinical studies. The equivalent body surface area conversion from human to rat is ⅙ (Toxicological Handbook, Michael J. Dereleko, CRC press, Boca Raton, Fla.). Based on NOAEL of 30 mg/kg/day for rat and body surface equivalent criteria, the equivalent dose in an individual of 60 kg is 300 mg/day (⅙×30 mg/kg/day [rat NOAEL]×60 kg). Based on NOAEL dose in rat (30 mg/kg/day), the dose of 3 mg is approximately ⅒ of the NOAEL dose in rats. The highest dose proposed of 160 mg is also below the NOAEL in rats.

If a dose limiting toxicity (Grade 3 or 4 according to the grade scale modified from the WHO Common Toxicity Criteria—Appendix I) deemed to be related to the study medication is observed in any 2 of the 6 subjects at any dose level, dose escalations are stopped, and the prior dose is considered the maximum tolerated dose (MTD).

If one subject at any dose level experiences a dose limiting toxicity, the Principal Investigator (in consultation with the Sponsor) decides, using good clinical judgment, whether to proceed to the next dose level as planned, or to adjust the next dose level downward from the dose planned. This consultation is done for all groups following the previous dose group to decide whether to proceed with planned doses or to adjust doses downward. Additionally, the planned doses may be substituted with intermediate doses if emerging safety or tolerability issues become apparent (i.e., there does not have to be a Grade 3 or 4 event) from the preceding dose that suggests the need to escalate more slowly.

Dose increments is only permitted if, in the opinion of the Principal Investigator, adequate safety and tolerability have been demonstrated at the previous lower dose. In all cases, the Principal Investigator uses good clinical judgment to decide whether to adjust the dose or to stop the study based on an assessment of all factors relevant to the safety of the subjects.

The Principal Investigator reviews check-in data (e.g., physical examination results, vital signs, questionnaire, and clinical laboratory results (e.g., serum chemistry, hematology, urinalysis, and urine drug screen)) for clinically significant changes since screening or the previous period. The Principal Investigator determines if the subject will be dosed or withdrawn for the study based on this review.

IV. Clinical Observation

A hematology panel, a serum chemistry panel and a urinalysis is performed at screening, at each check-in, 24 hours following each dose, and one week following the final dose, or upon early withdrawal. Blood samples (approximately 7 mL) are collected from an indwelling intravenous catheter into evacuated glass tubes containing sodium heparin predose and at 0.25, 0.5, 0.75, 1.0, 1.5, 2, 3, 4, 6, 8, 10, 12, 18, and 24 hours postdose. Urine samples are collected predose and during the 0-8 hour interval each period. Samples collected during the interval are not pooled. Each void is considered a sample. The voiding times are at will, not scheduled (with the exception of the predose void and the void at the end of the 8 hour interval).

Vital signs are measured during the screenings. When the time of vital signs coincides with an ECG only, the vital signs are taken 10 minutes prior to the ECG. When the time of vital signs coincides with a blood draw or a blood draw and ECG, the vital signs are taken 10 minutes prior to the blood draw. Respirations and temperature is monitored at check-in, 24 hours following each dose, and one week following the final dose, or upon early withdrawal. Single measurements of blood pressure and heart rate are taken after a minimum of 5 minutes in a semi-recumbent position. Measurements taken during study confinement are monitored with an AVS machine at check-in; 0 (predose); 0.25, 0.5, 0.75, 1, 1.5, 2, 3, 4, 6, 8, 10, 12, 18, and 24 hours postdose; and one week following the final dose, or upon early withdrawal. For any heart rate measurement greater than 100 beats per minute, the heart rate will be rechecked two minutes later. On Day 1, at approximately 24 hours prior to dosing, 3 measurements of blood pressure and heart rate, taken 2 minutes apart, are taken as described as described above.

A standard 12-lead ECG is performed for each subject at screening, on Day 1 at times coinciding with Day 1 times of 1 hours prior to dose and 1, 1.5, 2, 3, 4, and 6 hours postdose; on Day 1 at 1 hour predose and 1, 1.5, 2, 3, 4, 6, and 24 hours postdose; and one week following the final dose or upon early withdrawal. Additional ECGs may be performed at other times if deemed necessary. All standard 12-lead ECGs are recorded for 10 seconds. Timing and registration technique for ECGs is standardized for all subjects. Subjects should be lying down for at least 1 minute prior to each 12-lead ECG evaluation. The Principal Investigator evaluates PR, QRS, QT, and QTc intervals. When the time of ECGs coincides with a blood draw, the ECG will be taken following the draw.

A physician examines each subject at screening, each check-in, 24 hours following each dose, and one week following the final dose, or upon early withdrawal. Additional examinations are performed at other times if deemed necessary.

Immediately before vital signs measurements 1 hour predose and at 1, 2, 6, and 24 hours postdose (the vital signs are taken 10 minutes prior to the blood draw designated at these times), subjects are presented a visual analogue scale and asked to draw a vertical mark across a 100 mm line at the point ranging between Very Sleepy and Alert/Wide Awake, which best describes their level of alertness at that time.

The subjects are instructed to inform the study physician or staff of any adverse events or intercurrent illnesses experienced during the trial. Additionally, a specific inquiry regarding adverse events is conducted prior to dosing, at 2, 4, 8, and 24 hours postdose, and one week following the final dose, or upon early withdrawal. Questions are posed in a non-specific manner so as not to bias the response.

Any subject who has any adverse event (whether serious or non-serious) or clinically significant abnormal laboratory test values is evaluated by the Investigator, or a monitoring physician, and is treated and/or followed up until the symptoms or values return to normal or acceptable levels, as judged by the Investigator. A physician, either on-site or at a nearby hospital emergency room, administers treatment of any serious adverse events. Where appropriate, medical tests and examinations are performed to document resolution of event(s). Outcome is classified as, e.g., resolved, improved, unchanged, worse, fatal, or unknown (lost to follow-up).

V. Reporting

All adverse events occurring during the clinical trial are recorded. Adverse events are coded using MedDRA (version 4.1). An adverse event/experience (AE) is any unwarranted medical occurrence in a patient or clinical investigation subject administered a pharmaceutical product that does not necessarily have a causal relationship with this treatment (ICH/WHO). An adverse event (AE) is, therefore, any unfavorable and unintended sign, (including, for example, an abnormal laboratory finding), symptom, or disease temporally associated with the use of a medical product, whether or not considered related to the medical product (ICH/WHO).

The Investigator reviews each event and assesses its relationship to drug treatment (i.e., unrelated, unlikely, possibly, probably, almost certainly). Each sign or symptom reported is graded on a 3-point severity scale (mild, moderate, or severe) and the date and time of onset, time relationship to drug dosing, duration, and outcome of each event is noted. The following definitions for rating severity are used: (1) Mild: The adverse event is easily tolerated and does not interfere with daily activity; (2) Moderate: The adverse event interferes with daily activity, but the subject is still able to function; (3) Severe: The adverse event is incapacitating and requires medical intervention.

If any of the above adverse events are serious, special procedures are followed. All serious adverse events are reported to the Sponsor within 24 hours and followed by written reports within 48 hours, whether or not the serious events are deemed drug-related.

A Serious Adverse Event (SAE) is any untoward medical occurrence that, at any dose, results in death, is life-threatening, results in permanently disability or incapacitation, requires inpatient hospitalization, prolongs inpatient hospitalization, is a congenital anomaly, may jeopardize the subject or may require intervention to prevent one or more of the other outcomes listed above.

VI. Pharmacokinetics

The following pharmacokinetic parameters are computed from the individual plasma concentrations of the modified antihistamine compound using a noncompartmental approach and appropriate validated pharmacokinetic software (e.g., WinNonlin Professional). Concentration values reported as BLQ are set to zero. If concentration data are available, interim calculations are done (non-QC.d data) between periods if possible. Dose escalation does not depend on pharmacokinetic calculations.

Descriptive statistics, including mean, standard deviation, coefficient of variation, geometric mean, median, minimum and maximum are computed for each pharmacokinetic parameter by dose group. Descriptive statistics for natural-log transformed AUC(0-t), AUC(0-inf), and Cmax are provided for each dose level. In addition, mean and median concentration versus time graphs are provided.

Dose proportionality following study medication is explored by analyzing natural log-transformed pharmacokinetic variables AUC(0-t), AUC(0-inf), and Cmax with a linear model including the natural log-transformed dose as covariates. Dose proportionality is concluded if the 95% confidence interval for the slope of the covariate includes the value of 1. Dose linearity for AUC(0-t), AUC(0-inf), and Cmax is also explored by a linear model.

VII. Assessment of Safety

A by-subject treatment-emergent adverse event data listing including verbatim term, preferred term, treatment, severity, and relationship to treatment is provided.

The number of subjects experiencing adverse events and number of adverse events is summarized by dose level using frequency counts.

Safety data including laboratory evaluations and vital signs assessments is summarized by dose level and time point of collection. Descriptive statistics are calculated for quantitative safety data and frequency counts are compiled for classification of qualitative safety data. In addition, a mean change from baseline table is provided for vital signs and a shift table describing out of normal range shifts is provided for clinical laboratory results.

ECG results are classified as normal and abnormal and summarized using frequency counts by dose group and time point of collection. Descriptive statistics are calculated for PR, QRS, QT, and QTc intervals.

Changes in physical exams are described in the text of the final report.

Heart rate data are summarized by treatment group and time point using descriptive statistics, as will individual change from baseline values. Mean change from baseline results are used to compare active dose groups to placebo at each time point. Data from six completed subjects per dose level should provide 80% certainty to detect a difference of 20 beats per minute. An interim analysis is completed following each period.

VIII. Assessment of Efficacy

VAS sedation scores are summarized by time point of collection for each dose level using descriptive statistics.

EXAMPLE 8

Preclinical Evaluation of Loxapine Analogs

Prior to human clinical testing of compounds, pre-clinical testing is performed. Pre-clinical evaluation includes the following tests:

i. Preclinical Absorption, Distribution, Metabolism and Excretion

The compound is administered to rats, dogs, and cynomolgus monkeys at a dose of approximately 3 mg/kg orally and intravenously. Plasma samples were collected from all species for pharmacokinetic analysis. The Tmax and half life (in hours) is measured in the rat, dog, and monkey. Percent protein bound in rat and human plasma is also measured.

The brains are collected from rats after oral administration to determine brain levels of the parent drug.

Cytochrome P450 inhibition is studied in vitro. In addition, the in vitro rate of metabolism in rat, dog, monkey, and human hepatocyte cultures is determined for each compound.

ii. Cardiac Effects Focus

The primary toxicological issue studied during the clinical candidate selection phase of the project is QT interval prolongation. Historically, H1 antagonists have been associated with this effect. QT prolongation in rare instances can evolve into life-threatening cardiac arrhythmias. The best in vitro test to predict the likelihood of a compound causing QT prolongation, the hERG binding assay, was the test system chosen to study the potential of a compound to produce this effect. The human hERG channel, transfected to a stable cell line, is studied electrophysiologically and the percent inhibition of the channel current is reported.

To determine if a compound can produce any changes in QT interval, the compound is studied in telemetered Beagle dogs. Dogs are implanted with devices to continuously monitor ECG and arterial blood pressure. Dogs (groups of 4) are studied in a Latin square cross-over design, with each dog receiving 3 different doses and a placebo. Two studies are conducted with doses of 0.3, 1, 3, 10, and 30 mg/kg.

iii. Acute Rat Study

The purpose of this study is to evaluate the toxicity and maximum tolerated dose (MTD) of the test articles when given via oral gavage to rats. Male Crl: CD®(SD)IGS BR rats (3/group) are assigned to 5 groups. At initiation of dosing, animals are approximately 7 weeks old with body weights ranging from 172 to 206 g. Each group receives either 50, 100, 150, 200, or 250 mg/kg of the compound once daily for 5 days. All surviving animals are sacrificed on Day 6. Assessment of toxicity is based on mortality, clinical observations, and body weight data.

iv. Acute Dog Study

The purpose of this study is to evaluate the toxicity and the maximum-tolerated dose (MTD) of the compound when given at escalating doses via oral gavage to dogs. Two male purebred Beagles are assigned to the study. At initiation of dosing, animals are at least 6 months old with body weights ranging from 8.0 to 10.9 kg. Dogs receive dose preparations containing the compound once daily for 5 days in escalating doses of 25, 50, or 75 mg/kg.

The dogs are observed at 0.25, 0.5, 0.75, 1.0, 1.5, and 2.0 hours ±5 minutes and 4, 6, 8, and 24 hours ±15 minutes postdose. They are weighed on Days 1 and 6.

Electrocardiograms are performed and blood pressures are taken prior to dosing and at 1, 4, and 24 hours after the 40 mg/kg dose on Day 5.

Based on the range and severity of the clinical signs observed, the MTD is calculated for the compound.

v. 14-Day Rat Study with Recovery Study

The purpose of this study is to evaluate the toxicity of the compound when administered via oral gavage to rats for at least 14 days and to assess the reversibility, persistence, or delayed occurrence of any effects after a recovery period of up to 14 days.

Male and female Crl:CD®(SD)IGS BR rats are assigned to seven groups, four main study groups and three groups for toxicokinetics. Each group receives dose preparations containing 0.25% methylcellulose, 400 cps in 200 mM acetate buffer, or 10, 30, or 150 mg of test article/kg of body weight (mg/kg/day) at a dose volume of 5 mL/kg.

Assessment of toxicity is based on mortality, clinical and ophthalmic observations, body weights, food consumption, clinical pathology, organ weights, and macroscopic and microscopic findings. Blood samples are collected for toxicokinetic evaluation.

14-Day Dog Study with Recovery Phase

The toxicity and the toxicokinetics of a compound of the invention when administered daily via oral gavage (Phase 1) or capsules (Phase 2) to dogs for at least 14 days is determined. The reversibility, persistence, or delayed occurrence of observable effects following a 7-day (Phase 1) or 14-day (Phase 2) recovery period is also assessed. Doses of 3, 10, 30, and 70 mg/kg/day are studied. All Phase 1 and 2 dogs survived until scheduled sacrifice.

The above compounds and protocols are useful in the preclinical evaluation of loxapine compounds of the invention.

EXAMPLE 9

Evaluation of Analgesic Activity

The analgesic activity of a loxapine analog following oral administration is analyzed. Analgesic activity is assessed by abdominal spasm tests in the rat and mouse. Analgesic activity is also assessed using the tail clip test in the mouse, tail flick test in the rat, Randall-Selitto test in the rat and comparisons are made with a vehicle control group. Reference compounds ASA (acetylsalicylic acid) and morphine are also included for comparison.

The tail clip and tail flick test provide useful information about the central analgesic activity of the test article. The Randall-Selitto test provides information on the compound's ability to modify a hyperalgesic state and the abdominal spasm test provides information on the peripheral analgesic activity of the test article. The test article is administered by oral gavage, this being the intended clinical route of administration. The dose levels employed are expected to encompass the efficacy dose and provide an adequate safety margin.

Test Article, Reference Compound and Irritant Formulation

All formulations are prepared on each day of dosing. The test article is formulated in 0.25% (w/v) MC at the highest concentration required. Lower doses are obtained by serial dilution of the highest concentration using 0.25% (w/v) MC. The reference compound, acetylsalicylic acid, is formulated in 0.25% (w/v) MC at the required concentrations. Brewer's yeast is formulated in water for injection at the required concentration. Acetic acid is diluted with water for injection to provide the required concentration for administration.

Dose levels will be expressed in terms of the amount of test article I reference compound/irritant administered without regard to purity or active content.

Animals

An adequate number of male Crl:CD-I(ICR)BR mice and Wistar rats are obtained from Charles River (UK) Ltd., Margate, Kent. The mice are approximately 4 weeks of age and weigh between 18 and 22 g on arrival. The rats are approximately 5 weeks of age and weigh between 150 and 170 g on arrival. The age and weight of the animals at the start of the study is documented in the raw data and final report.

The animals are housed in groups appropriate to the size of caging used, in cages that conform to the Code of Practice for the housing and care of animals used in the Scientific Procedures Act (Home Office Animals Scientific Procedures Act 1986). Bedding is provided on a weekly basis to each cage by use of clean Aspen wood chips (Dates and Ltd, Manchester, UK). The bedding is analyzed for specific contaminants and the results retained on file at Covance. The cages are cleaned and dried before use. Aspen chew blocks are placed within the cages as a form of environmental enrichment. Routinely, holding rooms are maintained within acceptable limits for temperature and relative humidity (nominally 19 to 25° C. and 40 to 70%, respectively). These rooms are illuminated by fluorescent light for 1.2 hours out of each 24 hour cycle and designed to receive at least 15 fresh air changes per hour.

RM1.(E).SQC., (Special Diets Services Ltd., Witham, UK) and water from the mains tap supply will be provided ad libitum, except where specified below. These are routinely analyzed for specific constituents and are not known to contain any biological or chemical entity which might interfere with the test system. The treatment groups employed for the study are as shown in Table 9:

TABLE 9

| | Treatment Groups. | | | |
|---|---|---|---|---|
| Group | Treatment | Dose level (mg/kg) | conc. (mg/mL) | #of animals |
| 1 | Vehicle | — | — | 8 |
| 2 | Loxapine Analog | 3 | 0.3 | 8 |
| 3 | Loxapine Analog | 10 | 1.0 | 8 |
| 4 | Loxapine Analog | 30 | 3.0 | 8 |
| 5 | Morphine | 100 | 10.0 | 8 |

Measurements of pressure is taken from the left and right hind paws of each animal immediately prior to administration of vehicle, test article or reference compound and at 30, 60, 120 and 240 minutes post-oral administration. The order of the pressure measurements is left paw followed by right paw.

Abdominal Spasm Test in the Rat

Each animal receives a single administration of vehicle, test article or reference compound by oral gavage, using a constant dose volume 10 mg/kg. Individual dose volumes are based on individual body weights obtained on the day of dosing. The treatment groups are shown in Table 10.

TABLE 10

| | | Treatment Groups. | | |
|---|---|---|---|---|
| Group | Treatment | Dose level (mg/kg) | Conc, (mg/mL) | # of animals |
| 1 | Vehicle | — | — | 6 |
| 2 | Loxapine Analog | 3 | 0.3 | 6 |
| 3 | Loxapine Analog | 10 | 1.0 | 6 |
| 4 | Loxapine Analog | 30 | 3.0 | 6 |
| 5 | ASA | 100 | 10.0 | 6 |

Forty-five minutes following oral administration each animal receives a 1 mL intraperitoneal injection of 1% acetic acid. Animals are immediately placed into individual observation chambers and the number of abdominal spasms elicited over the subsequent 25-minute period is recorded.

Abdominal Spasm Test in the Mouse

Each animal receives a single administration of vehicle, test article or reference compound by oral gavage, using a constant dose volume 10 mL/kg. Individual dose volumes are based on individual body weights obtained on the day of dosing. The treatment groups are shown in Table 11.

TABLE 11

| | | Treatment Groups. | | |
|---|---|---|---|---|
| Group | Treatment | Dose level (mg/kg) | Conc. (mg/mL) | # of animals |
| 1 | Vehicle | — | — | 6 |
| 2 | Loxapine Analog | 3 | 0.3 | 6 |
| 3 | Loxapine Analog | 10 | 1.0 | 6 |

TABLE 11-continued

| | | Treatment Groups. | | |
|---|---|---|---|---|
| Group | Treatment | Dose level (mg/kg) | Conc. (mg/mL) | # of animals |
| 4 | Loxapine Analog | 30 | 3.0 | 6 |
| 5 | ASA | 100 | 10.0 | 6 |

Forty-five minutes following oral administration each animal receives a 0.25 mL intraperitoneal injection of 0.5% acetic acid. Animals are immediately placed into individual observation chambers and the number of abdominal spasms elicited over the subsequent 25-minute period is recorded.

Terminal Procedures

At the end of each test, the animals are humanely killed by a Schedule 1 compound (e.g.e.g., exposure to carbon dioxide gas in a rising concentration followed by dislocation of the neck) and discarded without necropsy. If an animal showed any sign of serious discomfort during the study it is sacrificed immediately and humanely. Any animal found dead or killed prematurely during the study is subjected to a necropsy. A macroscopic examination is performed, after opening the thoracic and abdominal cavities, by observing the appearance of the tissues in situ. Any abnormalities are recorded.

EXAMPLE 10

Synthesis of Acylsulfonamides

The synthesis of acylsulfonamide Compound 40 is summarized in Scheme I. This procedure is applicable as a general synthesis of acylsulfonamides from the corresponding acids described herein.

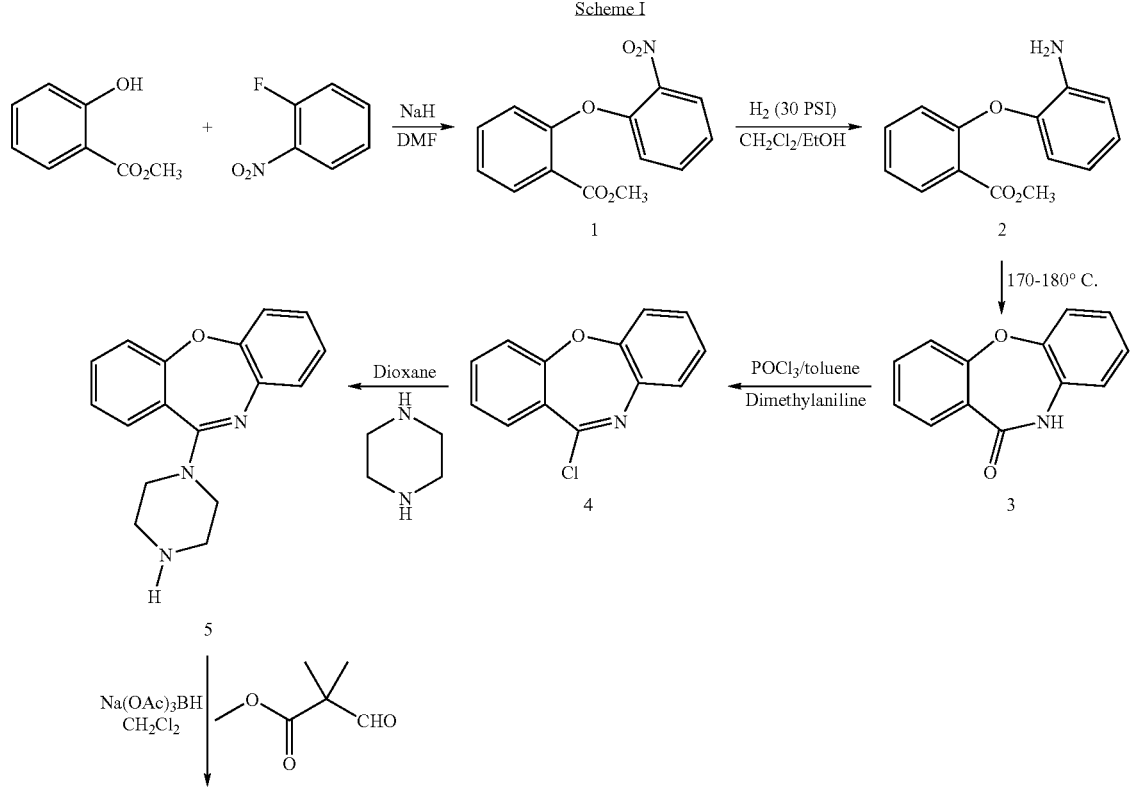

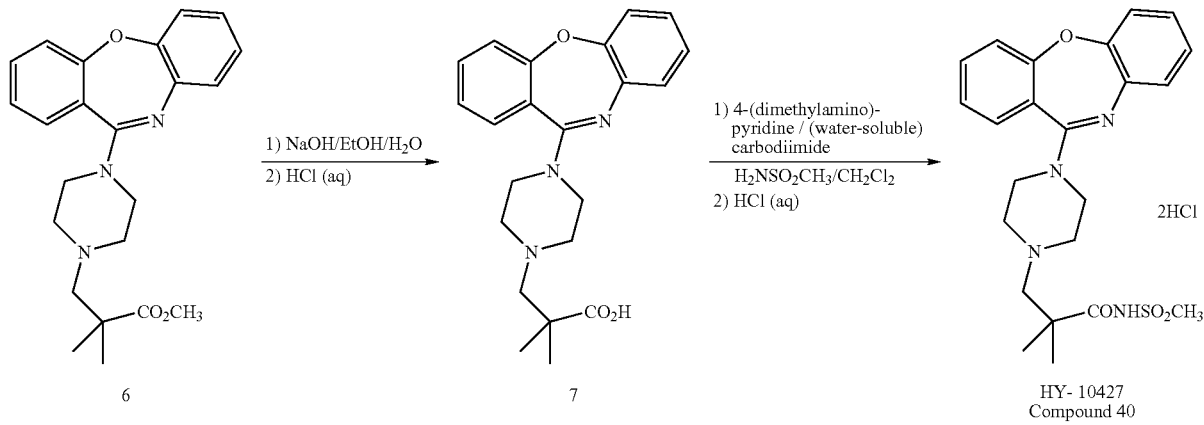

The treatment of tricyclic 10H-Dibenzo[b,f][1,4]oxazepin-11-one (3) with phosphorous oxychloride in the presence of N,N-dimethylaniline in toluene provided imidoyl chloride(4), which was converted to 11-Piperazin-1-yl-dibenzo[b,f][1,4]oxazepine (5) upon reaction with excess piperazine. Reductive amination of the tricyclic amidine (5) with 2-carbomethoxy 2-methyl propionaldehyde gave alkylated piperazine (6), which was purified over silica gel. Basic hydrolysis of the methyl ester of 5 in aqueous ethanol followed by acidification gave the carboxylic acid (7). The carboxylic acid (7) was converted to the acyl methyl sulfonamide by coupling with methane sulfonamide using the water-soluble carbodiimide, EDCI in dichloromethane with dimethylamino pyridine as a catalyst. Acidification of the coupling product gave the desired acylsulfonamide Compound 40 (HY-10427) as the bis-HCl salt.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims. It will be understood by those skilled in the art that various changes in form and details may be made therein without departing from the scope of the invention encompassed by the appended claims.

What is claimed is:

1. A compound having the formula of Compound 1:

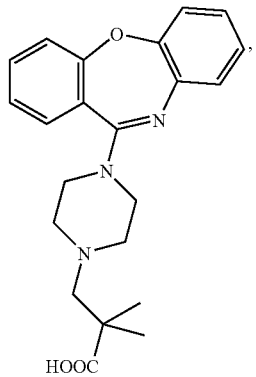

or a pharmaceutically acceptable salt thereof.

2. The salt of claim 1, wherein the salt is an acid addition salt.

3. The salt of claim 2, wherein the salt is a hydrochloride salt.

4. The salt of claim 3, wherein the salt is:

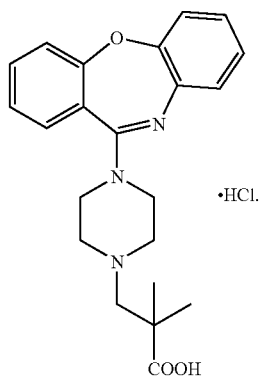

5. A pharmaceutically composition comprising Compound 1:

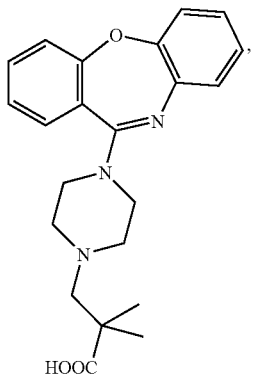

or a pharmaceutically acceptable salt, thereof, and at least one pharmaceutically acceptable excipient.

6. The composition of claim 5, wherein the salt is an acid addition salt.

7. The composition of claim 6, wherein the salt is a hydrochloride salt.

8. The pharmaceutical composition of claim 7, wherein the salt is:

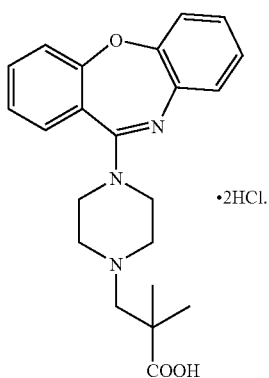

9. A method of modulating sleep in a subject, comprising administering to a subject in need thereof a therapeutically effective amount of Compound 1:

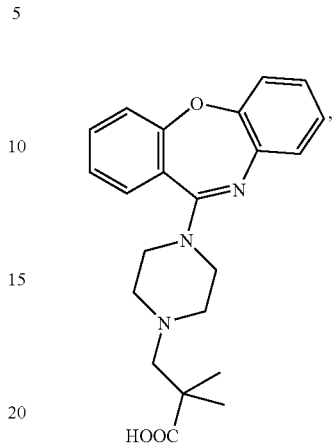

or a pharmaceutically acceptable salt thereof.

10. The method of claim 9, wherein the sleep modulation is selected from decreasing the time to sleep onset, increasing the average sleep bout length, and increasing the maximum sleep bout length.

11. The method of claim 10, wherein the sleep modulation treats a sleep disorder.

12. The method of claim 11, wherein the sleep disorder is selected from circadian rhythm abnormality, insomnia, parasomnia, sleep apnea syndrome, narcolepsy and hypersomnia.

13. The method of claim 9, wherein the compound or pharmaceutically acceptable salt is administered as a pharmaceutical composition comprising at least one pharmaceutically acceptable excipient.

14. The method of claim 9, wherein the subject is a human.

* * * * *

UNITED STATES PATENT AND TRADEMARK OFFICE
CERTIFICATE OF CORRECTION

PATENT NO. : 7,592,333 B2  
APPLICATION NO. : 11/233417  
DATED : September 22, 2009  
INVENTOR(S) : Dale M. Edgar et al.

Page 1 of 1

It is certified that error appears in the above-identified patent and that said Letters Patent is hereby corrected as shown below:

Column 137, Line 1, Claim 5

"5. A pharmaceutically composition comprising Compound 1:"  
should read  
--5. A pharmaceutical composition comprising Compound 1:--

Column 137, Line 19, Claim 5

"or a pharmaceutically acceptable salt, thereof, and at least one pharmaceutically acceptable excipient."  
should read  
--or a pharmaceutically acceptable salt thereof, and at least one pharmaceutically acceptable excipient.--

Signed and Sealed this

Twelfth Day of January, 2010

David J. Kappos  
*Director of the United States Patent and Trademark Office*

UNITED STATES PATENT AND TRADEMARK OFFICE
CERTIFICATE OF CORRECTION

| | |
|---|---|
| PATENT NO. | : 7,592,333 B2 |
| APPLICATION NO. | : 11/233417 |
| DATED | : September 22, 2009 |
| INVENTOR(S) | : Edgar et al. |

Page 1 of 1

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 617 days Delete the phrase "by 617 days" and insert -- by 903 days --

Signed and Sealed this

Twenty-seventh Day of April, 2010

David J. Kappos
*Director of the United States Patent and Trademark Office*

UNITED STATES PATENT AND TRADEMARK OFFICE
CERTIFICATE OF CORRECTION

PATENT NO.        : 7,592,333 B2
APPLICATION NO.   : 11/233417
DATED             : September 22, 2009
INVENTOR(S)       : Dale M. Edgar et al.

It is certified that error appears in the above-identified patent and that said Letters Patent is hereby corrected as shown below:

At Column 136, Line 60, Claim 4, the right-hand salt should appear as follows:
•2HCl Signed and Sealed this Twenty-first Day of December, 2010

David J. Kappos
*Director of the United States Patent and Trademark Office*